US005977435A

United States Patent [19]

Lefebvre et al.

[11] Patent Number: 5,977,435

[45] Date of Patent: Nov. 2, 1999

[54] PLANT PHOSPHATASES

[75] Inventors: Daniel D. Lefebvre, Kingston; Kevin S. Gellatly, Saskatoon, both of Canada

[73] Assignee: Performance Plants, Inc., Kingston, Canada

[21] Appl. No.: 08/955,138

[22] Filed: Oct. 21, 1997

[51] Int. Cl.[6] .......................... C12N 15/29; C12N 15/82; C12N 15/84; A01H 4/00

[52] U.S. Cl. ......................... 800/278; 435/419; 435/69.1; 435/440; 435/468; 435/410; 536/23.6; 536/23.1; 800/278; 800/282

[58] Field of Search .................................... 435/419, 69.1, 435/440, 468, 410; 536/23.6, 23.1; 800/278, 282

[56] References Cited

PUBLICATIONS

Napoli et al. The Plant Cell. 1989. vol. 2: 278–289.

Bingham, E.W., et al., "Removal of Phosphate Groups from Casein with Potato Acid Phosphatase", *Biochem. Biophys. Acta* 429:448–60 (1976).

Chen, R.H. and Blenis, J., "Identification of Xenopus S6 Protein Kinase Homologs ($pp90^{RSK}$) in Somatic Cells: Phosphorylation And Activation During Initiation of Cell Proliferation", *Mol. Cell. Biol.* 10:3204–15 (1990).

Cheng, H.F. and Tao, M., "Purification and Characterization of a Phosphotyrosyl–Protein Phosphate from Wheat Seedlings", *Biochem. Biophys. Acta* 998:271–6 (1989).

Cho, H. et al. "Purification and Characterization of a Soluble Catalytic Fragment of the Human Transmembrane Leukocyte Antigen Related (LAR) Protein Tyrosine Phosphate from a *n Escherial coli* Expression System", *Biochemistry* 30:6210–6 (1991).

Chung, R.P.T. and Polya, G.M., "Copurification and Characterisation of Poppy Seed Phosphatase and Phosphoprotein Phosphate Activities" *Plant Sci.* 84:153–162 (1992).

Duff, S.M.G., et al., "The Role of Acid Phosphatases in Plant Phosphorus Metabolism", *Physiol. Plant.* 90:791–800 (1994).

Duff, S.M.G., et al., "Purification, Characterization, and Subcellar Localization of an Acid Phosphatase from Black Mustard Cell–Suspension Cultures: Comparison with Phosphoenolpyruvate Phosphatase", *Arch. Biochem. Biophys.* 286:226–32 (1991a).

Duff, S.M.G., et al., "Phosphate–Starvation Response In Plant Cells: De Novo Synthesis and Degradation of Acid Phosphatases", *Proc. Nat. Acad. Sci. USA* 88:9538–42 (1991b).

Elliot, D.C., and Geytenbeek, M., "Identification of Products of Protein Phosphorylation in T37–Transformed cells and Comparison with Normal Cells"*Biochem. Biophys. Acta* 845:317–23 (1985).

Erion, J.L., et al., "Tomato Acid Phosphatase–1 Gene from a Nematode Resistant Cultivar" *Plant Physiol.* 98:1535–7 (1992).

Gellatly, K.S., et al., "Purification and Characterization of a Potato Tuber Acid Phosphatase Having Significant Phophotyrosine Phosphate Activity" *Plant Physiol.* 106:223–32 (1994).

Gellatly, K.S., and Lefebvre, D.D., "Identification of a cDNA Clone Coding for a Novel Calcium–Binding Protein from Potato Tuber" *Plant Physiol.* 101:1405–6 (1993).

Jagiello, I, et al "Identification of Protein Phosphatase Activities in Maize Seedlings" *Biochem. biophys. Acta* 1134:129–36 (1992).

Kamps, M.P. and Sefton, B.M., "" *Oncogene* 2:305–15 (1988).

Lefebvre, D.D., et al., "Response to Phospate Deprivation in *Brassica nigra* Suspension Cells" *Plant Physiol.* 93:504–11 (1990).

Polya, G.M. and Wettenhall, R.E.H., "Rapid Purification And N–Terminal Sequencing of a Potato Tuber Cyclic Nucleotide Binding Phosphatse" *Biochem. Biophys. Acta* 1159:179–84 (1992).

Pot, D.A. and Dixon, J.E., "A Thousand and Two Protein Tyrosine Phosphatases" *Biochem. Biophys. Acta* 1136:35–43 (1992).

Szabó–Nagy, A., et al., "Phosphatase Induction in Roots of Winter Wheat During Adaption to Phosphorus" *Physiol. Plant.* 70:544–52 (1987).

Uchimiya, H., et al., "Random Sequencing of cDNA Libraries Reveals a Varitey of Expressed Genes in Cultured Cells of Rice (*Oryza sativa* L.)" *The Plant Journal* 2:1005–9 (1992).

Zhang, Z.Y., "Are Protein–Tyrosine Phosphatase Specific for Phosphotyrosine?" *J. Biol. Chem.* 270:16052–5 (1995).

Zhao, H., "Continuous Spectrophotometric Assay of Protein Tyrosine Phosphatase Using Phosphotyrosine" *Anal. biochem.* 202:361–6 (1992).

*Primary Examiner*—Lynette R. F. Smith
*Assistant Examiner*—Ousama Zaghmout
*Attorney, Agent, or Firm*—Hamilton, Brook, Smith & Reynolds, P.C.

[57] ABSTRACT

This invention provides a novel family of plant phosphatases. Further provided are nucleic acids and nucleic acid constructs encoding the genes for plant phosphatases, cells containing the nucleic acids described and transgenic photosynthetic organisms with altered phosphate metabolism.

20 Claims, 19 Drawing Sheets

```
   1 ATCAACATAATGATGGTGTTCGTTGGGATTCTTGGGGGCGGCTTGTGGAACGTAGTACCG
     D  Q  H  N  D  G  V  R  W  D  S  W  G  R  L  V  E  R  S  T     20
  61 CTTATCAACCATGGATTTGGAGCGCTGGTAACCATGAAATTGAATACAGGCCTGATCTGG
     A  Y  Q  P  W  I  W  S  A  G  N  H  E  I  E  Y  R  P  D  L     40
 121 GAGAAACTTCTACATTTAAGCCATATCTGCATAGATGTCACACTCCATATTTGGCATCAA
     G  E  T  S  T  F  K  P  Y  L  H  R  C  H  T  P  Y  L  A  S     60
 181 AGAGCAGTTCTCCTATGTGGTATGCAGTCAGACGTGCATCTGCTCATATCATTGTGCTTT
     K  S  S  S  P  M  W  Y  A  V  R  R  A  S  A  H  I  I  V  L     80
 241 CTAGCTATTCTCCATTCGTAAAATACACTCCTCAATGGACCTGGTTGAAGTATGAATTGA
     S  S  Y  S  P  F  V  K  Y  T  P  Q  W  T  W  L  K  Y  E  L    100
 301 AGCATGTGGATAGAGAGAAGACTCCTTGGCTTATTGTTCTCATGCATTCTCCCATGTACA
     K  H  V  D  R  E  K  T  P  W  L  I  V  L  M  H  S  P  M  Y    120
 361 ACAGCAATGAAGCACATTACATGGAGGGTGAGAGTATGAGGGCTGCTTTTGAGAAATGGT
     N  S  N  E  A  H  Y  M  E  G  E  S  M  R  A  A  F  E  K  W    140
 421 TTGTGAAGTACAAGGTTGACTTGGTATTTGCAGGGCATGTGCATGCTTATGAGAGATCGT
     F  V  K  Y  K  V  D  L  V  F  A  G  H  V  H  A  Y  E  R  S    160
 481 ATCGTATCTCTAACATCAACTACAACATAACATCGGGTAATCGATATCCAGTGCCAGACA
     Y  R  I  S  N  I  N  Y  N  I  T  S  G  N  R  Y  P  V  P  D    180
 541 AATCTGCTCCTGTGTACATAACAGTTGGTGATGGAGGCAACCAGGAAGGGCTTGCTTCAA
     K  S  A  P  V  Y  I  T  V  G  D  G  G  N  Q  E  G  L  A  S    200
 601 GGTTCAGTGATCCACAGCCAGACTACTCTGCATTCAGGGAGGCTAGTTATGGTCATTCGA
     R  F  S  D  P  Q  P  D  Y  S  A  F  R  E  A  S  Y  G  H  S    220
 661 TCTTGCAACTGAAAAACAGGACTCATGCTATCTACCAGTGGAATAGAAACGATGATGGGA
     I  L  Q  L  K  N  R  T  H  A  I  Y  Q  W  N  R  N  D  D  G    240
 721 AGCATGTACCTGCGGACAATGTGGTGTTTCACAACCAGTATTGGGCAAGCAACACTCGCC
     K  H  V  P  A  D  N  V  V  F  H  N  Q  Y  W  A  S  N  T  R    260
 781 GCAGGAGGCTGAAGAAGAAGCATTTTCACTTGGATCAAATTGAGGACTTGATATCCGTGT
     R  R  R  L  K  K  K  H  F  H  L  D  Q  I  E  D  L  I  S  V    280
 841 TCTAGAGTGATCTTTCAGAACACGCATCGCAGACTTTCTGAAACGGTGGCGGAATAGCTC
     F                                                             281
 901 TGTTGCCCTTTGGTCTTGAGCCTCGACCGAGTGAGGCAGAGGCTCTCGGCTCTCATGTAA
 961 AGGAACCATGCACAGGTTTGTGGGATTACTATTATTGAGCACTGTATTGTATGATGAAGA
1021 CAATCCGATCAGCAGATGATTAGTGCTGTACACATGTAGCATTTCACAGCCAGCGACAGT
1081 TTCGCAATGTGACAGTATCTTCAATAAAGTTTCAAAGGGTTGTGAACCGAGATTGCAGCA
1141 TTAGCTGCCCTCTGTTCGTA
```

FIG. 1

```
  1 CTTGAAAATGAAGTACTGTCAGTTCCAAACGGTTATAACGCTCCACAGCAAGTGCATATT
     L  E  N  E  V  L  S  V  P  N  G  Y  N  A  P  Q  Q  V  H  I    20
 61 ACACAAGGTGACTATGATGGGGAAGCTGTCATTATTTCATGGGTAACTGCTGATGAACCA
     T  Q  G  D  Y  D  G  E  A  V  I  I  S  W  V  T  A  D  E  P    40
121 GGGTCTAGCGAAGTGCGATATGGCTTATCTGAAGGGAAATATGATGTTACTGTTGAAGGG
     G  S  S  E  V  R  Y  G  L  S  E  G  K  Y  D  V  T  V  E  G    60
181 ACTCTAAATAACTACACATTCTACAAGTACGAGTCCGGTTACATACATCAGTGCCTTGTA
     T  L  N  N  Y  T  F  Y  K  Y  E  S  G  Y  I  H  Q  C  L  I    80
241 ACTGGCCTTCAGTATGACACAAAGTACTACTATGAAATTGGAAAAGGAGATTCTGCCCGG
     T  G  L  Q  Y  D  T  K  Y  Y  Y  E  I  G  K  G  D  S  A  R   100
301 AAGTTTTGGTTTGAAACTCCTCCAAAAGTTGATCCAGATGCTTCTTACAAATTTGGCATC
     K  F  W  F  E  T  P  P  K  V  D  P  D  A  S  Y  K  F  G  I   120
361 ATAGGTGACCTTGGTCAAACATATAATTCTCTTTCAACTCTTCAGCATTATATGGCTAGT
     I  G  D  L  G  Q  T  Y  N  S  L  S  T  L  Q  H  Y  M  A  S   140
421 GGAGCAAAGAGTGTCTTGTTTGTTGGAGACCTCTCCTATGCTGACAGATATCAGTATAAC
     G  A  K  S  V  L  F  V  G  D  L  S  Y  A  D  R  Y  Q  Y  N   160
481 GATGTTGGAGTCCGTTGGGATACATTTGGCCGCCTAGTTGAACAAAGTACAGCATACCAG
     D  V  G  V  R  W  D  T  F  G  R  L  V  E  Q  S  T  A  Y  Q   180
541 CCATGGATTTGGTCTGCTGGGAATCATGAGATAGAGTACTTTCCATCTATGGGGGAAGTA
     P  W  I  W  S  A  G  N  H  E  I  E  Y  F  P  S  M  G  E  V   200
601 GTTCCATTCAGATCGTTTCTATCTAGATACCCCACACCTTATCGAGCTTCAAAAAGCAGT
     V  P  F  R  S  F  L  S  R  Y  P  T  P  Y  R  A  S  K  S  S   220
661 AATCCCCTTTGGTATGCCATCAGAAGGGCATCTGCTCACATAATTGTCCTATCAAACTAT
     N  P  L  W  Y  A  I  R  R  A  S  A  H  I  I  V  L  S  N  Y   240
721 TCCCCTTTTGGTAAGTATACGCCACAATGGCATTGGCTGAAACAGGAATTTAAAAAGGTG
     S  P  F  G  K  Y  T  P  Q  W  H  W  L  K  Q  E  F  K  K  V   260
781 AACAGAGAGAAAACTCCTTGGCTTATAGTCCTTATGCATGTTCCTATCTACAACAGTAAT
     N  R  E  K  T  P  W  L  I  V  L  M  H  V  P  I  Y  N  S  N   280
841 GCAGCTCATTTCATGGAAGGGGAAAGCATGAGATCCGCCTACGAAAGATGGTTTGTCAAA
     A  A  H  F  M  E  G  E  S  M  R  S  A  Y  E  R  W  F  V  K   300
```

FIG. 2A

```
 901 TACAAAGTCGATGTGATCTTTGCTGGCCACGTCCATGCTTATGAAAGATCATATCGCATA
      Y  K  V  D  V  I  F  A  G  H  V  H  A  Y  E  R  S  Y  R  I    320
 961 TCTAATATACACTACAATGTCTCGGGTGGTGATGCTTATCCCGTACCAGATAAGGCAGCT
      S  N  I  H  Y  N  V  S  G  G  D  A  Y  P  V  P  D  K  A  A    340
1021 CCTATTTACATAACTGTTGGTGATGGAGGAAATTCAGAAGGCCTGACTTCAAGATTTAGA
      P  I  Y  I  T  V  G  D  G  G  N  S  E  G  L  T  S  R  F  R    360
1081 GATCCCCAGCCAGAATATTCTGCCTTTAGAGAAGCGTCATATGGGCATGCTATACTGGAA
      D  P  Q  P  E  Y  S  A  F  R  E  A  S  Y  G  H  A  I  L  E    380
1141 ATTAAGAACAGGACTCACGCATACTATAGCTGGAATAGAAACGATGATGGTAACGCAATT
      I  K  N  R  T  H  A  Y  Y  S  W  N  R  N  D  D  G  N  A  I    400
1201 ACAACCGATTCATTTACGCTTCATAACCAGCATTGG
      T  T  D  S  F  T  L  H  N  Q  H  W                            412
```

FIG. 2B

```
  1 GGTGACACTATAGAAGAGCTCGAGGATCGTATTTCCTGGATGCCTATATATAGAAGCTAC

 61 TACTCTTGATTAATGTGAAAGTTGAGTTTTCCCACAAGATGGGTGTGTTTGGTTATTGCA
                                              M  G  V  F  G  Y  C
121 TTTTCGTTGTTCTAAGTTTGATTGTGAATGAGTCAGTTTTATGCCATGGCGGAGTCACCA
    I  F  V  V  L  S  L  I  V  N  E  S  V  L  C  H  G  G  V  T
181 GTAGTTTTGTTAGGAAAGTTGAGAAGACAATTGATATGCCTCTGGATAGTGATGTCTTCC
    S  S  F  V  R  K  V  E  K  T  I  D  M  P  L  D  S  D  V  F
241 GTGTTCCTCCTGGATATAATGCGCCTCAACAGGTATCTTCATATTCTCATTCCAAGGAGA
    R  V  P  P  G  Y  N  A  P  Q  Q
301 CAGGTCGGAATGTATGGGAGTAGGTTTGCCTCTCGAGTCTCGTCCTACAAATGAAAGGCC

361 TCCCACAGGGTGCTTAGTAGCTAGTTTATGTTAGCTGCTTATTCTTGACCAAGTTATTAG

421 TGAAGAAACTCTCTTGTCAAAATTTTATTGTGAAAAATACTGCCAGTGTTTAAATTTTTT

481 ATCACATGTAATAAGCTTTTACTTATGCTTGTCACTTTCATGGAATTTGGTTTATTTGAC

541 AATTGATTCTATTTGGGGTTTCTTTATAAGGTTCATATAACACAAGGAGATCACGTGGGA
                                        V  H  I  T  Q  G  D  H  V  G
601 AAGGCGGTAATTGTTTCATGGGTGACTGTGGATGAACCTGGTTCAAGTACAGTAGTATAC
     K  A  V  I  V  S  W  V  T  V  D  E  P  G  S  S  T  V  V  Y
661 TGGCGTGAGAAAAGCAAGCTAAAGAATAAGGCCAATGGAAAAGTTACTACCTATAAGTTT
     W  R  E  K  S  K  L  K  N  K  A  N  G  K  V  T  T  Y  K  F
721 TATAACTATACATCTGGTTACATCCACCACTGTACTATCGAACATTTGAAGGTTAAACAT
     Y  N  Y  T  S  G  Y  I  H  H  C  T  I  E  H  L  K
781 TCTTTCTTTCATTCCTTGAACAAAATTTAGTATTGGGGATGCTCAAATTGACAATGGATT

841 TAATTCTCCTTTTGTAGTTCGATACCATATACTACTATAAGATTGGGATTGGGCACGTGG
                            F  D  T  I  Y  Y  Y  K  I  G  I  G  H  V
901 CACGAACCTTCTGGTTCGTAACTCCTCCAGAAGCTGGGCCTGATGTACCCTATACATTTG
    A  R  T  F  W  F  V  T  P  P  E  A  G  P  D  V  P  Y  T  F
```

FIG. 3A

```
 961 GTCTTATAGGTAACAATTCCAACCATATTATTGCTGTTGGAGCTTTCTTAGGTTATTTTA
     G  L  I
1021 CCATTGCTTTTGAGGTTTCATTTATATTGTGCTTTCATTTGTGTGGTGTTTATTAGTCAA
1081 TCCTGCATTTCATTACAGGGGATCTTGGTCAGAGTTTCGATTCAAACAAGACACTCACAC
                           G  D  L  G  Q  S  F  D  S  N  K  T  L  T
1141 ATTATGAATTAAATCCAATTAAGGGGCAAGCAGTGTTGTTCGTAGGGGACATATCTTACG
     H  Y  E  L  N  P  I  K  G  Q  A  V  L  F  V  G  D  I  S  Y
1201 CAGATAAGTATCCAAATCATGACAATAACAGATGGGATACTTGGGGAAGGTTTGCAGAGA
     A  D  K  Y  P  N  H  D  N  N  R  W  D  T  W  G  R  F  A  E
1261 GAAGTACTGCTTATCAACCTTGGATTTGGACCGCAGGAAATCATGAGATAGATTTTGCTC
     R  S  T  A  Y  Q  P  W  I  W  T  A  G  N  H  E  I  D  F  A
1321 CTGAAATTGTAAGTGATACCGTAATATTAGCTCATTGAGATTTAATGCATTTCTGAATTT
     P  E  I
1381 TAGATGGTTTTGGAATGGAATTTTGATGAATATATTTTGTTACTATCTGCAGGGGGAAAC
                                                          G  E  T
1441 AGAACCCTTCAAGCCCTACACTCATAGATATCATGTCCCGTATAAAGCATCAAACAGCAC
       E  P  F  K  P  Y  T  H  R  Y  H  V  P  Y  K  A  S  N  S  T
1501 ATCTCCACTTTGGTATTCAATCAAGCGAGCTTCAGCATATATCATAGTTTTATCCTCATA
       S  P  L  W  Y  S  I  K  R  A  S  A  Y  I  I  V  L  S  S  Y
1561 CTCGGCACATGGTAAGGATATGACATTCTTGCGAGTACTACTTAACAACTTAATCGATGG
       S  A  H
1621 TCACGTACTTCAACAGCATTGATAATTCATAATGCATTTTCTCGGTGACTTGAAGGCGAT

1681 TCGGAAAATTCAGGACTTGTGGATTTGTCTGTTTTTCTTACAGTTCCATTTGTTCTTTTC

1741 AAATTTTAGGCAAATACACTCCTCAATATAAATGGCTAGAGAAAGAACTACCAAAGGTTA
                 G  K  Y  T  P  Q  Y  K  W  L  E  K  E  L  P  K  V
1801 ACAGGACCGAGACTCCGTGGCTGTTTGTTTTAGTACATTCTCCATGGTATAACAGCTACA
     N  R  T  E  T  P  W  L  F  V  L  V  H  S  P  W  Y  N  S  Y
1861 ACAATCACTATATGGAAGGGGAAACCATGAGAGTAGTGTATGAGCCATGGTTTGTACAGT
     N  N  H  Y  M  E  G  E  T  M  R  V  V  Y  E  P  W  F  V  Q
1921 ACAAAGTAGATATGGTGTTTGCAGGTCATGTTCATGCTTATGAACGAACGGTATGTACAA
     Y  K  V  D  M  V  F  A  G  H  V  H  A  Y  E  R  T
```

FIG. 3B

```
1981 CTCAACCAGTTCTCTGTAGCTTATGTGAGAATCATAGTTTCATCTGTTATAGAAGATGAA
2041 ATTTTTATTGTGTTTCAGGAACGGATATCTAATGTGGCCTATAACGTTGTCAATGGAGAA
                             E  R  I  S  N  V  A  Y  N  V  V  N  G  E
2101 TGCAGTCCTATTAAAGATCAATCTGCTCCAATTTATATAACAATTGGCGATGGAGGAAAT
      C  S  P  I  K  D  Q  S  A  P  I  Y  I  T  I  G  D  G  G  N
2161 CTTGAAGGCCTAGCCACCAAGTAAGACTAATCGTCTATGTCTAGAAAGTTGTTTTATCTG
      L  E  G  L  A  T  K
2221 TTGTAATTGGCAATTTGTCAGACAAATAATCGCATATCTTGTACACTAATTTCAGCATGT
                                                           M
2281 CAGAGCCACAACCAGCTTACTCACGTTTCCGCGAGGCCAGTTATGGTCATGCCACTCTCG
     S  E  P  Q  P  A  Y  S  R  F  R  E  A  S  Y  G  H  A  T  L
2341 CCATCAAGAATAGAACTCATGCTTATTATAGTTGGCATCGTAATCAAGATGGATATGCTG
     A  I  K  N  R  T  H  A  Y  Y  S  W  H  R  N  Q  D  G  Y  A
2401 TGGAAGCTGATAAAATATGGGTTAATAATCGTTTTTGGCACCCAGTTGATGAGTCCACAA
     V  E  A  D  K  I  W  V  N  N  R  F  W  H  P  V  D  E  S  T
2461 CAGCCAAATCAGGGTGATATACACGAGATCTCATCTTTCTTTTCTTTCCTTTTTCCTATG
     T  A  K  S  G
2521 TAGCATTCTGTAATTTTGTTTCCTTACAAGGTACACGTAATGAGACAATTAGCATTTACA
2581 CTTGTATGTTGTTGTATGTATATTTCCTAATGAGAGATATAGCTGCAAAACCAGCCAGTG
2641 GACTATACAGTTTTCATATGCAACTGATACACAGAATATGTTGAACAAAAAATTACCCTG
2701 CAAGGTATAGAAGGTAACATCAAAGTACAAATGTGAACCGATTTTTCCCCCCATGAAATT
2761 CAAGTATTACTTTATGCATATGTAATGAGTTACAATATGACGGACTATTTCATCTTTTAC
2821 ACCATTAACATCGTAAAACATTGGCATTTGAAAGTACCTTTTTTGAACCAATCTTCACAA
2881 CAATTGAACATTTCACTTTTAGTTAATTCAATGATTCAAAAAAAGGTTTAAACAAAAATA
2941 ATAATTTACTTGCTAGCTTCATAATAACAAAATATACCTTAGGTAGGTGGCGTTTAGGTT
3001 AGTTCTAAGTTTAACTCTGAGATAATTAATTTAAGGTGTCAATTTTAAGACAATTGTTGT
3061 CTAGATTTAATTTTGGAAGAACAATTTCATAAAAGTAATAATATTTTGAAAAGTAATATT
3121 AAAATCCAAAAACCAAATAAATGCTTTCTAATTAGTGAAGTCGAAGCAAATGAAATATAG
3181 AAGAAAAGACAGAAAATAAAAGTTGGAATGAGTTTTAGGGGATGAAACAGGTTTCTAAAA
3241 TCAATCGTGCTCTTTAATCTATAAATTTATATAACTCGATGGAATCTTTATATAGTAAAT
3301 ATTGAGTCGTATTCTAGCTTAATAACTACTTCACCACTCCATATATTACTTTCTTTTTAT
3361 TGAAATGAAAAATGGCATTCAACTTATATAAATTCATTTCTTCTTTCTAGTCTAATTTAA
```

FIG. 3C

```
3421 CTATAGATGTAATTTGGGACAGCTAGAAAGGCTTGTTCGCAGTACTTTTGGTATGGGAAA
3481 AAATAAAAACGAATTTTATGGGAAGAAAGTGGAAAAATCAAAAGGAGAAGGGTGTTTCTC
3541 GTAAAGCATTATAGTTTCGGGGAGGAAATGACAAAAATAGAAAGAACAGGGAGTTACTCG
3601 CCACAAACTTTATATAAGATGCACCGTCACCAAAAAATGGCGCAGGAGACGGAAACTACT
3661 CAATTGCACATTCGCCTTAGTCGTCACAATTCACATTTTGGCAACTCCGTTTTCAGCCAT
3721 CGCCGAGAGAAAAAATAATAATTTCAAAAGCGCTTCCTCCACGATCTGGTTGCCGGAGGA
3781 GGCGATTTTTTGAATGAAGAGTTCACCTGAATTTTCTCGAAATGGCTGAATCGACGACAA
3841 TTCAGAGGAGCTCGCCTGAAGGTGATGATCATGAACTGAAGGAGGAGAATATTGAGAAGA
3901 AAAAGGATTTTACTGCAAATCCTGAGTTCTTCAGTTGTATGCTTCAGCCAGCGCCTGCCG
3961 ATTCAGATCCAAATTACATTG
```

FIG. 3 D

```
PTAP   -----------------------------------LENEVLSVPNGYNAPQQVH   57
KBPAP  -----------------------FVRKTNKNRDMPLDSDVFRVPPGYNAPQQVH   31
PAP3   MGVFGYCIFVVLSLIVNESVLCHGGVTSSFVRKVEKTIDMPLDSDVFRVPPGYNAPQQVH   60
RAP    ------------------------------------------------------   |
PAP7   ------------------------------------------------------   |
PAP11  ------------------------------------------------------   |

PTAP   ITQGDLVGRAMIISWTMDEPGSSEVRYGLSEGKYDVTVEGTLNNYTFYKYESGYIHQCL  117
KBPAP  ITQGDLVGRAMIISWTMDEPGSSAVRYWSEKNGRKRIAKGKMSTYRFFNYSSGFIHHTT   91
PAP3   ITQGDHVGKAVIVSWTVDEPGSSTVVYWREKSKLKNKANGKVTTYKFYNYTSGYIHHCT  120
RAP    ------------------------------------------------------   |
PAP7   ------------------------------------------------------   |
PAP11  ------------------------------------------------------   |

PTAP   ITGLQYTDTKYYYEIGKGDSARKFWFETPPKVDPDASYGFGIIGDLGQTYNSLSTLQHYM  177
KBPAP  IRKLKY-NYKYYYEVGLRNTTRRFSFITPPQTGLDVPYTFGLIGDLGQSFDSNTTLSHYE  150
PAP3   IEHLKF-DTIYYYKIGIGHVARTFWFVTPPEAGPDVPYTFGLIGDLGQSFDSNKTLTHYE  179
RAP    ------------------------------------------------------   |
PAP7   ------------------------------------------------------   |
PAP11  ------------------------------------------------------   |

PTAP   ASGAKS--VLFVGDLSYADRYQYNDVGVRWDTFGRLVEQSTAYQPWIWSAGNHEIEYFPS  235
KBPAP  LSPKKGQTVLFVGDLSYADRYPNHD-NVRWDTWGRFTERSVAYQPWIWTAGNHEIEFAPE  209
PAP3   LNPIKGLAVLFVGDISYADKYPNHD-NNRWDTWGRFAERSTAYQPWIWTAGNHEIDFAPE  238
RAP    -------------------ARDCHND-GVRWDSWGRLVERSTAYQPWIWSAGNHEIEYRPD   41
PAP7   ------------------------------------------------------   |
PAP11  ------------------------------------------------------   |
```

FIG. 4A

```
PTAP   MGEVVPFRSFLSRYPTPYRASKSSNPLWYAIRRASAHIIVLSNYSPFGKYTPQWHWLKQE  295
KBPAP  INETEPFKPFSYRYHVPYEASQSTSPFWYSIKRASAHIIVLSSHIAYGRGTPQYTWLKKE  289
PAP3   IGETEPFKPYTHRYHVPYKASNSTSPLWYSIKRASAYIIVLSSYSAHGKYTPQYKWLEKE  298
RAP    LGETSTFKPYLHRCHTPYLASKSSSPMWYAVRRASAHIIVLSSYSPFVKYTPQWTWLKYE  101
PAP7   ------------------------------------------------------------  1
PAP11  ------------------------------------------------------------  1

                        *                                    *  *
PTAP   FKKVNREKTPWLIVLMHVPIYNSNAAHFMEGESMRSAYERWFVKYKVDVIFAGHVHAYER  355
KBPAP  LRKVKRSETPWLIVLMHSPLYNSYNHHFMEGEAMRTKFEAWFVKYKVDVVFAGHVHAYER  329
PAP3   LPKVNRTETPWLFVLVHSPWYNSYNNHYMEGETMRVVYEPWFVQYKVDMVFAGHVHAYER  358
RAP    LKHVDREKTPWLIVLMHSPMYNSNEAHYMEGESMRAAFEKWFVKYKVDLVFAGHVHAYER  161
PAP7   -PKVNRTETPWLIVLLHSPWYNSNNYHYMEGESMRVMFESWFVQNKVDMVFAGHVHSYER  59
PAP11  ------------------------------------------------------------  1

PTAP   SYRISNIHYNVSGGDAYPVPDKAAPIYITVGDGGNSEGLTSRFRDPQPEYSAFREASYGH  415
KBPAP  SERVSNIAYKITDGLCTPVKDQSAPVYITIGDAGNYGVIDSNMIQPQPEYSAFREASFGH  389
PAP3   TERISNVAYNVVNGECSPIKDQSAPIYITIGDGGNLEGLATKMSEPQPAYSRFREASYGH  418
RAP    SYRISNINYNITSGNRYPVPDKSAPVYITVGDGGNQEGLASRFSDPQPDYSAFREASYGH  221
PAP7   SERVSNVMYNITNGQSTPIEDPSAPIYITIGDGGNIEGIANKFTEPQPSYSAYREASFGH  119
PAP11  ------------------------------------------DPQPDYSAFRESSYGH  16

PTAP   AILEIKNRTHAYYSWNRNDDGNAITTDSFTLHNQHW                          451
KBPAP  GMFDIKNRTHAHFSWNRNQDGVAVEADSVWFFNRHW--------------YPVDDST     432
PAP3   ATLAIKNRTHAYYSWHRNQDGYAVEADKIWVNNRFW--------------HPVDESTTAKS 465
RAP    SILQLKNRTHAIYQWNRNDDGKHVPADNVVFHNQYWASNTRRRRLKKKHFHLDQIEDLIS  281
PAP7   AILEIKNRTHAYYTWHRNQDSERVAADSLWIYNRHW--------------YPKKE-TSSMA 165
PAP11  STLEIKNRTHAFYHWNRNDDGKKVKIDSFVLHNLYW                          52
```

FIG. 4B

PAP1

```
AAAATAGAAAAAGTCTTCTTGTCCGACATAGGAACACTCAACGATTTTCTACCCAATATG    60
TGGTTTTGTAGTGTATTGAAGCGATACTGCCTTTATGTCAAATAAACAAAAGTGTTATAT   120
CTTGACTTTCTTTTACATATCTTACCATCTCTAATTTTTCTTGTAATCAAGGATTGAAAA   180
AGCAAGTACCTTCTCGCTACTCAAAAAAGAACCATTCATTGTATTTAGGTTGGTAGAATT   240
CCAAGCTGTTTCCTATGCAGAAGTTTTGCTTAGGGATGGCAAGGGGAGCCTTAACACGCA   300
AATTTTCAACCCGGGCCACATGAGTTTCTTCATGTCACTTCTTCTTTATAATATGAAGAT   360
ATGTGATGCAGCATTGAATGGACTAGATTAGAGCTTAGCTTTTTTTTTCTTATTTCATT   420
TTTTCTACTATATATAATGCAAGAGCTGTAAATTTTTTGTGCATTGCCTTTTCACTGGCT   480
CATAATGTTGAGAGAATTGGATCCAAATCTGTACTGTACTATTTT               525
```

FIG. 8A

PAP5

```
ATAAAATCAACTCTATGCCACCTAATTACACATTTTGAGGCCCTTTCCAAGGTCATATGT    60
ATTTGCAGAGGAAGGAAGTCATCTTTGGTAGGGAGCACTTACCCCTATAGCAAGACTTTC   120
CGGCATGAGGATTAGTCACCGCCAAAAGTGGACACCGGACATCAGGTCAAGGAAAACCAC   180
ATATATCTTTGAGAATACCATTGTCCATCTAGTACATAAATTGGTGTAAAATAGTAATCT   240
CTGTCGTAATAAATTATGAAAGAGAATTGACAAGATTCTTAAACTTACTTCAGAAAACAC   300
AGGAATCTCTTGTACGAGAAAAGAAGATAGTGAACGAATTCTTCGAAGGTTTGGTTTCAA   360
TGATTTTTCATTTGATTCGTAATATTAATCATGTTAGTAGCACAGATTCAATCATTTGAT   420
ACCTTTTACTTATATCGAGATTGGATCAGATGTATTTTTTTTGGATTACATTGATACTTT   480
TGGTGAATGGGCCTGCATTGGGTGGATGTAGATACAGAGTATTGATATGTGATATCATCG   540
ACTCAACTAGTTTAGGATTGAAGTATAGTTGGTTGATTCCTTGATATTGAGGTAATCAGA   600
ATATTAACATGATATAGTAGGA                                      622
```

FIG. 8B

```
CCAAAGGTTAACAGAACTGAAACTCCGTGGCTAATTGTTCTGCTTCACTCTCCATGGTAC   60
AACAGTAACAACTATCATTACATGGAAGGTGAAAGCATGAGAGTGATGTTCGAGTCCTGG  120
TTTGTTCAGAACAAGGTTGACATGGTGTTTGCAGGACATGTTCATTCTTATGAACGCTCG  180
GTAGGCCCCTCAACTCCATCCTATAAAATTTCATCCTTGAACCAATGTGTATAGGTCTTG  240
ATTAATGGTATATATGTCACATGGACAATTTCGTAGGAACGAGTATCAAATGTTATGTAC  300
AACATCACAAATGGACAGAGTACTCCAATTGAAGATCCTTCCGCGCCTATATACATAACA  360
ATTGGGGATGGTGGAAATATTGAAGGCATTGCTAACAAGTTAGACTTCTATTCGTTCTGA  420
TCTCATTTTTATTTAATCTGATGTAATGAGAAGAGTATCTGATGGGAGTCTGTCTGGTTT  480
TTGTTTGTGCAGTTTTACAGAACCACAGCCGAGCTACTCAGCTTATCGTGAAGCAAGTTT  540
TGGTCACGCGATTCTTGAAATTAAGAACAGAACTCACGCCTATTATACTTGGCATCGTAA  600
CCAAGACAGTGAACGAGTTGCAGCAGATTCTTTGTGGATTTACAATAGACACTGGTATCC  660
TAAAAAGGAAACCAGCTCTATGGCTTGAAAGTAACATGTTTGGTAGGCAGTGCAGTTGTT  720
ATTTTCCTAGAAACCATGTGTTCTATTAGATTAGTTCGTCGGGTACTAAACCAGTTCCCA  780
TTTATGATTTCTTAAAGACCTGTAAGAGGAAAATGTGACAACTAATATGGAACGAAGAGA  840
GTATACCTTAACCCTTAGTAGGTGGAAGTTTATTTTCTTATGCCTTCTCCAATCTTAGTA  900
CTTATTTTTTTTCTTTCAACTTCTTAATATATTTTTTTTCCGAACTTCAATTTTCAAATA  960
TTCTTTTTTTCTTTTTCATCTTTAACCAAATAAAACTCTCCTCCACTATTAAATATAACT 1020
GGCAGTGTCACATCAAGTCATTATCTATAACACTAGAAATAGATAAATATAACATCAATT 1080
TTAGGTTTGAAGGTTCATTATCATCAACACTAATTCCATATAAATTCAGTATGTATTACA 1140
GGTTACTTCTGTCCAATGCCATAAGATGTAATAAATATACATGAAAATGAACTTCACTTA 1200
TTTATGCCTTTAATTAATAGATTCTCTAAATACAAAGTACCTTCCAAAATATTAGCCAAC 1260
AGAAAATTAAAATCTTTTGCCCCTCTTTGGCTCGTCTAGTCTTCACTATAAATTGACCAT 1320
TTGTAACTATAATCTTCATCCCCCCTCACTACTCTTTAGCTAAGTGTTCTTTCTTTTTAT 1380
TCCTTTGTGTTTTTCTCAATCCTAAGAATTTGTCATTTCTTTATATTATTGGTTTTTAAG 1440
TTACATACACTGATATGAGTTGGGCTTCAAGAAAAGGCGAAAAATTTATATAGCCAACCA 1500
GGCAACCACAACTCGTTTGTGACTTAGGTGTAGGTTGTTGTTGTTGTTGTTGTTAAGTTA 1560
CATACATTAACAACATAAATATTTTTTTATGCTATCGGTATAGTTTATTTGATAACGTAA 1620
ATATTTACAAACAAGATTTGGTTGAGGATTCAAAGTGAGAAATTCTATTGACAGAAGAGA 1680
GAGAGTACAATCTGTCATCAGCAAAATGATATTGTTGTTTGTTGGAATGTACTCTCTCTG 1740
CTTCTGCCAAT                                                  1751
```

FIG. 9

```
ACTCGATCCATTTATTAGGATACATGTACTGCACTAGTAAGATTTTAGAACACTTACAAA   60
TACGTATGTACTATAAACATATTGGGATACTTGGAGCAACGATCAAGTTGTCCCCGTGTG   120
ACCTATAGGTCATGAGTTTGAGCTGTGAACTCAGTAACTGATCCTTGCATTAGTGTATGC   180
TTTCTACATCACACACTCCCTTGTGGTGTGGCCCTTCCTCGGACCCTGCATAAACATGTG   240
ATGTTTCGTGCACCGTGCTTATGTGCTTCAACTACCTTATAACTTCTTAAATTGCTCTAG   300
AACAAAAGATTCATTTGTTTATTTCTGCAGATTTAGAGATCCTCAACCAGATTACTCTGC   360
GTTCCGCGAATCCAGTTATGGTCATTCTACACTAGAGATTAAGAACAGAACACATGCATT   420
CTACCATTGGAACAGAAATGACGATGGAAAGAAGGTTAAAATCGATTCATTCGTGTTACA   480
CAATCTGTACTGGTCAGTATGATCTTCCTCCCTCTGCAGAATATATTTCATCTGGAGAAT   540
CTGAATTGAATTTTCTTTTAACTTACTGTAGTAGATAATCTGTCTTATTTTCCGAGGACT   600
AATCTCACTCACTATGGATGAGTATCATTAGTTATCATTTAGGCGAATTTTTCACATTGT   660
CAGTATATAGAGGTTAAACTCACGCGATTTATGGTCATGCAGGGGACAGAATCATCACCA   720
GAGAGAGACGAAACAAAATCGTCTCCGTTCACATCATTTTAAACAGGGCTTCAACTGCAC   780
AACTGTGAGAACATATTTCTGCAACTTACTCTCAACTTAGTTGCAGTTTTATGGCCATAT   840
AGATTAATATCCCAATGGCAACTAATAAGTTTGAATATCTATTTGCTCTCTTCGGACTAT   900
TTGGCAAATTACTTGAGCCGAGGGTTATCAAAAAACGTGTGCGTACACACTACCTTTCCA   960
GACCTTAGTTGTGGGATTATACGGGGTATGTTATTGGACTATTTGGCTAAATTTCCACCA   1020
AATATTTATCATTCAAATAAGAGTTTGTGCTGTTCACTGCATCATTTCAGTTTCTGAAGA   1080
ATTATTTTATTTGAATATTCACAATGCATTTACTTAATTTATTTTATTCTAGTTTTGGAA   1140
GATGAATGTTCCTTCAGAATATTTAATAGGCTAGTTTTTAGTTTTTCTTTTGAGAAAAAT   1200
CTTACCCGCCATCAAAGGTTGTGGTGAAGCAATAAATACTCATTCACCCTTAACAAAAGG   1260
TCTCGGATTTGACCTATGGATATGGAGTCTTCTTTGATAAGGAGTGTTTTACTCCCCTAA   1320
AGTGAAACTTTCCAGCATGAATCCGAATTAGTCAGACCCAAAGCAGGTATCGAGTGGGAA   1380
ACCAAAAAAGAAAAAAATCTACTTTTAGATGAGATGATCCATCACACTTGGTATCATAGT   1440
AGGCAGAGGTCCCTAGTTTGAGTCTCTATTCCAACCATTATCAAAACAAAGAAAATTCAC   1500
ATCCTTGGCCATTAAAAACGAATCAAGCTCACACACGAGAGGTTGTGTCGAAGACATCAT   1560
TGGGTAAATAAAAATGTGCTCAGATAGTCACACACTTCAACGAATGAAAAATTGTCTATA   1620
TAGCCAAGGCTAAAAAGAGAGTTGCTAGTAGTACATATAACTTCAACTAGAAAAATTACT   1680
CAATTTTTATTCTTGTCCAGCTTCAACTTCAGCTTCTCTTCAAAAGTTTCACAACTTTAC   1740
AGTATCTCTCTTCTGTTATTATTAAATCATGTACAGAAATATTCGATTATACGTGCTGTC   1800
GTTCCCAGTCTATTAGGAATCAAAGAAATTTACTCCCTGTACAAAACTAACAAGAATGTA   1860
AAACTGAAGTTTGATGTTCATCATTGGTAGTCTCTGTATATTGGCTGTGGATTCCATTTG   1920
AGATGCAAGTTCAGTTTCCCTGATTTAGCCTCGGCTAATTCGTACGTGTCTTTGTATTCA   1980
CCTTCCATTAGAACCCTTGTTAAAGTCAGTATGCATCTTCCCATGAAATCCTGTGAAGAA   2040
AGTTGGAA
```

FIG. 10

| Primer | Template | 5'→3' Sequence |
|---|---|---|
| 3-4a | genomic subclone 3-4 | CTC TCG GCG ATG GCT GAA A |
| 3-4b | " | TTA AGC TAG AAT ACG ACT CAA |
| 3-4c | " | TAA CCT AAA CGC CAC CTA CCT AAG |
| 3-4d | " | TAC TTT GAT GTT ACC TTC TA |
| 3-4e | " | TAC AAC AGA TAA AAC AAC TT |
| 3-4f | " | CTA AAA CAA ACA GCC ACG GAG |
| 3-4z | " | ATG CCT CTG GAT AGT GAT GTC TT |
| 3-4y | " | TCA TGG AAT TTG GTT TAT |
| 3-4x | " | AAC ATT CTT TCT TTC ATT C |
| 3-4w | " | ATG ACA ATA ACA GAT GGG ATA C |
| 3-4v | " | AAC AAC TTA ATC GAT GGT CAC G |
| 4-1.2a | genomic subclone 4-1.2H | GAT CAG CTT TCC CCA TTA G |
| 4-1.2z | " | AAA AAC TGC AAA TAA CAG |
| 4-1.4a | genomic subclone 4-1.4ES | CCT TTT CAC TGG CTC ATA ATG |
| 4-1.4z | " | CAA GGC ACT GAT GTA TGT AAC |
| 4-2.2a | genomic subclone 4-2.2EX | CAT GCA TTG AAC TAA GAC T |
| 4-2.2b | " | TGT CTC CTC TGC ACT AAC TTC C |
| 4-2.2z | " | ATT TAT TTT CAT GTG GGT GTG |
| 4-2.2y | " | CAG TTT CTT GAT GTT CTA AT |

FIG. 11A

| Primer | Template | 5'→3' Sequence |
|---|---|---|
| 4-4a | genomic subclone 4-3.8BS | AAA TTA CTC TCC GGA ACT TGA A |
| 4-4b | " | TGC ATA TAC TTA GTT GAT TAC AT |
| 4-4c | " | GCA CAA GCT AGT AGA TTT TTC AG |
| 4-4d | " | TCA GTA CAT TTC AAG ACA TT |
| 4-4e | " | GAC ACG TAA TCT CAC TTT T |
| 4-4f | " | TTC CCA GCA GAC CAA ATC CAT G |
| 4-4g | " | TAA ACT CAT CCA AAA GCC ATA GG |
| 4-4z | " | TCT CTT TGC ATG GCG ATA A |
| 4-4y | " | TCT GCA CGG AAG TTT TG |
| 4-4x | " | TGG TAG AGA TTA AAA AGA ACA TT |
| 4-4w | " | AGA CGT GCT GAA ACT ATT |
| 4-5a | genomic subclone 4-4.7BH | CTC ATG CTC ACT AGC T |
| 4-5b | " | GAA TAG CTA ATA CGC CA |
| 4-5c | " | CCT TCA TGT TGA AGT TT |
| 4-5d | " | CAA GGA CAG TTA CGG A |

FIG. 11B

| | | |
|---|---|---|
| 4-5e | " | TAC ATA ACT GTT GGT GG |
| 4-5f | " | GTC ACG GTC CTC CTG |
| 4-5g | " | CTC CAA CCA AGAA GGA C |
| 4-5h | " | ACG ATG ATG GTA ACG C |
| 7-2a | genomic subclone 7-1.7 | CCA CAA CCT ACA CCT AAG TCA CAA |
| 7-2b | " | GGC ATT GGA CAG AAG TAA CCT |
| 7-2c | " | TTA GTT GTC ACA TTT TCC TCT TAC |
| 7-2z | " | GAT GTT CGA GTC CTG GTT TGT |
| 7-2y | " | GTA TCT GAT GGG AGT CTG TCT GGT |
| 7-3a | genomic subclone 7-3.2 | CCT CGA CGA AAT CCA CAA G |
| 7-3b | " | ATC TTG AGC TAG GAG TTA TGG |
| 7-3c | " | CTA CGA AAG GAT GTG ATG |
| 7-3d | " | ATG AGC ACA AAA TAG ATG ATA |
| 7-3z | " | AAG TGT AGA AAA TATT GGG TTA GTA |
| 7-3y | " | GCC ACT AAT ATA ACC AAT CCA CAT |
| 7-3x | genomic subclone 7-3.2 | CCC CCA TAC CGA AAA GAG G |
| 11-2a | genomic subclone 11-2 | CTG ATG CTT GCA TTA GTG TAT |
| 11-2b | " | ATG ATG ATC TTC CTC CCT CTG C |
| 11-2c | " | TAC CTT TCC AGA CCT TAG T |
| 11-2z | " | CCT AAT AGA CTG GGA ACG ACA |
| 11-2y | " | TCT TCG ACA CAA CCT CTC |

FIG. 11C

| | | |
|---|---|---|
| PTAP-N | tuber cDNA clone | |
| | PTAP | GCA GGA TCC CGA ACT CAG TTT CCG TCT GTT GAT |
| A | | |
| PTAP-C | " | GAG GGA TCC ATG TTG CTT TAT ATC |
| PTAP-T | " | TTC TTT TTG TTA TC |
| RAP-1 | rice genomic DNA | GCA GGA TCC ATG GTC ATA TTT GCT |
| | | TGT GGA GAT AAT CCT |
| | | AGG CCT TTT G |
| RAP-2 | " | GAG GGA TCC CAT AAT TAA GGA GAA |
| | | AAA CAT ACA ACA AGA CT |
| RAP-3 | " | GAC GGA TCC GGA TAT GGC AGT GCG |
| | | AAG GTT GTC |
| RAP-4 | " | GAC GGA TCC GTT AAC CAT GCA ACT |
| | | CAG CAT TCC AC |
| RAP-5 | " | ATG TTG TAT GAC GCT CTT GAT ACC |

FIG. 11D

SEQUENCE LISTING

```
<160> NUMBER OF SEQ ID NOS: 119

<210> SEQ ID NO 1
<211> LENGTH: 9412
<212> TYPE: DNA
<213> ORGANISM: SOLANUM TUBEROSUM
<220> FEATURE:
<221> NAME/KEY: VARIANT
<222> LOCATION: (1)...(17)
<223> OTHER INFORMATION: Xaa = Any Amino Acid

<400> SEQUENCE: 1

gtgcctgagt ctctctgatc gagcagtgct atcttggaag ttagtgcaga ggagacaatg     60

ttgctttatc tcttcttttt gttatctctc tttttgacat ttatagacaa tgggatgcgt    120

aatcgatgct gaccatgctg atgccaaggt ataacaatgc gacttacctt gaactcagtt    180

tccgtctgtt gatattccct tgaaaatgaa gtactgtcag ttccaaacgg ttataacgct    240
```

```
ccacagcaag taagtttaca gtcttaaaac ctactttttg ttgtgttggc taaatctttc    300
ttagcaggtt tgttgttcat ctacagtcct ttcctagtca agtattggtc aattacttta    360
aatccaagtc ttagttcaat gcatgatatt caatcttctg atttgcaaag ttctctacaa    420
ccactttctt gagatactag aaaattgtga tttaaagaac attataatat tgctataaat    480
ttataagtag gtcgttcttg tcatgctcat ctgttttgca gaacatgaga agctcgaact    540
ccacattttg ttttctctga ctaatttcaa gctccatggt tgcttagaga ccagttaaac    600
attttgctcc tatatattct tttctatttc taatataatc tttcataaaa agcaaacaca    660
cccacatgaa aataaatgtg attagaacat caagaaagtg ttgggggtag agtacctttg    720
aaggctgaaa caacaaggga gtgaaccagc aaaaataaaa gatgattttt ttgaattgaa    780
atagtagaat tactacaaat caagtttaaa aaagcatgaa tattcaaggg aacatttgtt    840
cttaatcagt tcgatgagtg tgttgttggt taatttgatt gctcaaaact aaagaaatgt    900
taggagggat gtttggttac gtggcaattc ttttacagct ccgatcaaaa catgagatat    960
ttacgaagtt gcatgagaca acattttgac attcctactt caatgcaaaa tggattgaag   1020
tccgacacaa gttgaggga ctactctatt tcggtagctg atcgtaatcg ttaagctaaa   1080
ccaaatctta gtcccaattc tgcttttgga aatcttgtac tcccttcgtt tcaatttgtt   1140
aattaaatta accaacacac actcatcgaa ctgattaaga acaaatgttc ccttgaatat   1200
tcatgttttt ttaaacttga tttgtagtag ttctactatt tcaattcaaa aaaatcatct   1260
ttttgatata cccatttcaa aaaagattac atttttagtt cagaaatatc atagattttt   1320
gctggttcac tcccttgttg tttcagcctt caaagtcaat tataactggt gttgcctgag   1380
ttctctctga tcgagcagtg cttatcttgg aagttagtgg agaggagaca atgttgcttt   1440
atatcttctt tttgttatct ctctttttga catttataga caatgggagt gctggtataa   1500
caagtgcatt cattcgaact cagtttccgt ctgttgatat tcctgtctag ttttgacttg   1560
gagtggagtt taagaaagta aagagaactt tcgaatcatg tggtcttaaa ttaaagatat   1620
atagaatgtc tcaaaatgtt ctttgatctt gtggtcttaa agatgccaag tggaaagtta   1680
gaattaaaga gttatcaaaa aaggaaagaa gcattctttt ttaaaaggac taaaatggta   1740
atgaagcttg cattggtgat cctagtagct ggctactttt gtgctgtgtc ctgccaccat   1800
agctgtctgc aagggccaaa tcacaaagcg tccccaggcc cggagatcgg ctttcaggaa   1860
tgcttcttgt atgctgaaga ttcttgttgt tacgctaact ttaccgagaa gctggctcag   1920
tcccctgtta tagaggtgga taactattac tggaacagat gtgggaacct cagcaaaagt   1980
tgtgaagatt atatgaagaa gttagaatgc ttttaccagt gttccccaat gacagctcac   2040
agtaaagaca aattagttgg aatggaggga ctattcaaag gtccttccga ggttcaacga   2100
gaactaaatg tgtttgsttg aaccaagatc ggggcagccc aaagataaag tgggtcagag   2160
aaaccaagat tgttcaaaga attcgatatc aaaatcgaac tgattaagaa caaatgttcg   2220
caagctgttt cctatgcaga agttttgctt agggatggca aggggagcct taatccgcaa   2280
attttcaacc cgccccacat gagtttcatg tcacttcttc tttattaaat gaagatatgt   2340
gatgcagcat tgaatggact agattagagc ttagtttttt tttttcttat ttcatttttt   2400
ctactatata tatgcaagag ctgtaaattt tttgtgcatt gccttttcac tggctcataa   2460
tgttgagaga attggatcca aatctgtact gtactatttt tcattgtctt aattagaaaa   2520
agattaagct gcttatacca actgtttaat agtacttttt atacaatcaa tgcagtttag   2580
cataagttgg tttgtaatta ttttgatgga atatcaatta gttttagtta tgtattattt   2640
```

```
ggatataggt cacagaattg caatagtaga tgtcaaagtg cttctgtatt aaagtacttg   2700
tcaagaaatt tcttttcttt ttcagatcaa tgtccttaac tactagattt gtgcttgcaa   2760
caatgattgg attttacaaa gatattctgt gaattttttt tattgtgagt aatgccatga   2820
acaaattgat cagcaacccg ccctgccctg cataagcaaa aactcatccc gccccccttgt   2880
catccctagt tttctcatg tgtgttctct ttcataaaca tggattttga gatgacaatg   2940
ggtttatgtg gcctttaagt gctaacgact tcagtcattc ttctaggtgc atattacaca   3000
aggtgactat gatggggaag ctgtcattat ttcatgggta actgctgatg aaccagggtc   3060
tagcgaagtg cgatatggct tatctgaagg gaaatatgat gttactgttg aaggactcta   3120
aataactaca cattctacaa gtacgagtcc ggttacatac atcagtgcct tgtaactggc   3180
cttcaggtag gcaagaccaa cattttgtta tcctttttta aaaaatgaaa cagtgatcat   3240
ttttatctta tcggctatgg gataatatgc atcatgcaag tgcattttaa cgtagcgtat   3300
aggtgagcat tctcatatat ttttcccaga caaaatatgt acttcttagt tttctgtatt   3360
tcatctcaca gtaaaattgg caagcctgat atctcttctt agttcatatt ctctgtttca   3420
tttccacaaa gcaaagacta acaacaaggg gacttgctag aaaaaagaag tttaagaagg   3480
acaaaaaatg aagtacggtg taattacaag agtttgatat aaacttattg tcactcttta   3540
ctcctttttt ggtgtaacat ggctagcacc aacgtaaatg atatagacgc catgataaat   3600
tttattaata atctgcacag tttgttattg tgttgtacat aacaaccaac actttcctta   3660
tgctgttttt tttctaatct aattataaca taagagtttg gatgtaaact tggattgata   3720
gaaaacatca agtttggttt acatctggct tatttgatga ttgcaaattt ttgtttgtca   3780
gattaatttt agatactata catgttacgt attttacatc tttcgcctca ggagcactag   3840
ttattaagag acacatggaa gaagttcctt aataatctct ttgcatggcg ataatgacat   3900
atgatgtctt aaatgttatc ccctctccct ttatcaatct gcttgacaca atctgtttta   3960
ccttctggtt tagtatgaca caaagtacta ctatgaaatt ggaaaaggag attctgcacg   4020
gaagttttgg tttgaaactc ctccaaaagt tgatccagat gcttcttaca aatttggcat   4080
cataggtaag tagtttaaat ttctatttga taggttagct aagtaaattt ctttcgggtg   4140
ttttatcttt ttcagaagaa caggctgtat ccttgtaagt tgctataaga tgggttatac   4200
accataacat cacataactt cgctatgacg gaaatacagt ttatttgttt tcacaatata   4260
gaactgaaag aaaatgtata gaatggtaga gattaaaaag aacattagtt cctaactttt   4320
tcgttcatgg aagagcgatg agttttttct tggtaatgta acataaatcc aaccattcat   4380
aggaagcaaa attagaaagc tttgactctc ttttgaatag cgagtcagct atagtttctt   4440
atttgtttta ccgcatcttg atgtcactgc acctacttaa ctgtttcaca gttagaccaa   4500
tgacactgta tcataaagta ttaattattc acatactgta tgtgagccca tttggattaa   4560
ttgacagtaa atagctgatt aattttaagt gcttcaattt ttttttaaa tgctgaaact   4620
aattttacaa taagcaatta cgtgtttgga tagacgtgct gaaactatta ataagcaata   4680
gatgtgttag gtaaaaatgt gttgataagc tattcttatg ttagattgat caaaatacct   4740
ttaacatttt tgcaaaacat atatatgtga aattatcgta aagaaaagga ggaaccaaga   4800
atacagagtg aagaacaagt taggagttct gttttggcaa agatttagaa aaatattaag   4860
gataaattag taaaatacat ggttaaaaca aaagtgctta taagctgaaa atctgtttgt   4920
tgggggtgaa cagcctatgg cttttggatg agtttagctt ataagcactt cagtatttac   4980
caagtgctta gcttataatc ttagccaaac acgctcatta ttgtgtcagg attcttatac   5040
```

```
agttcgtcca acatcctttg caggtgacct tggtcaaaca tataattctc tttcaactct   5100
tcagcattac atggctagtg gagcaaagag tgtcttgttt gttggagacc tctcctatgc   5160
tgacagatat cagtataacg atgttggagt ccgttgggat acatttggcc gcctagttga   5220
acaaagtaca gcataccagc catggatttg gtctgctggg aatcatgaga tagagtactt   5280
tccatctatg gtaatatatt gtaatacagc taatgacctt gcgtttattt caaaaagttt   5340
tttcgggtct ccttataatg tcagttaagt ggctacaacc taagtctctg actacatatg   5400
tagctactca gtagaatcat gcaagggtga ataaaatgga aaagaaaaaa aaaactgtct   5460
tctttaggtt aaaaaagaat tttaccttga tgtcatcttt tataatcaag gtcgctaaac   5520
ctagtaaatt tgtaacatgt gcagaagagg tttctacttg agacagttat ctcgttgtac   5580
tactgcttcc tgtaaaagtg agattacgtg tctgagatat cagtacatgt tgaagattct   5640
agtagccaca agcacgccat tcacttgaac caaagatgaa ctgaagatat tctgtgctta   5700
tgcagaacat tgactttctc tcacagtctc agatggaccc aaggccgtga tggctagatt   5760
tgcaaaagca tgatctctaa ttctaatgta gaaatatttc cattttcatt tctagacctc   5820
caatgtctct tgtactccga ttatcacact attttattgt agttactgtt ccttttcctg   5880
aatgttttgt catgctttct atagtatttt gccatgattt cttcacttcc attatttctt   5940
tttcgatctg cttttatatc cctttccttg agtcgagggt ctatcataaa caacatctct   6000
acctcgcatg gtagggataa ggtcttcgta cactctaccc tccccagacc ccactcgtgg   6060
attacactag atatgatgtt cttgttgtac atcttgacct ccaatgtgct tggggctttg   6120
tgagcaatgt cttgaaatgt actgacttaa tcaaaataaa atagaactcc accaatgagt   6180
catgtaaaat ttctcccatc ccaaggaact ttgtattaag ttcattcaaa atattttgat   6240
gcccattaac tatatttatc attatgtaca gggggaagta gttccattca gatcgtttct   6300
atctagatac cccacacctt atcgagcttc aaaaagcagt aatccccttt ggtatgccat   6360
cagaagggca tctgctcaca taattgtcct atcaaactat tccccttttg gtaagtaatt   6420
gttccctctc ttatgcttgt tttcttttgt ttctctaact agttctagac actaatttga   6480
tgatctagtt ctgaaaaatc tactagcttg tgctaaaact tgagtaaatt gaagattttg   6540
caaaactata cacctaacga caaatagaac caccacaaac taaaaatcag gattctgaaa   6600
tgtacaaatt ttctaatttc agaagactta aagaagtttc aatgagttga tccgcacact   6660
agacatgcta acagtacttc gttaaatctc ctcattgtga tttgaaaaaa tatttgtcaa   6720
aaaaaggggt gcctaagact tggtttattt tttggacttt gcagttaatt agccagctaa   6780
catacagtgt taactgttaa gatagaaggc gttatctcac taatgaactt ttttaaaaaa   6840
aacatcatgt aatcaactaa gtatatgcat ctataagtta aaattctcaa actcatgctc   6900
actagctttt gcattgcagt gttgctaaga agatgtataa tattctgttt gctaattgtg   6960
ttcttgattg ccaattattc gttcctttac tgccgaacga tgtccatatg gaaggaagaa   7020
agttttcctg taattatttg gtgcatttgt ccggggaaac tcgtacaggt ctcttcaagt   7080
tccggagagt aatttctcac ggttttctaa aagcagagca caagctttag ggcctagctt   7140
tgaattttat agaaatctga gaagtacttt tgcttttgtt gagaaagtta actgatatta   7200
taaacagaga agtagagggt ttgtcaaaaa gaatctaaac acatatctcc ctcgtaaact   7260
atctaagaat agctaatacg ccacaatggc attggctgaa acaggaattt aaaaaggtga   7320
acagagagaa aactccttgg cttatagtcc ttatgcatgt tcctatctac aacagtaatg   7380
cagctcattt catggaaggg gaaagcatga gatccgccta cgaaagatgg tttgtcaaat   7440
```

```
acaaagtcga tgtgatcttt gctggccacg tccatgctta tgaaagatca ttgtttttttg   7500
cacatcgtca cccgttagtt ttgtttgata aaacttggag taacagaggg ggttgaggta   7560
tcgtgtaacg tttcgatact taccttcatg ttgaagtttt cgactttgtc gcttttaata   7620
gcctctttat ctcagttcaa aaccatggct gttcagctgt tgttagtagt ttctgaaatg   7680
ttacgtgttc agtgtatgcc taggaagtag aaggtccgtc atttgtgttg tcgtcggttt   7740
ccaaatataa aaagtactag tttactttcg aggaacaagg acagttacgg aaaacagggg   7800
gtgaagttct cggtttttct ccgggttagt taacatctgg tacatgaagc cacaacgtga   7860
cttgaagact atgggaaact actgaaataa ctgtcgtaga tttttcagaa agaggcactg   7920
tcaaaaggag gagcgagctt atcgtatgta aggtcgaagg cacgtgtgtg aagactacag   7980
tcgaggacat ctcaatcctg tctcagcccg gttctcaagt ttggcttata gggcgagctg   8040
tcagtaacag gcacacactt agaacttata gacacaagat gagaggttta gttatcgcat   8100
atctaatata cactacaatg tctcgggtgg tgatgcttat cccgtaccag ataaggcagc   8160
tcctatttac ataactgttg gtgatggagg aaattcagaa ggcctgactt caagaacgtg   8220
gaggttaccg tagatgaagc agctttttgt gttacgtccg gaagaacctc gctcggtgaa   8280
gtagaccttg tcaagtgctt ggtaagatcg ggggagtggt tgtataaaga cttgttcgag   8340
tgatggttat tgtgcttact tcgtacgtag gcatgctaaa cgttgtcgag accgttcgtt   8400
acaaaagggt cacggtcctc ctggtatcgt ctcttgtggc catcccccta gttaaggttc   8460
aaactgttta aaaagtccca cttcgtaccc ttcaagttgt tggagagcgt agaagagtta   8520
aacaagaaat gtaggaggtt gtagtaatat acattgtagt ccaaaaagga gctgtcagta   8580
gtaacactgt gaacctagtt aaaacccccc gttgccttag acttaaacta taaataagga   8640
tagttgcggc tgagagtacg gaagaagata tagtcaacca ctttgaaata gtggattagg   8700
ttgttgtttg aatcgttaaa cgaactgtaa atattgtata aaacgtagaa gtcataaccc   8760
cgattaatag aaacatgtgg atcggtggac ttctccaacc aagaggacgt agtagacaaa   8820
tagactttga tctagggtga ctgaaccatg tcggttgggt cacagtctaa ggaattatgg   8880
tgcgtttagt aaatagaaaa aacggtaaag gaactaaagg aagagtcgaa agaaatacga   8940
acaccttatt ccggggtttg gcattcagaa ctcatctcgt tatagtagaa gtagttctcc   9000
ggatcccaag aagagcagga attagagtag tttagagatc cccagccaga atattctgcc   9060
tttagagaag cgtcatatgg gcatgctata ctggaaatta agaacaggac tcacgcatac   9120
tatagctgga atagaaacga tgatggtaac gcaattacaa ccgattcatt tacgcttcat   9180
aaccagcatt ggtagaacat gttagtcaaa ctatgggtaa tttttatgac atgatcctag   9240
tatgtagtta tattgtaaaa tctatctact tttgttggag agagtggatc aagctatttt   9300
accagtgtat ctgttcacgt aaaataagga tttgtgccgt ttatatgaca gcattatgga   9360
aagtatagct cttgtaaatt tgaaatagct acttcatatt agattttcat tg            9412
```

```
<210> SEQ ID NO 2
<211> LENGTH: 3981
<212> TYPE: DNA
<213> ORGANISM: SOLANUM TUBEROSUM

<400> SEQUENCE: 2

ggtgacacta tagaagagct cgaggatcgt atttcctgga tgcctatata tagaagctac     60
tactcttgat taatgtgaaa gttgagtttt cccacaagat gggtgtgttt ggttattgca    120
ttttcgttgt tctaagtttg attgtgaatg agtcagtttt atgccatggc ggagtcacca    180
```

```
gtagttttgt taggaaagtt gagaagacaa ttgatatgcc tctggatagt gatgtcttcc    240
gtgttcctcc tggatataat gcgcctcaac aggtatcttc atattctcat tccaaggaga    300
caggtcggaa tgtatgggag taggtttgcc tctcgagtct cgtcctacaa atgaaaggcc    360
tcccacaggg tgcttagtag ctagtttatg ttagctgctt attcttgacc aagttattag    420
tgaagaaact ctcttgtcaa aattttattg tgaaaaatac tgccagtgtt taaatttttt    480
atcacatgta ataagctttt acttatgctt gtcactttca tggaatttgg tttatttgac    540
aattgattct atttggggtt tctttataag gttcatataa cacaaggaga tcacgtggga    600
aaggcggtaa ttgtttcatg ggtgactgtg gatgaacctg gttcaagtac agtagtatac    660
tggcgtgaga aaagcaagct aaagaataag gccaatggaa aagttactac ctataagttt    720
tataactata catctggtta catccaccac tgtactatcg aacatttgaa ggttaaacat    780
tctttctttc attccttgaa caaaatttag tattggggat gctcaaattg acaatggatt    840
taattctcct tttgtagttc gataccatat actactataa gattgggatt gggcacgtgg    900
cacgaacctt ctggttcgta actcctccag aagctgggcc tgatgtaccc tatacatttg    960
gtcttatagg taacaattcc aaccatatta ttgctgttgg agctttctta ggttatttta   1020
ccattgcttt tgaggtttca tttatattgt gctttcattt gtgtggtgtt tattagtcaa   1080
tcctgcattt cattacaggg gatcttggtc agagtttcga ttcaaacaag acactcacac   1140
attatgaatt aaatccaatt aaggggcaag cagtgttgtt cgtaggggac atatcttacg   1200
cagataagta tccaaatcat gacaataaca gatgggatac ttggggaagg tttgcagaga   1260
gaagtactgc ttatcaacct tggatttgga ccgcaggaaa tcatgagata gattttgctc   1320
ctgaaattgt aagtgatacc gtaatattag ctcattgaga tttaatgcat ttctgaattt   1380
tagatggttt tggaatggaa ttttgatgaa tatattttgt tactatctgc agggggaaac   1440
agaacccttc aagccctaca ctcatagata tcatgtcccg tataaagcat caaacagcac   1500
atctccactt tggtattcaa tcaagcgagc ttcagcatat atcatagttt tatcctcata   1560
ctcggcacat ggtaaggata tgacattctt gcgagtacta cttaacaact taatcgatgg   1620
tcacgtactt caacagcatt gataattcat aatgcatttt ctcggtgact tgaaggcgat   1680
tcggaaaatt caggacttgt ggatttgtct gtttttctta cagttccatt tgttcttttc   1740
aaattttagg caaatacact cctcaatata aatggctaga gaaagaacta ccaaaggtta   1800
acaggaccga gactccgtgg ctgtttgttt tagtacattc tccatggtat aacagctaca   1860
acaatcacta tatggaaggg gaaaccatga gagtagtgta tgagccatgg tttgtacagt   1920
acaaagtaga tatggtgttt gcaggtcatg ttcatgctta tgaacgaacg gtatgtacaa   1980
ctcaaccagt tctctgtagc ttatgtgaga atcatagttt catctgttat agaagatgaa   2040
atttttattg tgtttcagga acggatatct aatgtggcct ataacgttgt caatggagaa   2100
tgcagtccta ttaaagatca atctgctcca atttatataa caattggcga tggaggaaat   2160
cttgaaggcc tagccaccaa gtaagactaa tcgtctatgt ctagaaagtt gttttatctg   2220
ttgtaattgg caatttgtca gacaaataat cgcatatctt gtacactaat ttcagcatgt   2280
cagagccaca accagcttac tcacgtttcc gcgaggccag ttatggtcat gccactctcg   2340
ccatcaagaa tagaactcat gcttattata gttggcatcg taatcaagat ggatatgctg   2400
tggaagctga taaaatatgg gttaataatc gtttttggca cccagttgat gagtccacaa   2460
cagccaaatc agggtgatat acacgagatc tcatctttct tttctttcct ttttcctatg   2520
tagcattctg taattttgtt tccttacaag gtacacgtaa tgagacaatt agcatttaca   2580
```

```
cttgtatgtt gttgtatgta tatttcctaa tgagagatat agctgcaaaa ccagccagtg   2640
gactatacag ttttcatatg caactgatac acagaatatg ttgaacaaaa aattaccctg   2700
caaggtatag aaggtaacat caaagtacaa atgtgaaccg atttttcccc ccatgaaatt   2760
caagtattac tttatgcata tgtaatgagt tacaatatga cggactattt catcttttac   2820
accattaaca tcgtaaaaca ttggcatttg aaagtacctt ttttgaacca atcttcacaa   2880
caattgaaca tttcactttt agttaattca atgattcaaa aaaaggttta aacaaaaaata  2940
ataatttact tgctagcttc ataataacaa aatatacctt aggtaggtgg cgtttaggtt   3000
agttctaagt ttaactctga gataattaat ttaaggtgtc aattttaaga caattgttgt   3060
ctagatttaa ttttggaaga acaatttcat aaaagtaata atattttgaa aagtaatatt   3120
aaaatccaaa aaccaaataa atgctttcta attagtgaag tcgaagcaaa tgaaatatag   3180
aagaaaagac agaaaataaa agttggaatg agttttaggg gatgaaacag gtttctaaaa   3240
tcaatcgtgc tctttaatct ataaatttat ataactcgat ggaatcttta tatagtaaat   3300
attgagtcgt attctagctt aataactact tcaccactcc atatattact ttctttttat   3360
tgaaatgaaa aatggcattc aacttatata aattcatttc ttctttctag tctaatttaa   3420
ctatagatgt aatttgggac agctagaaag gcttgttcgc agtacttttg gtatgggaaa   3480
aaataaaaac gaattttatg ggaagaaagt ggaaaaatca aaaggagaag ggtgtttctc   3540
gtaaagcatt atagtttcgg ggaggaaatg acaaaaatag aaagaacagg gagttactcg   3600
ccacaaactt tatataagat gcaccgtcac caaaaaatgg cgcaggagac ggaaactact   3660
caattgcaca ttcgccttag tcgtcacaat tcacattttg gcaactccgt tttcagccat   3720
cgccgagaga aaaaataata atttcaaaag cgcttcctcc acgatctggt tgccggagga   3780
ggcgattttt tgaatgaaga gttcacctga attttctcga aatggctgaa tcgacgacaa   3840
ttcagaggag ctcgcctgaa ggtgatgatc atgaactgaa ggaggagaat attgagaaga   3900
aaaaggattt tactgcaaat cctgagttct tcagttgtat gcttcagcca gcgcctgccg   3960
attcagatcc aaattacatt g                                            3981
```

<210> SEQ ID NO 3
<211> LENGTH: 1751
<212> TYPE: DNA
<213> ORGANISM: SOLANUM TUBEROSUM

<400> SEQUENCE: 3

```
ccaaaggtta acagaactga aactccgtgg ctaattgttc tgcttcactc tccatggtac     60
aacagtaaca actatcatta catggaaggt gaaagcatga gagtgatgtt cgagtcctgg    120
tttgttcaga acaaggttga catggtgttt gcaggacatg ttcattctta tgaacgctcg    180
gtaggcccct caactccatc ctataaaatt tcatccttga accaatgtgt ataggtcttg    240
attaatggta tatatgtcac atggacaatt tcgtaggaac gagtatcaaa tgttatgtac    300
aacatcacaa atggacagag tactccaatt gaagatcctt ccgcgcctat atacataaca    360
attggggatg gtggaaatat tgaaggcatt gctaacaagt tagacttcta ttcgttctga    420
tctcattttt atttaatctg atgtaatgag aagagtatct gatgggagtc tgtctggttt    480
ttgtttgtgc agttttacag aaccacagcc gagctactca gcttatcgtg aagcaagttt    540
tggtcacgcg attcttgaaa ttaagaacag aactcacgcc tattatactt ggcatcgtaa    600
ccaagacagt gaacgagttg cagcagattc tttgtggatt tacaatagac actggtatcc    660
taaaaaggaa accagctcta tggcttgaaa gtaacatgtt tggtaggcag tgcagttgtt    720
```

```
atttcctag aaaccatgtg ttctattaga ttagttcgtc gggtactaaa ccagttccca    780
tttatgattt cttaaagacc tgtaagagga aaatgtgaca actaatatgg aacgaagaga   840
gtatacctta acccttagta ggtggaagtt tattttctta tgccttctcc aatcttagta   900
cttatttttt ttctttcaac ttcttaatat attttttttc cgaacttcaa ttttcaaata   960
ttcttttttt ctttttcatc tttaaccaaa taaaactctc ctccactatt aaatataact  1020
ggcagtgtca catcaagtca ttatctataa cactagaaat agataaatat aacatcaatt  1080
ttaggtttga aggttcatta tcatcaacac taattccata taaattcagt atgtattaca  1140
ggttacttct gtccaatgcc ataagatgta ataaatatac atgaaaatga acttcactta  1200
tttatgcctt taattaatag attctctaaa tacaaagtac cttccaaaat attagccaac  1260
agaaaattaa aatcttttgc ccctctttgg ctcgtctagt cttcactata aattgaccat  1320
ttgtaactat aatcttcatc ccccctcact actctttagc taagtgttct ttctttttat  1380
tcctttgtgt ttttctcaat cctaagaatt tgtcatttct ttatattatt ggtttttaag  1440
ttacatacac tgatatgagt tggcttcaa gaaaaggcga aaaatttata tagccaacca   1500
ggcaaccaca actcgtttgt gacttaggtg taggttgttg ttgttgttgt tgttaagtta  1560
catacattaa caacataaat attttttat gctatcggta tagtttattt gataacgtaa   1620
atatttacaa acaagatttg gttgaggatt caaagtgaga aattctattg acagaagaga  1680
gagagtacaa tctgtcatca gcaaaatgat attgttgttt gttggaatgt actctctctg  1740
cttctgccaa t                                                       1751
```

<210> SEQ ID NO 4
<211> LENGTH: 2048
<212> TYPE: DNA
<213> ORGANISM: SOLANUM TUBEROSUM

<400> SEQUENCE: 4

```
actcgatcca tttattagga tacatgtact gcactagtaa gattttagaa cacttacaaa    60
tacgtatgta ctataaacat attgggatac ttggagcaac gatcaagttg tccccgtgtg   120
acctataggt catgagtttg agctgtgaac tcagtaactg atccttgcat tagtgtatgc   180
tttctacatc acacactccc ttgtggtgtg gcccttcctc ggaccctgca taaacatgtg   240
atgtttcgtg caccgtgctt atgtgcttca actaccttat aacttcttaa attgctctag   300
aacaaaagat tcatttgttt atttctgcag atttagagat cctcaaccag attactctgc   360
gttccgcgaa tccagttatg gtcattctac actagagatt aagaacagaa cacatgcatt   420
ctaccattgg aacagaaatg acgatggaaa gaaggttaaa atcgattcat tcgtgttaca   480
caatctgtac tggtcagtat gatcttcctc cctctgcaga atatatttca tctggagaat   540
ctgaattgaa ttttctttta acttactgta gtagataatc tgtcttattt tccgaggact   600
aatctcactc actatggatg agtatcatta gttatcattt aggcgaattt ttcacattgt   660
cagtatatag aggttaaact cacgcgattt atggtcatgc aggggacaga atcatcacca   720
gagagagacg aaacaaaatc gtctccgttc acatcatttt aaacagggct tcaactgcac   780
aactgtgaga acatatttct gcaacttact ctcaacttag ttgcagtttt atggccatat   840
agattaatat cccaatggca actaataagt ttgaatatct atttgctctc ttcggactat   900
ttggcaaatt acttgagccg agggttatca aaaaacgtgt gcgtacacac tacctttcca   960
gaccttagtt gtgggattat acggggtatg ttattggact atttggctaa atttccacca  1020
aatatttatc attcaaataa gagtttgtgc tgttcactgc atcatttcag tttctgaaga  1080
```

```
attattttat ttgaatattc acaatgcatt tacttaattt attttattct agttttggaa   1140

gatgaatgtt ccttcagaat atttaatagg ctagttttta gtttttcttt tgagaaaaat   1200

cttacccgcc atcaaaggtt gtggtgaagc aataaatact cattcaccct taacaaaagg   1260

tctcggattt gacctatgga tatggagtct tctttgataa ggagtgtttt actcccctaa   1320

agtgaaactt tccagcatga atccgaatta gtcagaccca aagcaggtat cgagtgggaa   1380

accaaaaaag aaaaaaatct acttttagat gagatgatcc atcacacttg gtatcatagt   1440

aggcagaggt ccctagtttg agtctctatt ccaaccatta tcaaaacaaa gaaaattcac   1500

atccttggcc attaaaaacg aatcaagctc acacacgaga ggttgtgtcg aagacatcat   1560

tgggtaaata aaaatgtgct cagatagtca cacacttcaa cgaatgaaaa attgtctata   1620

tagccaaggc taaaaagaga gttgctagta gtacatataa cttcaactag aaaaattact   1680

caatttttat tcttgtccag cttcaacttc agcttctctt caaaagtttc acaactttac   1740

agtatctctc ttctgttatt attaaatcat gtacagaaat attcgattat acgtgctgtc   1800

gttcccagtc tattaggaat caaagaaatt tactccctgt acaaaactaa caagaatgta   1860

aaactgaagt ttgatgttca tcattggtag tctctgtata ttggctgtgg attccatttg   1920

agatgcaagt tcagtttccc tgatttagcc tcggctaatt cgtacgtgtc tttgtattca   1980

ccttccatta gaacccttgt taaagtcagt atgcatcttc ccatgaaatc ctgtgaagaa   2040

agttggaa                                                            2048
```

```
<210> SEQ ID NO 5
<211> LENGTH: 1160
<212> TYPE: DNA
<213> ORGANISM: ORYSA SATIVA

<400> SEQUENCE: 5

atcaacataa tgatggtgtt cgttgggatt cttgggggcg gcttgtggaa cgtagtaccg     60

cttatcaacc atggatttgg agcgctggta accatgaaat tgaatacagg cctgatctgg    120

gagaaacttc tacatttaag ccatatctgc atagatgtca cactccatat ttggcatcaa    180

agagcagttc tcctatgtgg tatgcagtca gacgtgcatc tgctcatatc attgtgcttt    240

ctagctattc tccattcgta aaatacactc ctcaatggac ctggttgaag tatgaattga    300

agcatgtgga tagagagaag actccttggc ttattgttct catgcattct cccatgtaca    360

acagcaatga agcacattac atggagggtg agagtatgag ggctgctttt gagaaatggt    420

ttgtgaagta caaggttgac ttggtatttg cagggcatgt gcatgcttat gagagatcgt    480

atcgtatctc taacatcaac tacaacataa catcgggtaa tcgatatcca gtgccagaca    540

aatctgctcc tgtgtacata acagttggtg atggaggcaa ccaggaaggg cttgcttcaa    600

ggttcagtga tccacagcca gactactctg cattcaggga ggctagttat ggtcattcga    660

tcttgcaact gaaaaacagg actcatgcta tctaccagtg gaatagaaac gatgatggga    720

agcatgtacc tgcggacaat gtggtgtttc acaaccagta ttgggcaagc aacactcgcc    780

gcaggaggct gaagaagaag cattttcact tggatcaaat tgaggacttg atatccgtgt    840

tctagagtga tctttcagaa cacgcatcgc agactttctg aaacggtggc ggaatagctc    900

tgttgccctt tggtcttgag cctcgaccga gtgaggcaga ggctctcggc tctcatgtaa    960

aggaaccatg cacaggtttg tgggattact attattgagc actgtattgt atgatgaaga   1020

caatccgatc agcagatgat tagtgctgta cacatgtagc atttcacagc cagcgacagt   1080

ttcgcaatgt gacagtatct tcaataaagt ttcaaagggt tgtgaaccga gattgcagca   1140
```

```
ttagctgccc tctgttcgta                                                 1160


<210> SEQ ID NO 6
<211> LENGTH: 412
<212> TYPE: PRT
<213> ORGANISM: SOLANUM TUBEROSUM


<400> SEQUENCE: 6

Leu Glu Asn Glu Val Leu Ser Val Pro Asn Gly Tyr Asn Ala Pro Gln
 1               5                  10                  15

Gln Val His Ile Thr Gln Gly Asp Tyr Asp Gly Glu Ala Val Ile Ile
            20                  25                  30

Ser Trp Val Thr Ala Asp Glu Pro Gly Ser Ser Glu Val Arg Tyr Gly
        35                  40                  45

Leu Ser Glu Gly Lys Tyr Asp Val Thr Val Glu Gly Thr Leu Asn Asn
    50                  55                  60

Tyr Thr Phe Tyr Lys Tyr Glu Ser Gly Tyr Ile His Gln Cys Leu Ile
65                  70                  75                  80

Thr Gly Leu Gln Tyr Asp Thr Lys Tyr Tyr Tyr Glu Ile Gly Lys Gly
                85                  90                  95

Asp Ser Ala Arg Lys Phe Trp Phe Glu Thr Pro Pro Lys Val Asp Pro
            100                 105                 110

Asp Ala Ser Tyr Lys Phe Gly Ile Ile Gly Asp Leu Gly Gln Thr Tyr
        115                 120                 125

Asn Ser Leu Ser Thr Leu Gln His Tyr Met Ala Ser Gly Ala Lys Ser
    130                 135                 140

Val Leu Phe Val Gly Asp Leu Ser Tyr Ala Asp Arg Tyr Gln Tyr Asn
145                 150                 155                 160

Asp Val Gly Val Arg Trp Asp Thr Phe Gly Arg Leu Val Glu Gln Ser
                165                 170                 175

Thr Ala Tyr Gln Pro Trp Ile Trp Ser Ala Gly Asn His Glu Ile Glu
            180                 185                 190

Tyr Phe Pro Ser Met Gly Glu Val Val Pro Phe Arg Ser Phe Leu Ser
        195                 200                 205

Arg Tyr Pro Thr Pro Tyr Arg Ala Ser Lys Ser Ser Asn Pro Leu Trp
    210                 215                 220

Tyr Ala Ile Arg Arg Ala Ser Ala His Ile Ile Val Leu Ser Asn Tyr
225                 230                 235                 240

Ser Pro Phe Gly Lys Tyr Thr Pro Gln Trp His Trp Leu Lys Gln Glu
                245                 250                 255

Phe Lys Lys Val Asn Arg Glu Lys Thr Pro Trp Leu Ile Val Leu Met
            260                 265                 270

His Val Pro Ile Tyr Asn Ser Asn Ala Ala His Phe Met Glu Gly Glu
        275                 280                 285

Ser Met Arg Ser Ala Tyr Glu Arg Trp Phe Val Lys Tyr Lys Val Asp
    290                 295                 300

Val Ile Phe Ala Gly His Val His Ala Tyr Glu Arg Ser Tyr Arg Ile
305                 310                 315                 320

Ser Asn Ile His Tyr Asn Val Ser Gly Gly Asp Ala Tyr Pro Val Pro
                325                 330                 335

Asp Lys Ala Ala Pro Ile Tyr Ile Thr Val Gly Asp Gly Gly Asn Ser
            340                 345                 350

Glu Gly Leu Thr Ser Arg Phe Arg Asp Pro Gln Pro Glu Tyr Ser Ala
        355                 360                 365
```

```
Phe Arg Glu Ala Ser Tyr Gly His Ala Ile Leu Glu Ile Lys Asn Arg
    370                 375                 380

Thr His Ala Tyr Tyr Ser Trp Asn Arg Asn Asp Asp Gly Asn Ala Ile
385                 390                 395                 400

Thr Thr Asp Ser Phe Thr Leu His Asn Gln His Trp
                405                 410


<210> SEQ ID NO 7
<211> LENGTH: 466
<212> TYPE: PRT
<213> ORGANISM: SOLANUM TUBEROSUM

<400> SEQUENCE: 7

Met Gly Val Phe Gly Tyr Cys Ile Phe Val Val Leu Ser Leu Ile Val
 1               5                  10                  15

Asn Glu Ser Val Leu Cys His Gly Gly Val Thr Ser Ser Phe Val Arg
            20                  25                  30

Lys Val Glu Lys Thr Ile Asp Met Pro Leu Asp Ser Asp Val Phe Arg
        35                  40                  45

Val Pro Pro Gly Tyr Asn Ala Pro Gln Gln Val His Ile Thr Gln Gly
    50                  55                  60

Asp His Val Gly Lys Ala Val Ile Val Ser Trp Val Thr Val Asp Glu
65                  70                  75                  80

Pro Gly Ser Ser Thr Val Val Tyr Trp Arg Glu Lys Ser Lys Leu Lys
                85                  90                  95

Asn Lys Ala Asn Gly Lys Val Thr Thr Tyr Lys Phe Tyr Asn Tyr Thr
            100                 105                 110

Ser Gly Tyr Ile His His Cys Thr Ile Glu His Leu Lys Phe Asp Thr
        115                 120                 125

Ile Tyr Tyr Tyr Lys Ile Gly Ile Gly His Val Ala Arg Thr Phe Trp
    130                 135                 140

Phe Val Thr Pro Pro Glu Ala Gly Pro Asp Val Pro Tyr Thr Phe Gly
145                 150                 155                 160

Leu Ile Gly Asp Leu Gly Gln Ser Phe Asp Ser Asn Lys Thr Leu Thr
                165                 170                 175

His Tyr Glu Leu Asn Pro Ile Lys Gly Gln Ala Val Leu Phe Val Gly
            180                 185                 190

Asp Ile Ser Tyr Ala Asp Lys Tyr Pro Asn His Asp Asn Asn Arg Trp
        195                 200                 205

Asp Thr Trp Gly Arg Phe Ala Glu Arg Ser Thr Ala Tyr Gln Pro Trp
    210                 215                 220

Ile Trp Thr Ala Gly Asn His Glu Ile Asp Phe Ala Pro Glu Ile Gly
225                 230                 235                 240

Glu Thr Glu Pro Phe Lys Pro Tyr Thr His Arg Tyr His Val Pro Tyr
                245                 250                 255

Lys Ala Ser Asn Ser Thr Ser Pro Leu Trp Tyr Ser Ile Lys Arg Ala
            260                 265                 270

Ser Ala Tyr Ile Ile Val Leu Ser Ser Tyr Ser Ala His Gly Lys Tyr
        275                 280                 285

Thr Pro Gln Tyr Lys Trp Leu Glu Lys Glu Leu Pro Lys Val Asn Arg
    290                 295                 300

Thr Glu Thr Pro Trp Leu Phe Val Leu Val His Ser Pro Trp Tyr Asn
305                 310                 315                 320

Ser Tyr Asn Asn His Tyr Met Glu Gly Glu Thr Met Arg Val Val Tyr
                325                 330                 335
```

```
Glu Pro Trp Phe Val Gln Tyr Lys Val Asp Met Val Phe Ala Gly His
            340                 345                 350

Val His Ala Tyr Glu Arg Thr Glu Arg Ile Ser Asn Val Ala Tyr Asn
        355                 360                 365

Val Val Asn Gly Glu Cys Ser Pro Ile Lys Asp Gln Ser Ala Pro Ile
    370                 375                 380

Tyr Ile Thr Ile Gly Asp Gly Gly Asn Leu Glu Gly Leu Ala Thr Lys
385                 390                 395                 400

Met Ser Glu Pro Gln Pro Ala Tyr Ser Arg Phe Arg Glu Ala Ser Tyr
                405                 410                 415

Gly His Ala Thr Leu Ala Ile Lys Asn Arg Thr His Ala Tyr Tyr Ser
            420                 425                 430

Trp His Arg Asn Gln Asp Gly Tyr Ala Val Glu Ala Asp Lys Ile Trp
        435                 440                 445

Val Asn Asn Arg Phe Trp His Pro Val Asp Glu Ser Thr Thr Ala Lys
    450                 455                 460

Ser Gly
465


<210> SEQ ID NO 8
<211> LENGTH: 165
<212> TYPE: PRT
<213> ORGANISM: SOLANUM TUBEROSUM

<400> SEQUENCE: 8


Pro Lys Val Asn Arg Thr Glu Thr Pro Trp Leu Ile Val Leu Leu His
 1               5                  10                  15

Ser Pro Trp Tyr Asn Ser Asn Asn Tyr His Tyr Met Glu Gly Glu Ser
            20                  25                  30

Met Arg Val Met Phe Glu Ser Trp Phe Val Gln Asn Lys Val Asp Met
        35                  40                  45

Val Phe Ala Gly His Val His Ser Tyr Glu Arg Ser Glu Arg Val Ser
    50                  55                  60

Asn Val Met Tyr Asn Ile Thr Asn Gly Gln Ser Thr Pro Ile Glu Asp
65                  70                  75                  80

Pro Ser Ala Pro Ile Tyr Ile Thr Ile Gly Asp Gly Gly Asn Ile Glu
                85                  90                  95

Gly Ile Ala Asn Lys Phe Thr Glu Pro Gln Pro Ser Tyr Ser Ala Tyr
            100                 105                 110

Arg Glu Ala Ser Phe Gly His Ala Ile Leu Glu Ile Lys Asn Arg Thr
        115                 120                 125

His Ala Tyr Tyr Thr Trp His Arg Asn Gln Asp Ser Glu Arg Val Ala
    130                 135                 140

Ala Asp Ser Leu Trp Ile Tyr Asn Arg His Trp Tyr Pro Lys Lys Glu
145                 150                 155                 160

Thr Ser Ser Met Ala
                165


<210> SEQ ID NO 9
<211> LENGTH: 52
<212> TYPE: PRT
<213> ORGANISM: SOLANUM TUBEROSUM

<400> SEQUENCE: 9

Asp Pro Gln Pro Asp Tyr Ser Ala Phe Arg Glu Ser Ser Tyr Gly His
 1               5                  10                  15
```

```
Ser Thr Leu Glu Ile Lys Asn Arg Thr His Ala Phe Tyr His Trp Asn
            20                  25                  30

Arg Asn Asp Asp Gly Lys Lys Val Lys Ile Asp Ser Phe Val Leu His
        35                  40                  45

Asn Leu Tyr Trp
    50


<210> SEQ ID NO 10
<211> LENGTH: 281
<212> TYPE: PRT
<213> ORGANISM: ORYSA SATIVA

<400> SEQUENCE: 10


Asp Gln His Asn Asp Gly Val Arg Trp Asp Ser Trp Gly Arg Leu Val
 1               5                  10                  15

Glu Arg Ser Thr Ala Tyr Gln Pro Trp Ile Trp Ser Ala Gly Asn His
            20                  25                  30

Glu Ile Glu Tyr Arg Pro Asp Leu Gly Glu Thr Ser Thr Phe Lys Pro
        35                  40                  45

Tyr Leu His Arg Cys His Thr Pro Tyr Leu Ala Ser Lys Ser Ser Ser
    50                  55                  60

Pro Met Trp Tyr Ala Val Arg Arg Ala Ser Ala His Ile Ile Val Leu
65                  70                  75                  80

Ser Ser Tyr Ser Pro Phe Val Lys Tyr Thr Pro Gln Trp Thr Trp Leu
                85                  90                  95

Lys Tyr Glu Leu Lys His Val Asp Arg Glu Lys Thr Pro Trp Leu Ile
            100                 105                 110

Val Leu Met His Ser Pro Met Tyr Asn Ser Asn Glu Ala His Tyr Met
        115                 120                 125

Glu Gly Glu Ser Met Arg Ala Ala Phe Glu Lys Trp Phe Val Lys Tyr
    130                 135                 140

Lys Val Asp Leu Val Phe Ala Gly His Val His Ala Tyr Glu Arg Ser
145                 150                 155                 160

Tyr Arg Ile Ser Asn Ile Asn Tyr Asn Ile Thr Ser Gly Asn Arg Tyr
                165                 170                 175

Pro Val Pro Asp Lys Ser Ala Pro Val Tyr Ile Thr Val Gly Asp Gly
            180                 185                 190

Gly Asn Gln Glu Gly Leu Ala Ser Arg Phe Ser Asp Pro Gln Pro Asp
        195                 200                 205

Tyr Ser Ala Phe Arg Glu Ala Ser Tyr Gly His Ser Ile Leu Gln Leu
    210                 215                 220

Lys Asn Arg Thr His Ala Ile Tyr Gln Trp Asn Arg Asn Asp Asp Gly
225                 230                 235                 240

Lys His Val Pro Ala Asp Asn Val Val Phe His Asn Gln Tyr Trp Ala
                245                 250                 255

Ser Asn Thr Arg Arg Arg Arg Leu Lys Lys Lys His Phe His Leu Asp
            260                 265                 270

Gln Ile Glu Asp Leu Ile Ser Val Phe
        275                 280


<210> SEQ ID NO 11
<211> LENGTH: 1877
<212> TYPE: DNA
<213> ORGANISM: SOLANUM TUBEROSUM

<400> SEQUENCE: 11
```

```
aattaaatta accaacacac actcatcgaa ctgattaaga acaaatgttc ccttgaatat     60
tcatgttttt ttaaacttga tttgtagtag ttctactatt tcaattcaaa aaaatcatct    120
ttttgatata cccatttcaa aaaagattac atttttagtt cagaaatatc atagattttt    180
gctggttcac tcccttgttg tttcagcctt caaagtcaat tataactggt gttgcctgag    240
ttctctctga tcgagcagtg cttatcttgg aagttagtgg agaggagaca atgttgcttt    300
atatcttctt tttgttatct ctctttttga catttataga caatgggagt gctggtataa    360
caagtgcatt cattcgaact cagtttccgt ctgttgatat tccccttgaa aatgaagtac    420
tgtcagttcc aaacggttat aacgctccac agcaagtgca tattacacaa ggtgactatg    480
atggggaagc tgtcattatt tcatgggtaa ctgctgatga accagggtct agcgaagtgc    540
gatatggctt atctgaaggg aaatatgatg ttactgttga agggactcta aataactaca    600
cattctacaa gtacgagtcc ggttacatac atcagtgcct tgtaactggc cttcagtatg    660
acacaaagta ctactatgaa attggaaaag gagattctgc ccggaagttt tggtttgaaa    720
ctcctccaaa agttgatcca gatgcttctt acaaatttgg catcataggt gaccttggtc    780
aaacatataa ttctctttca actcttcagc attatatggc tagtggagca aagagtgtct    840
tgtttgttgg agacctctcc tatgctgaca gatatcagta taacgatgtt ggagtccgtt    900
gggatacatt tggccgccta gttgaacaaa gtacagcata ccagccatgg atttggtctg    960
ctgggaatca tgagatagag tactttccat ctatggggga agtagttcca ttcagatcgt   1020
ttctatctag ataccccaca ccttatcgag cttcaaaaag cagtaatccc ctttggtatg   1080
ccatcagaag ggcatctgct cacataattg tcctatcaaa ctattcccct tttggtaagt   1140
atacgccaca atggcattgg ctgaaacagg aatttaaaaa ggtgaacaga gagaaaactc   1200
cttggcttat agtccttatg catgttccta tctacaacag taatgcagct catttcatgg   1260
aaggggaaag catgagatcc gcctacgaaa gatggtttgt caaatacaaa gtcgatgtga   1320
tctttgctgg ccacgtccat gcttatgaaa gatcatatcg catatctaat atacactaca   1380
atgtctcggg tggtgatgct tatcccgtac cagataaggc agctcctatt tacataactg   1440
ttggtgatgg aggaaattca gaaggcctga cttcaagatt tagagatccc cagccagaat   1500
attctgcctt tagagaagcg tcatatgggc atgctatact ggaaattaag aacaggactc   1560
acgcatacta tagctggaat agaaacgatg atggtaacgc aattacaacc gattcattta   1620
cgcttcataa ccagcattgg tagaacatgt tagtcaaact atgggtaatt tttatgacat   1680
gatcctagta tgtagttata ttgtaaaatc tatctacttt tgttggagag agtggatcaa   1740
gctattttac cagtgtatct gttcacgtaa aataaggatt tgtgccgttt atatgacagc   1800
attatggaaa gtatagctct tgtaaatttg aaatagctac ttcatattag attttcattg   1860
tttgtattaa aaaaaaa                                                  1877
```

<210> SEQ ID NO 12
<211> LENGTH: 450
<212> TYPE: PRT
<213> ORGANISM: SOLANUM TUBEROSUM

<400> SEQUENCE: 12

```
Met Leu Leu Tyr Ile Phe Phe Leu Leu Ser Leu Phe Leu Thr Phe Ile
 1               5                  10                  15

Asp Asn Gly Ser Ala Gly Ile Thr Ser Ala Phe Ile Arg Thr Gln Phe
            20                  25                  30
```

-continued

```
Pro Ser Val Asp Ile Pro Leu Glu Asn Glu Val Leu Ser Val Pro Asn
        35                  40                  45

Gly Tyr Asn Ala Pro Gln Gln Val His Ile Thr Gln Gly Asp Tyr Asp
    50                  55                  60

Gly Glu Ala Val Ile Ile Ser Trp Val Thr Ala Asp Glu Pro Gly Ser
65                  70                  75                  80

Ser Glu Val Arg Tyr Gly Leu Ser Glu Gly Lys Tyr Asp Val Thr Val
                85                  90                  95

Glu Gly Thr Leu Asn Asn Tyr Thr Phe Tyr Lys Tyr Glu Ser Gly Tyr
            100                 105                 110

Ile His Gln Cys Leu Ile Thr Gly Leu Gln Tyr Asp Thr Lys Tyr Tyr
        115                 120                 125

Tyr Glu Ile Gly Lys Gly Asp Ser Ala Arg Lys Phe Trp Phe Glu Thr
    130                 135                 140

Pro Pro Lys Val Asp Pro Asp Ala Ser Tyr Lys Phe Gly Ile Ile Gly
145                 150                 155                 160

Asp Leu Gly Gln Thr Tyr Asn Ser Leu Ser Thr Leu Gln His Tyr Met
                165                 170                 175

Ala Ser Gly Ala Lys Ser Val Leu Phe Val Gly Asp Leu Ser Tyr Ala
            180                 185                 190

Asp Arg Tyr Gln Tyr Asn Asp Val Gly Val Arg Trp Asp Thr Phe Gly
        195                 200                 205

Arg Leu Val Glu Gln Ser Thr Ala Tyr Gly Pro Trp Ile Trp Ser Ala
    210                 215                 220

Gly Asn His Glu Ile Glu Tyr Phe Pro Ser Met Gly Glu Val Val Pro
225                 230                 235                 240

Phe Arg Ser Phe Leu Ser Arg Tyr Pro Thr Pro Tyr Arg Ala Ser Lys
                245                 250                 255

Ser Ser Asn Pro Leu Trp Tyr Ala Ile Arg Arg Ala Ser Ala His Ile
            260                 265                 270

Ile Val Leu Ser Asn Tyr Ser Pro Phe Gly Lys Tyr Thr Pro Gln Trp
        275                 280                 285

His Trp Leu Lys Gln Glu Phe Lys Lys Val Asn Arg Glu Lys Thr Pro
    290                 295                 300

Trp Leu Ile Val Leu Met His Val Pro Ile Tyr Asn Ser Asn Ala Ala
305                 310                 315                 320

His Phe Met Glu Gly Glu Ser Met Arg Ser Ala Tyr Glu Arg Trp Phe
                325                 330                 335

Val Lys Tyr Lys Val Asp Val Ile Phe Ala Gly His Val His Ala Tyr
            340                 345                 350

Glu Arg Ser Tyr Arg Ile Ser Asn Ile His Tyr Asn Val Ser Gly Gly
        355                 360                 365

Asp Ala Tyr Pro Val Pro Asp Lys Ala Ala Pro Ile Tyr Ile Thr Val
    370                 375                 380

Gly Asp Gly Gly Asn Ser Glu Gly Leu Thr Ser Arg Phe Arg Asp Pro
385                 390                 395                 400

Gln Pro Glu Tyr Ser Ala Phe Arg Glu Ala Ser Tyr Gly His Ala Ile
                405                 410                 415

Leu Glu Ile Lys Asn Arg Thr His Ala Tyr Tyr Ser Trp Asn Arg Asn
            420                 425                 430

Asp Asp Gly Asn Ala Ile Thr Thr Asp Ser Phe Thr Leu His Asn Gln
        435                 440                 445

His Trp
    450
```

<210> SEQ ID NO 13
<211> LENGTH: 525
<212> TYPE: DNA
<213> ORGANISM: SOLANUM TUBEROSUM

<400> SEQUENCE: 13

```
aaaatagaaa aagtcttctt gtccgacata ggaacactca acgattttct acccaatatg     60
tggttttgta gtgtattgaa gcgatactgc ctttatgtca aataaacaaa agtgttatat    120
cttgactttc ttttacatat cttaccatct ctaatttttc ttgtaatcaa ggattgaaaa    180
agcaagtacc ttctcgctac tcaaaaaaga accattcatt gtatttaggt tggtagaatt    240
ccaagctgtt tcctatgcag aagttttgct tagggatggc aaggggagcc ttaacacgca    300
aattttcaac ccgggccaca tgagtttctt catgtcactt cttctttata atatgaagat    360
atgtgatgca gcattgaatg gactagatta gagcttagct ttttttttc ttatttcatt     420
ttttctacta tatataatgc aagagctgta aattttttgt gcattgcctt ttcactggct    480
cataatgttg agagaattgg atccaaatct gtactgtact atttt                    525
```

<210> SEQ ID NO 14
<211> LENGTH: 622
<212> TYPE: DNA
<213> ORGANISM: SOLANUM TUBEROSUM

<400> SEQUENCE: 14

```
ataaaatcaa ctctatgcca cctaattaca cattttgagg ccctttccaa ggtcatatgt     60
atttgcagag gaaggaagtc atctttggta gggagcactt acccctatag caagactttc    120
cggcatgagg attagtcacc gccaaaagtg gacaccggac atcaggtcaa ggaaaaccac    180
atatatcttt gagaatacca ttgtccatct agtacataaa ttggtgtaaa atagtaatct    240
ctgtcgtaat aaattatgaa agagaattga caagattctt aaacttactt cagaaaacac    300
aggaatctct tgtacgagaa aagaagatag tgaacgaatt cttcgaaggt ttggtttcaa    360
tgatttttca tttgattcgt aatattaatc atgttagtag cacagattca atcatttgat    420
accttttact tatatcgaga ttggatcaga tgtatttttt ttggattaca ttgatacttt    480
tggtgaatgg gcctgcattg ggtggatgta gatacagagt attgatatgt gatatcatcg    540
actcaactag tttaggattg aagtatagtt ggttgattcc ttgatattga ggtaatcaga    600
atattaacat gatatagtag ga                                             622
```

<210> SEQ ID NO 15
<211> LENGTH: 1236
<212> TYPE: DNA
<213> ORGANISM: SOLANUM TUBEROSUM

<400> SEQUENCE: 15

```
cttgaaaatg aagtactgtc agttccaaac ggttataacg ctccacagca agtgcatatt     60
acacaaggtg actatgatgg ggaagctgtc attatttcat gggtaactgc tgatgaacca    120
gggtctagcg aagtgcgata tggcttatct gaagggaaat atgatgttac tgttgaaggg    180
actctaaata actacacatt ctacaagtac gagtccggtt acatacatca gtgccttgta    240
actggccttc agtatgacac aaagtactac tatgaaattg gaaaaggaga ttctgcccgg    300
aagttttggt ttgaaactcc tccaaaagtt gatccagatg cttcttacaa atttggcatc    360
ataggtgacc ttggtcaaac atataattct ctttcaactc ttcagcatta tatggctagt    420
```

```
ggagcaaaga gtgtcttgtt tgttggagac ctctcctatg ctgacagata tcagtataac    480

gatgttggag tccgttggga tacatttggc cgcctagttg aacaaagtac agcataccag    540

ccatggattt ggtctgctgg gaatcatgag atagagtact ttccatctat gggggaagta    600

gttccattca gatcgtttct atctagatac cccacacctt atcgagcttc aaaaagcagt    660

aatccccttt ggtatgccat cagaagggca tctgctcaca taattgtcct atcaaactat    720

tccccttttg gtaagtatac gccacaatgg cattggctga aacaggaatt taaaaaggtg    780

aacagagaga aaactccttg gcttatagtc cttatgcatg ttcctatcta caacagtaat    840

gcagctcatt tcatggaagg ggaaagcatg agatccgcct acgaaagatg gtttgtcaaa    900

tacaaagtcg atgtgatctt tgctggccac gtccatgctt atgaaagatc atatcgcata    960

tctaatatac actacaatgt ctcgggtggt gatgcttatc ccgtaccaga taaggcagct   1020

cctatttaca taactgttgg tgatggagga aattcagaag gcctgacttc aagatttaga   1080

gatccccagc cagaatattc tgcctttaga gaagcgtcat atgggcatgc tatactggaa   1140

attaagaaca ggactcacgc atactatagc tggaatagaa acgatgatgg taacgcaatt   1200

acaaccgatt catttacgct tcataaccag cattgg                             1236


<210> SEQ ID NO 16
<211> LENGTH: 19
<212> TYPE: DNA
<213> ORGANISM: SOLANUM TUBEROSUM

<400> SEQUENCE: 16

ctctcggcga tggctgaaa                                                  19


<210> SEQ ID NO 17
<211> LENGTH: 21
<212> TYPE: DNA
<213> ORGANISM: SOLANUM TUBEROSUM

<400> SEQUENCE: 17

ttaagctaga atacgactca a                                               21


<210> SEQ ID NO 18
<211> LENGTH: 24
<212> TYPE: DNA
<213> ORGANISM: SOLANUM TUBEROSUM

<400> SEQUENCE: 18

taacctaaac gccacctacc taag                                            24


<210> SEQ ID NO 19
<211> LENGTH: 20
<212> TYPE: DNA
<213> ORGANISM: SOLANUM TUBEROSUM

<400> SEQUENCE: 19

tactttgatg ttaccttcta                                                 20


<210> SEQ ID NO 20
<211> LENGTH: 20
<212> TYPE: DNA
<213> ORGANISM: SOLANUM TUBEROSUM

<400> SEQUENCE: 20

tacaacagat aaaacaactt                                                 20


<210> SEQ ID NO 21
```

<211> LENGTH: 21
<212> TYPE: DNA
<213> ORGANISM: SOLANUM TUBEROSUM

<400> SEQUENCE: 21
ctaaaacaaa cagccacgga g 21

<210> SEQ ID NO 22
<211> LENGTH: 23
<212> TYPE: DNA
<213> ORGANISM: SOLANUM TUBEROSUM

<400> SEQUENCE: 22
atgcctctgg atagtgatgt ctt 23

<210> SEQ ID NO 23
<211> LENGTH: 18
<212> TYPE: DNA
<213> ORGANISM: SOLANUM TUBEROSUM

<400> SEQUENCE: 23
tcatggaatt tggtttat 18

<210> SEQ ID NO 24
<211> LENGTH: 19
<212> TYPE: DNA
<213> ORGANISM: SOLANUM TUBEROSUM

<400> SEQUENCE: 24
aacattcttt ctttcattc 19

<210> SEQ ID NO 25
<211> LENGTH: 22
<212> TYPE: DNA
<213> ORGANISM: SOLANUM TUBEROSUM

<400> SEQUENCE: 25
atgacaataa cagatgggat ac 22

<210> SEQ ID NO 26
<211> LENGTH: 22
<212> TYPE: DNA
<213> ORGANISM: SOLANUM TUBEROSUM

<400> SEQUENCE: 26
aacaacttaa tcgatggtca cg 22

<210> SEQ ID NO 27
<211> LENGTH: 19
<212> TYPE: DNA
<213> ORGANISM: SOLANUM TUBEROSUM

<400> SEQUENCE: 27
gatcagcttt ccccattag 19

<210> SEQ ID NO 28
<211> LENGTH: 18
<212> TYPE: DNA
<213> ORGANISM: SOLANUM TUBEROSUM

<400> SEQUENCE: 28
aaaaactgca aataacag 18

<210> SEQ ID NO 29

<211> LENGTH: 21
<212> TYPE: DNA
<213> ORGANISM: SOLANUM TUBEROSUM

<400> SEQUENCE: 29 cctttcact ggctcataat g 21

<210> SEQ ID NO 30
<211> LENGTH: 21
<212> TYPE: DNA
<213> ORGANISM: SOLANUM TUBEROSUM

<400> SEQUENCE: 30
caaggcactg atgtatgtaa c 21

<210> SEQ ID NO 31
<211> LENGTH: 19
<212> TYPE: DNA
<213> ORGANISM: SOLANUM TUBEROSUM

<400> SEQUENCE: 31
catgcattga actaagact 19

<210> SEQ ID NO 32
<211> LENGTH: 22
<212> TYPE: DNA
<213> ORGANISM: SOLANUM TUBEROSUM

<400> SEQUENCE: 32
tgtctcctct gcactaactt cc 22

<210> SEQ ID NO 33
<211> LENGTH: 21
<212> TYPE: DNA
<213> ORGANISM: SOLANUM TUBEROSUM

<400> SEQUENCE: 33
atttattttc atgtgggtgt g 21

<210> SEQ ID NO 34
<211> LENGTH: 20
<212> TYPE: DNA
<213> ORGANISM: SOLANUM TUBEROSUM

<400> SEQUENCE: 34
cagtttcttg atgttctaat 20

<210> SEQ ID NO 35
<211> LENGTH: 22
<212> TYPE: DNA
<213> ORGANISM: SOLANUM TUBEROSUM

<400> SEQUENCE: 35
aaattactct ccggaacttg aa 22

<210> SEQ ID NO 36
<211> LENGTH: 23
<212> TYPE: DNA
<213> ORGANISM: SOLANUM TUBEROSUM

<400> SEQUENCE: 36
tgcatatact tagttgatta cat 23

<210> SEQ ID NO 37

<211> LENGTH: 23
<212> TYPE: DNA
<213> ORGANISM: SOLANUM TUBEROSUM

<400> SEQUENCE: 37
gcacaagcta gtagattttt cag 23

<210> SEQ ID NO 38
<211> LENGTH: 20
<212> TYPE: DNA
<213> ORGANISM: SOLANUM TUBEROSUM

<400> SEQUENCE: 38
tcagtacatt tcaagacatt 20

<210> SEQ ID NO 39
<211> LENGTH: 19
<212> TYPE: DNA
<213> ORGANISM: SOLANUM TUBEROSUM

<400> SEQUENCE: 39
gacacgtaat ctcactttt 19

<210> SEQ ID NO 40
<211> LENGTH: 22
<212> TYPE: DNA
<213> ORGANISM: SOLANUM TUBEROSUM

<400> SEQUENCE: 40
ttcccagcag accaaatcca tg 22

<210> SEQ ID NO 41
<211> LENGTH: 23
<212> TYPE: DNA
<213> ORGANISM: SOLANUM TUBEROSUM

<400> SEQUENCE: 41
taaactcatc caaaagccat agg 23

<210> SEQ ID NO 42
<211> LENGTH: 19
<212> TYPE: DNA
<213> ORGANISM: SOLANUM TUBEROSUM

<400> SEQUENCE: 42
tctctttgca tggcgataa 19

<210> SEQ ID NO 43
<211> LENGTH: 17
<212> TYPE: DNA
<213> ORGANISM: SOLANUM TUBEROSUM

<400> SEQUENCE: 43
tctgcacgga agttttg 17

<210> SEQ ID NO 44
<211> LENGTH: 23
<212> TYPE: DNA
<213> ORGANISM: SOLANUM TUBEROSUM

<400> SEQUENCE: 44
tggtagagat taaaaagaac att 23

<210> SEQ ID NO 45

<211> LENGTH: 18
<212> TYPE: DNA
<213> ORGANISM: SOLANUM TUBEROSUM

<400> SEQUENCE: 45
agacgtgctg aaactatt 18

<210> SEQ ID NO 46
<211> LENGTH: 16
<212> TYPE: DNA
<213> ORGANISM: SOLANUM TUBEROSUM

<400> SEQUENCE: 46
ctcatgctca ctagct 16

<210> SEQ ID NO 47
<211> LENGTH: 17
<212> TYPE: DNA
<213> ORGANISM: SOLANUM TUBEROSUM

<400> SEQUENCE: 47
gaatagctaa tacgcca 17

<210> SEQ ID NO 48
<211> LENGTH: 17
<212> TYPE: DNA
<213> ORGANISM: SOLANUM TUBEROSUM

<400> SEQUENCE: 48
ccttcatgtt gaagttt 17

<210> SEQ ID NO 49
<211> LENGTH: 16
<212> TYPE: DNA
<213> ORGANISM: SOLANUM TUBEROSUM

<400> SEQUENCE: 49
caaggacagt tacgga 16

<210> SEQ ID NO 50
<211> LENGTH: 17
<212> TYPE: DNA
<213> ORGANISM: SOLANUM TUBEROSUM

<400> SEQUENCE: 50
tacataactg ttggtgg 17

<210> SEQ ID NO 51
<211> LENGTH: 15
<212> TYPE: DNA
<213> ORGANISM: SOLANUM TUBEROSUM

<400> SEQUENCE: 51
gtcacggtcc tcctg 15

<210> SEQ ID NO 52
<211> LENGTH: 17
<212> TYPE: DNA
<213> ORGANISM: SOLANUM TUBEROSUM

<400> SEQUENCE: 52
ctccaaccaa gaaggac 17

<210> SEQ ID NO 53

<211> LENGTH: 16
<212> TYPE: DNA
<213> ORGANISM: SOLANUM TUBEROSUM

<400> SEQUENCE: 53
acgatgatgg taacgc 16

<210> SEQ ID NO 54
<211> LENGTH: 24
<212> TYPE: DNA
<213> ORGANISM: SOLANUM TUBEROSUM

<400> SEQUENCE: 54
ccacaaccta cacctaagtc acaa 24

<210> SEQ ID NO 55
<211> LENGTH: 21
<212> TYPE: DNA
<213> ORGANISM: SOLANUM TUBEROSUM

<400> SEQUENCE: 55
ggcattggac agaagtaacc t 21

<210> SEQ ID NO 56
<211> LENGTH: 24
<212> TYPE: DNA
<213> ORGANISM: SOLANUM TUBEROSUM

<400> SEQUENCE: 56
ttagttgtca cattttcctc ttac 24

<210> SEQ ID NO 57
<211> LENGTH: 21
<212> TYPE: DNA
<213> ORGANISM: SOLANUM TUBEROSUM

<400> SEQUENCE: 57
gatgttcgag tcctggtttg t 21

<210> SEQ ID NO 58
<211> LENGTH: 24
<212> TYPE: DNA
<213> ORGANISM: SOLANUM TUBEROSUM

<400> SEQUENCE: 58
gtatctgatg ggagtctgtc tggt 24

<210> SEQ ID NO 59
<211> LENGTH: 19
<212> TYPE: DNA
<213> ORGANISM: SOLANUM TUBEROSUM

<400> SEQUENCE: 59
cctcgacgaa atccacaag 19

<210> SEQ ID NO 60
<211> LENGTH: 21
<212> TYPE: DNA
<213> ORGANISM: SOLANUM TUBEROSUM

<400> SEQUENCE: 60
atcttgagct aggagttatg g 21

<210> SEQ ID NO 61

<211> LENGTH: 18
<212> TYPE: DNA
<213> ORGANISM: SOLANUM TUBEROSUM

<400> SEQUENCE: 61
ctacgaaagg atgtgatg 18

<210> SEQ ID NO 62
<211> LENGTH: 21
<212> TYPE: DNA
<213> ORGANISM: SOLANUM TUBEROSUM

<400> SEQUENCE: 62
atgagcacaa aatagatgat a 21

<210> SEQ ID NO 63
<211> LENGTH: 24
<212> TYPE: DNA
<213> ORGANISM: SOLANUM TUBEROSUM

<400> SEQUENCE: 63
aagtgtagaa aatatgggtt agta 24

<210> SEQ ID NO 64
<211> LENGTH: 24
<212> TYPE: DNA
<213> ORGANISM: SOLANUM TUBEROSUM

<400> SEQUENCE: 64
gccactaata taaccaatcc acat 24

<210> SEQ ID NO 65
<211> LENGTH: 19
<212> TYPE: DNA
<213> ORGANISM: SOLANUM TUBEROSUM

<400> SEQUENCE: 65
cccccatacc gaaaagagg 19

<210> SEQ ID NO 66
<211> LENGTH: 21
<212> TYPE: DNA
<213> ORGANISM: SOLANUM TUBEROSUM

<400> SEQUENCE: 66
ctgatgcttg cattagtgta t 21

<210> SEQ ID NO 67
<211> LENGTH: 22
<212> TYPE: DNA
<213> ORGANISM: SOLANUM TUBEROSUM

<400> SEQUENCE: 67
atgatgatct tcctccctct gc 22

<210> SEQ ID NO 68
<211> LENGTH: 19
<212> TYPE: DNA
<213> ORGANISM: SOLANUM TUBEROSUM

<400> SEQUENCE: 68
tacctttcca gaccttagt 19

<210> SEQ ID NO 69

<211> LENGTH: 21
<212> TYPE: DNA
<213> ORGANISM: SOLANUM TUBEROSUM

<400> SEQUENCE: 69
cctaatagac tgggaacgac a 21

<210> SEQ ID NO 70
<211> LENGTH: 18
<212> TYPE: DNA
<213> ORGANISM: SOLANUM TUBEROSUM

<400> SEQUENCE: 70
tcttcgacac aacctctc 18

<210> SEQ ID NO 71
<211> LENGTH: 34
<212> TYPE: DNA
<213> ORGANISM: SOLANUM TUBEROSUM

<400> SEQUENCE: 71
gcaggatccc gaactcagtt tccgtctgtt gata 34

<210> SEQ ID NO 72
<211> LENGTH: 38
<212> TYPE: DNA
<213> ORGANISM: SOLANUM TUBEROSUM

<400> SEQUENCE: 72
gagggatcca tgttgcttta tatcttcttt ttgttatc 38

<210> SEQ ID NO 73
<211> LENGTH: 14
<212> TYPE: DNA
<213> ORGANISM: SOLANUM TUBEROSUM

<400> SEQUENCE: 73
ttctttttgt tatc 14

<210> SEQ ID NO 74
<211> LENGTH: 49
<212> TYPE: DNA
<213> ORGANISM: SOLANUM TUBEROSUM

<400> SEQUENCE: 74
gcaggatcca tggtcatatt tgcttgtgga gataatccta ggccttttg 49

<210> SEQ ID NO 75
<211> LENGTH: 41
<212> TYPE: DNA
<213> ORGANISM: SOLANUM TUBEROSUM

<400> SEQUENCE: 75
gagggatccc ataattaagg agaaaaacat acaacaagac t 41

<210> SEQ ID NO 76
<211> LENGTH: 33
<212> TYPE: DNA
<213> ORGANISM: SOLANUM TUBEROSUM

<400> SEQUENCE: 76
gacggatccg gatatggcag tgcgaaggtt gtc 33

<210> SEQ ID NO 77

<211> LENGTH: 35
<212> TYPE: DNA
<213> ORGANISM: SOLANUM TUBEROSUM

<400> SEQUENCE: 77
gacggatccg ttaaccatgc aactcagcat tccac 35

<210> SEQ ID NO 78
<211> LENGTH: 24
<212> TYPE: DNA
<213> ORGANISM: SOLANUM TUBEROSUM

<400> SEQUENCE: 78
atgttgtatg acgctcttga tacc 24

<210> SEQ ID NO 79
<211> LENGTH: 8
<212> TYPE: PRT
<213> ORGANISM: SOLANUM TUBEROSUM

<400> SEQUENCE: 79

```
Ser Gln Phe Pro Ser Met Asn Ile
 1               5
```

<210> SEQ ID NO 80
<211> LENGTH: 21
<212> TYPE: PRT
<213> ORGANISM: SOLANUM TUBEROSUM

<400> SEQUENCE: 80

```
Val Leu Phe Val Gly Asp Leu Ser Tyr Ala Asp Arg Tyr Gln Tyr Asn
 1               5                  10                  15

Asp Val Gly Val Arg
            20
```

<210> SEQ ID NO 81
<211> LENGTH: 17
<212> TYPE: PRT
<213> ORGANISM: SOLANUM TUBEROSUM
<220> FEATURE:
<221> NAME/KEY: VARIANT
<222> LOCATION: (1)...(17)
<223> OTHER INFORMATION: Xaa = Any Amino Acid

<400> SEQUENCE: 81

```
Lys Phe Xaa Phe Glu Thr Pro Pro Lys Val Asp Pro Asp Ala Ser Tyr
 1               5                  10                  15

Lys
```

<210> SEQ ID NO 82
<211> LENGTH: 18
<212> TYPE: PRT
<213> ORGANISM: SOLANUM TUBEROSUM
<220> FEATURE:
<221> NAME/KEY: VARIANT
<222> LOCATION: (1)...(18)
<223> OTHER INFORMATION: Xaa = Any Amino Acid

<400> SEQUENCE: 82

```
Asn Asp Asp Gly Asn Xaa Xaa Thr Thr Asp Ser Phe Thr Leu His Asn
 1               5                  10                  15

Gln Tyr
```

<210> SEQ ID NO 83
<211> LENGTH: 12

```
<212> TYPE: PRT
<213> ORGANISM: SOLANUM TUBEROSUM

<400> SEQUENCE: 83

Phe Arg Asp Pro Gln Pro Glu Tyr Ser Ala Phe Arg
 1               5                   10


<210> SEQ ID NO 84
<211> LENGTH: 18
<212> TYPE: PRT
<213> ORGANISM: SOLANUM TUBEROSUM
<220> FEATURE:
<221> NAME/KEY: VARIANT
<222> LOCATION: (1)...(18)
<223> OTHER INFORMATION: Xaa = Any Amino Acid

<400> SEQUENCE: 84

Thr Gly Phe Pro Xaa Val Ser Gly Gly Xaa Ala Tyr Pro Val Pro Thr
 1               5                   10                  15

Gly Lys


<210> SEQ ID NO 85
<211> LENGTH: 11
<212> TYPE: PRT
<213> ORGANISM: SOLANUM TUBEROSUM
<220> FEATURE:
<221> NAME/KEY: VARIANT
<222> LOCATION: (1)...(11)
<223> OTHER INFORMATION: Xaa = Any Amino Acid

<400> SEQUENCE: 85

Thr Gly Phe Pro Xaa Val Xaa Xaa Pro Leu Glu
 1               5                   10


<210> SEQ ID NO 86
<211> LENGTH: 15
<212> TYPE: PRT
<213> ORGANISM: SOLANUM TUBEROSUM
<220> FEATURE:
<221> NAME/KEY: VARIANT
<222> LOCATION: (1)...(15)
<223> OTHER INFORMATION: Xaa = Any Amino Acid

<400> SEQUENCE: 86

Arg Gln Phe Pro Ile Val Asp Asp Ile Pro Leu Glu Asn Xaa Val
 1               5                   10                  15


<210> SEQ ID NO 87
<211> LENGTH: 21
<212> TYPE: PRT
<213> ORGANISM: SOLANUM TUBEROSUM

<400> SEQUENCE: 87

Met Glu Ser Ala Tyr Glu Val Trp Asp Phe Val Lys Tyr Lys Val Asp
 1               5                   10                  15

Val Ile Phe Ala Gly
            20


<210> SEQ ID NO 88
<211> LENGTH: 37
<212> TYPE: DNA
<213> ORGANISM: SOLANUM TUBEROSUM
<220> FEATURE:
<221> NAME/KEY: misc_feature
<222> LOCATION: (1)...(37)
<223> OTHER INFORMATION: n = A,T,C or G

<400> SEQUENCE: 88
```

```
tttcgaagac nccnccnaaa ggtngatccc ngatcgc                                    37


<210> SEQ ID NO 89
<211> LENGTH: 11
<212> TYPE: PRT
<213> ORGANISM: ORYSA SATIVA

<400> SEQUENCE: 89

Asp Leu Ser Tyr Ala Asp Arg Tyr Gln Tyr Asn
 1               5                   10


<210> SEQ ID NO 90
<211> LENGTH: 10
<212> TYPE: PRT
<213> ORGANISM: ORYSA SATIVA
<220> FEATURE:
<221> NAME/KEY: VARIANT
<222> LOCATION: (1)...(10)
<223> OTHER INFORMATION: Xaa = Any Amino Acid

<400> SEQUENCE: 90

Asp Ser Tyr Ala Asp Arg Tyr Gln Xaa Asn
 1               5                   10


<210> SEQ ID NO 91
<211> LENGTH: 11
<212> TYPE: PRT
<213> ORGANISM: ORYSA SATIVA
<220> FEATURE:
<221> NAME/KEY: VARIANT
<222> LOCATION: (1)...(11)
<223> OTHER INFORMATION: Xaa = Any Amino Acid

<400> SEQUENCE: 91

Asp Xaa Ser Tyr Ala Asp Arg Tyr Gln His Asn
 1               5                   10


<210> SEQ ID NO 92
<211> LENGTH: 20
<212> TYPE: PRT
<213> ORGANISM: ORYSA SATIVA

<400> SEQUENCE: 92

Met Glu Ser Ala Tyr Glu Val Trp Phe Val Lys Tyr Lys Val Asp Val
 1               5                   10                  15

Ile Phe Ala Gly
            20


<210> SEQ ID NO 93
<211> LENGTH: 18
<212> TYPE: PRT
<213> ORGANISM: ORYSA SATIVA
<220> FEATURE:
<221> NAME/KEY: VARIANT
<222> LOCATION: (1)...(18)
<223> OTHER INFORMATION: Xaa = Any Amino Acid

<400> SEQUENCE: 93

Met Xaa Ala Xaa Glu Trp Phe Val Lys Tyr Lys Val Asp Xaa Xaa Phe
 1               5                   10                  15

Ala Gly


<210> SEQ ID NO 94
<211> LENGTH: 20
<212> TYPE: PRT
<213> ORGANISM: ORYSA SATIVA
```

<400> SEQUENCE: 94

```
Met Arg Ala Ala Phe Glu Lys Trp Phe Val Lys Tyr Lys Val Asp Leu
 1               5                  10                  15

Val Phe Ala Gly
            20
```

<210> SEQ ID NO 95
<211> LENGTH: 17
<212> TYPE: PRT
<213> ORGANISM: SOLANUM TUBEROSUM
<220> FEATURE:
<221> NAME/KEY: VARIANT
<222> LOCATION: (1)...(17)
<223> OTHER INFORMATION: Xaa = Any Amino Acid

<400> SEQUENCE: 95

```
Lys Phe Xaa Phe Glu Thr Pro Pro Lys Val Asp Pro Asp Ala Ser Tyr
 1               5                  10                  15

Lys
```

<210> SEQ ID NO 96
<211> LENGTH: 16
<212> TYPE: PRT
<213> ORGANISM: SOLANUM TUBEROSUM

<400> SEQUENCE: 96

```
Lys Phe Phe Glu Thr Pro Pro Lys Val Asp Pro Asp Ala Ser Tyr Lys
 1               5                  10                  15
```

<210> SEQ ID NO 97
<211> LENGTH: 17
<212> TYPE: PRT
<213> ORGANISM: SOLANUM TUBEROSUM

<400> SEQUENCE: 97

```
Lys Phe Trp Phe Glu Thr Pro Pro Lys Val Asp Pro Asp Ala Ser Tyr
 1               5                  10                  15

Lys
```

<210> SEQ ID NO 98
<211> LENGTH: 21
<212> TYPE: PRT
<213> ORGANISM: SOLANUM TUBEROSUM

<400> SEQUENCE: 98

```
Val Leu Phe Val Gly Asp Leu Ser Tyr Ala Asp Arg Tyr Gln Tyr Asn
 1               5                  10                  15

Asp Val Gly Val Arg
            20
```

<210> SEQ ID NO 99
<211> LENGTH: 20
<212> TYPE: PRT
<213> ORGANISM: ORYSA SATIVA

<400> SEQUENCE: 99

```
Val Asp Arg Glu Lys Thr Pro Trp Leu Ile Val Leu Met His Ser Pro
 1               5                  10                  15

Met Tyr Asn Ser
            20
```

<210> SEQ ID NO 100

<211> LENGTH: 19
<212> TYPE: PRT
<213> ORGANISM: ORYSA SATIVA
<220> FEATURE:
<221> NAME/KEY: VARIANT
<222> LOCATION: (1)...(19)
<223> OTHER INFORMATION: Xaa = Any Amino Acid

<400> SEQUENCE: 100

```
Val Asp Arg Xaa Lys Thr Pro Trp Xaa Xaa Val Xaa His Xaa Pro Met
 1               5                  10                  15

Tyr Xaa Ser
```

<210> SEQ ID NO 101
<211> LENGTH: 20
<212> TYPE: PRT
<213> ORGANISM: ASPERGILLUS FICUUM

<400> SEQUENCE: 101

```
Val Asp Arg Ser Lys Thr Pro Trp Val Phe Val Met Ser His Arg Pro
 1               5                  10                  15

Met Tyr Ser Ser
            20
```

<210> SEQ ID NO 102
<211> LENGTH: 27
<212> TYPE: PRT
<213> ORGANISM: ORYSA SATIVA

<400> SEQUENCE: 102

```
Met Arg Ala Ala Phe Glu Lys Trp Phe Val Lys Tyr Lys Val Asp Leu
 1               5                  10                  15

Val Phe Ala Gly His Val His Ala Tyr Glu Arg
            20                  25
```

<210> SEQ ID NO 103
<211> LENGTH: 21
<212> TYPE: PRT
<213> ORGANISM: ORYSA SATIVA
<220> FEATURE:
<221> NAME/KEY: VARIANT
<222> LOCATION: (1)...(21)
<223> OTHER INFORMATION: Xaa = Any Amino Acid

<400> SEQUENCE: 103

```
Xaa Arg Xaa Ala Phe Glu Xaa Xaa Lys Tyr Val Asp Phe Xaa Gly His
 1               5                  10                  15

Xaa His Tyr Glu Arg
            20
```

<210> SEQ ID NO 104
<211> LENGTH: 27
<212> TYPE: PRT
<213> ORGANISM: ASPERGILLUS FICUUM

<400> SEQUENCE: 104

```
Val Arg Glu Ala Phe Glu Gly Leu Leu Leu Lys Tyr Gly Val Asp Ala
 1               5                  10                  15

Tyr Phe Ser Gly His Ile His Trp Tyr Glu Arg
            20                  25
```

<210> SEQ ID NO 105
<211> LENGTH: 14
<212> TYPE: PRT
<213> ORGANISM: SOLANUM TUBEROSUM

<400> SEQUENCE: 105

```
Thr Gln Phe Pro Ser Val Asp Ile Pro Leu Glu Asn Glu Val
 1               5                  10
```

<210> SEQ ID NO 106
<211> LENGTH: 11
<212> TYPE: PRT
<213> ORGANISM: SOLANUM TUBEROSUM
<220> FEATURE:
<221> NAME/KEY: VARIANT
<222> LOCATION: (1)...(11)
<223> OTHER INFORMATION: Xaa = Any Amino Acid

<400> SEQUENCE: 106

```
Thr Gly Phe Pro Xaa Val Xaa Ile Pro Leu Glu
 1               5                  10
```

<210> SEQ ID NO 107
<211> LENGTH: 14
<212> TYPE: PRT
<213> ORGANISM: SOLANUM TUBEROSUM
<220> FEATURE:
<221> NAME/KEY: VARIANT
<222> LOCATION: (1)...(14)
<223> OTHER INFORMATION: Xaa = Any Amino Acid

<400> SEQUENCE: 107

```
Arg Gln Phe Pro Ile Val Asp Ile Pro Leu Glu Asn Xaa Val
 1               5                  10
```

<210> SEQ ID NO 108
<211> LENGTH: 20
<212> TYPE: PRT
<213> ORGANISM: SOLANUM TUBEROSUM

<400> SEQUENCE: 108

```
Met Arg Ser Ala Tyr Glu Arg Trp Phe Val Lys Tyr Lys Val Asp Val
 1               5                  10                  15

Ile Phe Ala Gly
            20
```

<210> SEQ ID NO 109
<211> LENGTH: 18
<212> TYPE: PRT
<213> ORGANISM: SOLANUM TUBEROSUM

<400> SEQUENCE: 109

```
Met Ser Ala Tyr Glu Trp Phe Val Lys Tyr Lys Val Asp Val Ile Phe
 1               5                  10                  15

Ala Gly
```

<210> SEQ ID NO 110
<211> LENGTH: 20
<212> TYPE: PRT
<213> ORGANISM: SOLANUM TUBEROSUM

<400> SEQUENCE: 110

```
Met Glu Ser Ala Tyr Glu Val Trp Phe Val Lys Tyr Lys Val Asp Val
 1               5                  10                  15

Ile Phe Ala Gly
            20
```

<210> SEQ ID NO 111
<211> LENGTH: 19

<212> TYPE: PRT
<213> ORGANISM: SOLANUM TUBEROSUM

<400> SEQUENCE: 111

Ile Ser Asn Ile His Tyr Asn Val Ser Gly Gly Asp Ala Tyr Pro Val
 1               5                  10                  15

Pro Asp Lys

<210> SEQ ID NO 112
<211> LENGTH: 16
<212> TYPE: PRT
<213> ORGANISM: SOLANUM TUBEROSUM

<400> SEQUENCE: 112

Ile Ser Asn Ile His Tyr Val Ser Gly Gly Ala Tyr Pro Val Pro Lys
 1               5                  10                  15

<210> SEQ ID NO 113
<211> LENGTH: 19
<212> TYPE: PRT
<213> ORGANISM: SOLANUM TUBEROSUM
<220> FEATURE:
<221> NAME/KEY: VARIANT
<222> LOCATION: (1)...(19)
<223> OTHER INFORMATION: Xaa = Any Amino Acid

<400> SEQUENCE: 113

Ile Ser Asn Ile His Tyr Xaa Val Ser Gly Gly Xaa Ala Tyr Pro Val
 1               5                  10                  15

Pro Xaa Lys

<210> SEQ ID NO 114
<211> LENGTH: 12
<212> TYPE: PRT
<213> ORGANISM: SOLANUM TUBEROSUM

<400> SEQUENCE: 114

Phe Arg Asp Pro Gln Pro Glu Tyr Ser Ala Phe Arg
 1               5                  10

<210> SEQ ID NO 115
<211> LENGTH: 17
<212> TYPE: PRT
<213> ORGANISM: SOLANUM TUBEROSUM

<400> SEQUENCE: 115

Asn Asp Asp Gly Asn Ala Ile Thr Thr Asp Ser Phe Thr Leu His Asn
 1               5                  10                  15

Gln

<210> SEQ ID NO 116
<211> LENGTH: 16
<212> TYPE: PRT
<213> ORGANISM: SOLANUM TUBEROSUM

<400> SEQUENCE: 116

Asn Asp Asp Gly Asn Ile Thr Thr Asp Ser Phe Thr Leu His Asn Gln
 1               5                  10                  15

<210> SEQ ID NO 117
<211> LENGTH: 17
<212> TYPE: PRT
<213> ORGANISM: SOLANUM TUBEROSUM
<220> FEATURE:
<221> NAME/KEY: VARIANT

```
<222> LOCATION: (1)...(17)
<223> OTHER INFORMATION: Xaa = Any Amino Acid

<400> SEQUENCE: 117

Asn Asp Asp Gly Asn Xaa Ile Thr Thr Asp Ser Phe Thr Leu His Asn
 1               5                  10                  15

Gln


<210> SEQ ID NO 118
<211> LENGTH: 432
<212> TYPE: PRT
<213> ORGANISM: SOLANUM TUBEROSUM


<400> SEQUENCE: 118

Phe Val Arg Lys Thr Asn Lys Asn Arg Asp Met Pro Leu Asp Ser Asp
 1               5                  10                  15

Val Phe Arg Val Pro Pro Gly Tyr Asn Ala Pro Gln Gln Val His Ile
            20                  25                  30

Thr Gln Gly Asp Leu Val Gly Arg Ala Met Ile Ile Ser Trp Val Thr
        35                  40                  45

Met Asp Glu Pro Gly Ser Ser Ala Val Arg Tyr Trp Ser Glu Lys Asn
    50                  55                  60

Gly Arg Lys Arg Ile Ala Lys Gly Lys Met Ser Thr Tyr Arg Phe Phe
65                  70                  75                  80

Asn Tyr Ser Ser Gly Phe Ile His His Thr Thr Ile Arg Lys Leu Lys
                85                  90                  95

Tyr Asn Tyr Lys Tyr Tyr Tyr Glu Val Gly Leu Arg Asn Thr Thr Arg
            100                 105                 110

Arg Phe Ser Phe Ile Thr Pro Pro Gln Thr Gly Leu Asp Val Pro Tyr
        115                 120                 125

Thr Phe Gly Leu Ile Gly Asp Leu Gly Gln Ser Phe Asp Ser Asn Thr
    130                 135                 140

Thr Leu Ser His Tyr Glu Leu Ser Pro Lys Lys Gly Gln Thr Val Leu
145                 150                 155                 160

Phe Val Gly Asp Leu Ser Tyr Ala Asp Arg Tyr Pro Asn His Asp Asn
                165                 170                 175

Val Arg Trp Asp Thr Trp Gly Arg Phe Thr Glu Arg Ser Val Ala Tyr
            180                 185                 190

Gln Pro Trp Ile Trp Thr Ala Gly Asn His Glu Ile Glu Phe Ala Pro
        195                 200                 205

Glu Ile Asn Glu Thr Glu Pro Phe Lys Pro Phe Ser Tyr Arg Tyr His
    210                 215                 220

Val Pro Tyr Glu Ala Ser Gln Ser Thr Ser Pro Phe Trp Tyr Ser Ile
225                 230                 235                 240

Lys Arg Ala Ser Ala His Ile Ile Val Leu Ser Ser His Ile Ala Tyr
                245                 250                 255

Gly Arg Gly Thr Pro Gln Tyr Thr Trp Leu Lys Lys Glu Leu Arg Lys
            260                 265                 270

Val Lys Arg Ser Glu Thr Pro Trp Leu Ile Val Leu Met His Ser Pro
        275                 280                 285

Leu Tyr Asn Ser Tyr Asn His His Phe Met Glu Gly Glu Ala Met Arg
    290                 295                 300

Thr Lys Phe Glu Ala Trp Phe Val Lys Tyr Lys Val Asp Val Val Phe
305                 310                 315                 320

Ala Gly His Val His Ala Tyr Glu Arg Ser Glu Arg Val Ser Asn Ile
```

```
                325                 330                 335

Ala Tyr Lys Ile Thr Asp Gly Leu Cys Thr Pro Val Lys Asp Gln Ser
            340                 345                 350

Ala Pro Val Tyr Ile Thr Ile Gly Asp Ala Gly Asn Tyr Gly Val Ile
        355                 360                 365

Asp Ser Asn Met Ile Gln Pro Gln Pro Glu Tyr Ser Ala Phe Arg Glu
    370                 375                 380

Ala Ser Phe Gly His Gly Met Phe Asp Ile Lys Asn Arg Thr His Ala
385                 390                 395                 400

His Phe Ser Trp Asn Arg Asn Gln Asp Gly Val Ala Val Glu Ala Asp
                405                 410                 415

Ser Val Trp Phe Phe Asn Arg His Trp Tyr Pro Val Asp Asp Ser Thr
            420                 425                 430


<210> SEQ ID NO 119
<211> LENGTH: 281
<212> TYPE: PRT
<213> ORGANISM: ORYSA SATIVA


<400> SEQUENCE: 119

Ala Arg Asp Gln His Asn Asp Gly Val Arg Trp Asp Ser Trp Gly Arg
 1               5                  10                  15

Leu Val Glu Arg Ser Thr Ala Tyr Gln Pro Trp Ile Trp Ser Ala Gly
            20                  25                  30

Asn His Glu Ile Glu Tyr Arg Pro Asp Leu Gly Glu Thr Ser Thr Phe
        35                  40                  45

Lys Pro Tyr Leu His Arg Cys His Thr Pro Tyr Leu Ala Ser Lys Ser
    50                  55                  60

Ser Ser Pro Met Trp Tyr Ala Val Arg Arg Ala Ser Ala His Ile Ile
65                  70                  75                  80

Val Leu Ser Ser Tyr Ser Pro Phe Val Lys Tyr Thr Pro Gln Trp Thr
                85                  90                  95

Trp Leu Lys Tyr Glu Leu Lys His Val Asp Arg Glu Lys Thr Pro Trp
            100                 105                 110

Leu Ile Val Leu Met His Ser Pro Met Tyr Asn Ser Asn Glu Ala His
        115                 120                 125

Tyr Met Glu Gly Glu Ser Met Arg Ala Ala Phe Glu Lys Trp Phe Val
    130                 135                 140

Lys Tyr Lys Val Asp Leu Val Phe Ala Gly His Val His Ala Tyr Glu
145                 150                 155                 160

Arg Ser Tyr Arg Ile Ser Asn Ile Asn Tyr Asn Ile Thr Ser Gly Asn
                165                 170                 175

Arg Tyr Pro Val Pro Asp Lys Ser Ala Pro Val Tyr Ile Thr Val Gly
            180                 185                 190

Asp Gly Gly Asn Gln Glu Gly Leu Ala Ser Arg Phe Ser Asp Pro Gln
        195                 200                 205

Pro Asp Tyr Ser Ala Phe Arg Glu Ala Ser Tyr Gly His Ser Ile Leu
    210                 215                 220

Gln Leu Lys Asn Arg Thr His Ala Ile Tyr Gln Trp Asn Arg Asn Asp
225                 230                 235                 240

Asp Gly Lys His Val Pro Ala Asp Asn Val Val Phe His Asn Gln Tyr
                245                 250                 255

Trp Ala Ser Asn Thr Arg Arg Arg Arg Leu Lys Lys Lys His Phe His
            260                 265                 270
```

-continued

```
Leu Asp Gln Ile Glu Asp Leu Ile Ser
        275                 280
```

PLANT PHOSPHATASES

BACKGROUND OF THE INVENTION

Phosphorus is a major mineral nutrient essential to the growth and reproduction of photosynthetic organisms. Plants grown under natural soil conditions often experience sub-optimal growth because of inorganic phosphate (Pi) deprivation. Because crop productivity is strongly influenced by the availability of phosphorus, phosphate fertilizers are used to supplement the natural soil levels. However, excess phosphorus upsets the natural balance of aquatic and terrestrial ecosystems which border agricultural lands. Further, it is estimated that the mineral sources of phosphorus for the production of fertilizers will become severely depleted within fifteen years. Even a modest increase in the efficiency of plants to utilize phosphorus would make a significant contribution to the reduction of agricultural expenditures by producers and lower the impact on untilled ecosystems.

Phosphatase activity (orthophosphate-monoester phosphohydrolase) has been observed in all plants and in all tissues. Phosphatases are involved in the routine turnover of Pi from the many intracellular sources of orthophosphate esters (Hollander, 1971). Certain phosphatases exhibit phosphate-stress induction (psi) and are implicated in Pi acquisition through the release of Pi from the environment or from intracellular sources. Typically, these psi phosphatases are abundant and active toward a broad range of substrates. In contrast, the expression of phosphatases involved in cellular and metabolic regulation is generally discrete and tightly regulated.

Defined according to their pH optima, there are two types of phosphatases. The acid phosphatase (APase) and alkaline phosphatase subclasses are structurally distinct and undergo different reaction mechanisms (Kim and Wyckoff, 1989; Neuman, 1968). Alkaline phosphatases tend to demonstrate specificity toward a particular substrate whereas APases usually have no absolute substrate preference.

A major response to phosphate-deficiency involves the induction of phosphatase activity. Because the phosphoesters or polyphosphates found in soil cannot directly be assimilated by plant roots, Pi must be released from these compounds by phosphatase-mediated hydrolysis. Under phosphate-deficient conditions, increased acid phosphatase activity has been demonstrated in a number of plant species (Lefebvre et al, 1990; Dracup et al, 1984; Lefebvre and Glass, 1982). APases that respond in this manner are produced de novo and are secreted to the external cell wall environment in roots (Szabó-Nagy et al, 1987) and cell cultures (Duff et al, 1991a; Lefebvre et al, 1990). Controlling the expression of plant APases could result in crops with an enhanced capacity for phosphate uptake and lower fertilization requirements.

APases have been identified in every plant species tested and a number have been characterized (Duff et al, 1994). A species survey using antibodies raised against a Brassica nigra APase suggests a major family of closely related APases exists among plants (Duff et al, 1991b). A plant APase gene has been isolated that codes for a storage protein-related phosphatase (Erion et al, 1992); however, this enzyme is distinct from the major family of APases in both structure and function. No genes encoding members of the major family of plant phosphatases have been reported.

Detailed knowledge of the plant phosphatases which affect the uptake and metabolism of phosphorus is essential to understand phosphate metabolism and to manipulate the growth and reproduction of photosynthetic organisms for commercial or industrial purposes. Further, the identification and synthesis of the genes which encode plant phosphatases would allow the development of transgenic photosynthetic organisms for many purposes.

SUMMARY OF THE INVENTION

The present invention relates to nucleic acids encoding members of the major family of plant phosphatases and the proteins encoded by these nucleic acids. These nucleic acids include DNA and RNA encoding phosphatases from potato tubers and rice and their encoded polypeptides. The availability of these nucleic acids and proteins make it possible to modify all plants and photosynthetic organisms, including important agricultural and horticultural species of plants, whether monocotyledonous or dicotyledonous.

This invention further relates to the modification of phosphorus metabolism in plants and other photosynthetic organisms by altering the expression and/or activity of proteins involved in phosphate metabolism. This invention further includes the compositions and methods useful for providing more efficient metabolic utilization of phosphorus by plants and other photosynthetic organisms. The compositions of this invention also encompass methods to change plant morphology by altering phosphorus metabolism. In some applications, the modification will be restricted to seeds, where it can lower the amount of phytate, an anti-nutritive phosphorus storage compound.

This invention further relates to isolated nucleic acids encoding proteins involved in phosphorus uptake and metabolism of plants and other photosynthetic organisms (plant phosphatase proteins), as well as nucleic acids complementary to these genes, and recombinant nucleic acid constructs and vectors containing DNA encoding such proteins or such complementary DNA or RNA, in whole or portions thereof.

In particular, the present invention includes DNA (genes) encoding phosphatase of potato (*Solanum tuberosum*) and rice (*Orysa sativa* cv. Japonica) whose transcription is inducible by phosphate, and further encompasses RNA transcribed by this DNA. The proteins of this invention include PTAP (potato phosphatase), three related potato phosphatases, PAP3, PAP7 and PAP11, and a related cDNA clone, RAP, which was isolated from a rice suspension culture library (Uchimiya et al, 1992).

The nucleic acids (both DNA and RNA) of this invention encode proteins which differ from other plant phosphatases in having a unique portion of their amino acid sequence which differs from any other known plant phosphatases.

Other nucleic acids of the invention include nucleic acids with sequences complementary to the nucleic acid sequences of *Solanum tuberosum* and *Orysa sativa* cv. Japonica, or portions thereof; nucleic acids with sequences related to, but distinct from, the nucleic acid sequences of *Solanum tuberosum* and *Orysa sativa* cv. Japonica; and nucleic acid sequences that differ from the nucleic acid sequences of *Solanum tuberosum* and Orysa sativa cv. Japonica, such as modified analogues, due to alteration of the sequence through mutation, substitution, deletion and the like.

Primers and probes consisting of 20 or more contiguous nucleotides of the above-described nucleic acids are also included as part of this invention. Thus, one nucleic acid of this invention comprises a specific sequence of about 20 to about 200 or more nucleotides which are identical or complementary to a specific sequence of nucleotides of the plant phosphatase protein-encoding DNA or transcribed mRNA.

The invention further relates to nucleic acids of the invention operatively linked to a regulatory sequence, and plasmids or recombinant expression vectors for producing the nucleic acids encompassed by this invention. In a preferred embodiment, a recombinant expression vector, comprising the nucleic acids operatively linked to a regulatory sequence is adapted for transformation of a plant cell.

The invention also encompasses transgenic cells expressing these phosphatase proteins or a portion thereof. In a preferred embodiment, the transgenic cells are plant cells. The invention includes transgenic plants produced with nucleic acids or vectors of the invention which express phosphatase proteins or portions thereof provided by the invention. The invention further includes transgenic plant parts, including seeds, as well as tissue culture or protoplasts produced with nucleic acids or vectors of the invention.

The invention further includes methods of preparing phosphatase proteins having phosphatase protein activity using the nucleic acids of the invention. One method comprises culturing a transformant or transgenic cell including a recombinant expression vector comprising a nucleic acid of the invention and a regulatory sequence operatively linked to the nucleic acid in a suitable medium until the phosphatase protein is expressed, and then isolating the phosphatase protein. The invention also provides an isolated phosphatase or polypeptides having phosphatase protein activity and substantial sequence similarity with either or both of the amino acid sequences shown in SEQ ID NO 1: SEQ ID NO 2:, SEQ ID NO 3:, SEQ ID NO 4, or a portion thereof.

Antibodies and antibody fragments which bind to the novel phosphatase described herein (or to portions of these sequences) are also included in this invention. In a preferred embodiment, the antibody is a monoclonal antibody. Other types of molecules which bind to and block the activity of these phosphatases are included as well.

Thus, this invention provides a system for modifying the phosphate metabolism of a photosynthetic organism. This approach to modifying the phosphate pathways of plants has several advantages over traditional plant breeding methods, most importantly, the modifications can be made quickly and specific traits can be modified, even through introduction of a new trait which is not part of the plant genome.

BRIEF DESCRIPTION OF THE DRAWINGS

FIG. 1 is the DNA (SEQ ID NO:5) and deduced amino acid sequence (SEQ ID NO:10) of rice phosphatase clone RAP cloned into the Eco RI site of pBluescript. Nucleotides are numbered on the left. Single letter amino acid designations are given below their respective codons and are numbered on the right. The termination codon is designated with '*'.

FIG. 2 is the DNA (SEQ ID NO:15) and deduced amino acid sequence (SEQ ID NO:6) of potato phosphatase genomic clone PTAP-2 assembled exons. Eight exon sequences were complied from analysis of the 9.4 kb of PTAP-2 sequence data of subcloned restriction fragments 4-2.2, 4-1.4, 4-3.8 and 4-4.7 (See FIGS. 12A and 12B). Exon and intron junctions were deduced from alignment with related phosphatase sequences and predicted from hspl and aspl splice-site determination programs from the Human Genome Center (Houston, Tex.). Nucleotides are given on the left. Single letter amino acid designations are given below their respective codons and are numbered on the right.

FIGS. 3A–3C are the complete DNA (SEQ ID NO:2) and deduced amino acid sequence (SEQ ID NO:7) of potato phosphatase genomic clone PAP3. Nucleotide numbers are indicated on the left. Single letter amino acid designations are given below their respective codons and are numbered on the right.

FIG. 4 shows the alignment of the deduced amino acid sequences of PTAP, RAP, PAP3, PAP7 (SEQ ID NO:8) and PAP11 (SEQ ID NO:9) and the protein sequence of kidney bean purple phosphatase (KBPAP) using the CLUSTAL program (Higgins and Sharp, 1988). Amino acid sequence numbers are shown on the right of each line. Shaded residues have sequence identity with PTAP. Aligned amino acid residues marked overtop with '*'.

FIG. 8 shows the phosphatase activity and detection of PTAP-related in potato and rice tissues. The bar graph indicates the phosphatase activity ($\mu$moles Pi produced/mg/min) of clarified crude protein extracts of potato tuber pith, potato tuber skin, potato stolon, potato root, potato leaf, rice seedling root and rice seedling leaf respectively. Phosphatase activity was measured by assay B. Under each enzyme activity bar are the polypeptides recognized by affinity purified anti-PTAP polyclonal IgG in the tissue sample. Samples were subjected to SDS-PAGE using a separating gel concentration of 10% (w/v) according to the method of Laemmli (1970), the gel was blot-transferred to polyvinylidene difluoride membrane and the membrane was treated with sodium-m-periodate and sodium borohydrate to disrupt the antigenicity of any glycosylation groups. All lanes contain 10 $\mu$g of the clarified protein extracts listed above. The blot was probed with anti-PTAP antibodies and visualized. The molecular weights of the immunologically detected PTAP-related are 57 and 55 kD in all potato tissues. However, potato root and stem possess an additional 52 kD polypeptide. The molecular weight of rice root and leaf PTAP-related polypeptides is 42 and 40 Kd.

FIGS. 9A and 9B show the partial sequence data for potato genomic clones PTAP-1 (SEQ ID NO:13) and PAP5 (SEQ ID NO:14). The underlined region of PTAP-1 shows nucleotide sequence identity with PTAP-2.

FIG. 10 is the DNA sequence data for potato genomic phosphatase clone PAP7 (SEQ ID NO:13) subclone 7-1.7. Underlined regions show exons.

FIG. 11 is the DNA sequence for genomic phosphatase clone PAP11 (SEQ ID NO:4) subclone 11-2.0. Underlined region shows exon.

FIGS. 12A and 12B show the DNA sequence for genomic phosphatase clone PTAP-2 (SEQ ID NO:1 showing the eight underlined exons that encode amino acid residues 39–451 of the full length PTAP protein.

FIGS. 13A and 13B shows the 5' to 3' sequence of oligonucleotides used as sequencing primers, oligonucleotide probes and PCR primers (primer 3–4a to RAP-5, SEQ ID NO:16 to SEQ ID NO:78, respectively).

Figure 5:
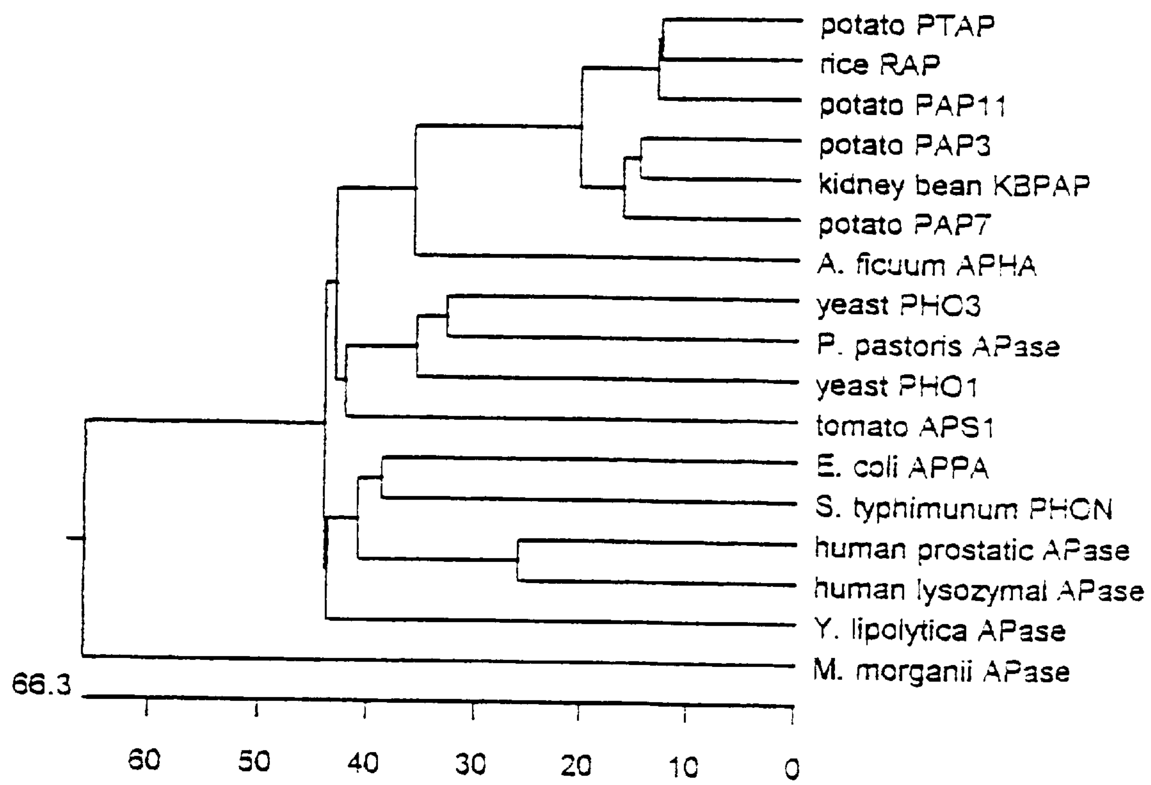
FIG. 5 illustrates the phylogenetic relationship of a number of representative enzymes exhibiting phosphatase activity. The CLUSTAL alignment and similarity index were assembled using amino acid sequence data (Higgins and Sharp, 1988). The sequences used were PTAP, PAP3, PAP7, PAP11, RAP, KBPAP, *Aspergillus ficuum* APHA (GenBank accession #U18553), tomato APS1 (M67474), yeast PHO1 (M11857), yeast PHO3 (X01080), *Pichia pastoris* APase (U28658), human lysozymal APase (X12548), human prostatic APase (M24902), *Eschericia coli* APPA (M58708), *Yarrowia lipolytica* APase (X65225), *Morganella morganii* APase (X78328) and *Salmonella typhimunum* PHON (X59036).

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

This invention relates to compositions and constructs comprising isolated nucleic acids (both DNA and RNA) encoding phosphatases and portions thereof of photosynthetic organisms. In particular, the genes encoding members of the major family of plant phosphatases from potato tubers and rice have been isolated and sequenced. Nucleic acids which encode potato phosphatases (PTAP, PAP3, PAP7, PAP11) and rice phosphatase (RAP), and homologues or analogs of these acid phosphatase nucleic acids, are encompassed by this invention. These phosphatases form a novel family of phosphatases. In particular, PTAP, PAP7, PAP11 and PAP are a highly-conserved group of enzymes.

The invention further relates to methods using isolated and/or recombinant nucleic acids (DNA or RNA) that are characterized by their ability to hybridize to (a) a nucleic acid encoding an phosphatase protein or polypeptide, such as a nucleic acid having any of the sequences of SEQ ID NO:1 (PTAP), SEQ ID NO:2 (PAP3), SEQ ID NO:3 (PAP7), SEQ ID NO:4 (PAP11), SEQ ID NO:5 (RAP) or (b) a portion of the foregoing (e.g., a portion comprising the minimum nucleotides required to encode a functional phosphatase protein; or by their ability to encode a polypeptide having the amino acid sequence of PTAP, PAP3, PAP7, PAP11, or RAP (e.g., SEQ ID NO:1, SEQ ID NO:2, SEQ ID NO:3, SEQ ID NO:4, or SEQ ID NO:5), or to encode functional equivalents thereof; e.g., a polypeptide which when incorporated into a plant cell, facilitates the uptake of phosphatase in the same manner as PTAP (SEQ ID NO:6), PAP3 (SEQ ID NO:7), PAP7 (SEQ ID NO:8), PAP11 (SEQ ID NO:9), or RAP (SEQ ID NO:10); or by both characteristics. A functional equivalent of PTAP, PAP3, PAP7, PAP11, or RAP, therefore, would have a similar amino acid sequence and similar characteristics to, or perform in substantially the same way as, a PTAP, PAP3, PAP7, PAP11, or RAP protein. A nucleic acid which hybridizes to a nucleic acid encoding a PTAP, PAP3, PAP7, PAP11, or RAP polypeptide such as SEQ ID NO:1, SEQ ID NO:2, SEQ ID NO;3, SEQ ID NO:4, or SEQ ID NO:5, can be double- or single-stranded.

Hybridization to DNA such as DNA having the sequence SEQ ID NO:1, SEQ ID NO:2, SEQ ID NO;3, SEQ ID NO:4, or SEQ ID NO:5, includes hybridization to the strand shown or its complementary strand.

In one embodiment, the percent amino acid sequence similarity between a PTAP polypeptide such as SEQ ID NO:6, and functional equivalents thereof is at least about 50% (≧50%). In a preferred embodiment, the percent amino acid sequence similarity between a PTAP polypeptide and its functional equivalents is at least about 65% (≧65%). More preferably, the percent amino acid sequence similarity between a PTAP, PAP3, PAP7, PAP11, or RAP polypeptide and its functional equivalents is at least about 75%, and still more preferably, at least about 80%.

Isolated and/or recombinant nucleic acids meeting these criteria comprise nucleic acids having sequences identical to sequences of naturally occurring PTAP, PAP3, PAP7, PAP11, or RAP genes and portions thereof, or variants of the naturally occurring genes. Such variants include mutants differing by the addition, deletion or substitution of one or more nucleotides, modified nucleic acids in which one or more nucleotides are modified (e.g., DNA or RNA analogs), and mutants comprising one or more modified nucleotides.

Such nucleic acids, including DNA or RNA, can be detected and isolated by hybridization under high stringency conditions or moderate stringency conditions, for example, which are chosen so as to not permit the hybridization of nucleic acids having non-complementary sequences. "Stringency conditions" for hybridizations is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

High stringency hybridization procedures can (1) employ low ionic strength and high temperature for washing, such as 0.015 M NaCl/0.0015 M sodium citrate, pH 7.0 (0.1× SSC) with 0.1% sodium dodecyl sulfate (SDS) at 50° C.; (2) employ during hybridization 50% (vol/vol) formamide with 5× Denhardt's solution (0.1% weight/volume highly purified bovine serum albumin/0.1% wt/vol Ficoll/0.1% wt/vol polyvinylpyrrolidone), 50 mM sodium phosphate buffer at pH 6.5 and 5× SSC at 42° C.; or (3) employ hybridization with 50% formamide, 5× SSC, 50 mM sodium phosphate (pH 6.8), 0.1% sodium pyrophosphate, 5× Denhardt's solution, sonicated salmon sperm DNA (50 μg/ml), 0.1% SDS, and 10% dextran sulfate at 42° C., with washes at 42° C. in 0.2× SSC and 0.1% SDS.

By varying hybridization conditions from a level of stringency at which no hybridization occurs to a level at which hybridization is first observed, conditions which will allow a given sequence to hybridize with the most similar sequences in the sample can be determined.

Exemplary conditions are described in Krause, M. H. and S. A. Aaronson (1991) *Methods in Enzymology*, 200:546–556. Also, see especially page 2.10.11 in *Current Protocols in Molecular Biology* (supra), which describes how to determine washing conditions for moderate or low stringency conditions. Washing is the step in which conditions are usually set so as to determine a minimum level of complementarity of the hybrids. Generally, from the lowest temperature at which only homologous hybridization occurs, a 1% mismatch between hybridizing nucleic acids results in a 1° C. decrease in the melting temperature $T_m$, for any chosen SSC concentration. Generally, doubling the concentration of SSC results in an increase in $T_m$ of ~17° C. Using these guidelines, the washing temperature can be determined empirically for moderate or low stringency, depending on the level of mismatch sought.

Isolated and/or recombinant nucleic acids that are characterized by their ability to hybridize to (a) a nucleic acid encoding a PTAP, PAP3, PAP7, PAP11, or RAP polypeptide, such as the nucleic acids depicted as SEQ ID NO:1, SEQ ID NO:2, SEQ ID NO:3, SEQ ID NO:4 or SEQ ID NO:5, (b) the complement of SEQ ID NO:1, SEQ ID NO:2, SEQ ID NO:3, SEQ ID NO:4 or SEQ ID NO:5, (c) or a portion of (a) or (b) (e.g. under high or moderate stringency conditions), may further encode a protein or polypeptide having at least one function characteristic of a PTAP, PAP3, PAP7, PAP11, or RAP polypeptide, such as translocation activity (e.g., transport of β-lactamase across a bacterial cell membrane), or binding of antibodies that also bind to non-recombinant PTAP, PAP3, PAP7, PAP11, or RAP. The catalytic or binding function of a protein or polypeptide encoded by the hybridizing nucleic acid may be detected by standard enzymatic assays for activity or binding (e.g., assays which measure the binding of a transit peptide or a precursor, or other components of the translocation machinery). Enzymatic assays, complementation tests, or other suitable methods can also be used in procedures for the identification and/or isolation of nucleic acids which encode a polypeptide such as a polypeptide of the amino acid sequence SEQ ID NO:6, SEQ ID NO:7, SEQ ID NO:8, SEQ ID NO:9, or SEQ ID NO:10, or a functional equivalent of this polypeptide. The antigenic properties of proteins or polypeptides encoded by hybridizing nucleic acids can be determined by immunological methods employing antibodies that bind to a PTAP, PAP3, PAP7, PAP11, or RAP polypeptide such as immunoblot, immunoprecipitation and radioimmunoassay. PCR methodology, including RAGE (Rapid Amplification of Genomic DNA Ends), can also be used to screen for and detect the presence of nucleic acids which encode PTAP, PAP3, PAP7, PAP11, or RAP-like proteins and polypeptides, and to assist in cloning such nucleic acids from genomic DNA. PCR methods for these purposes can be found in Innis, M. A., et al. (1990) *PCR Protocols: A Guide to Methods and Applications*, Academic Press, Inc., San Diego, Calif., incorporated herein by reference.

The nucleic acids described herein are used in the methods of the present invention for production of proteins or polypeptides which are incorporated into cells, tissues, plant parts, plants and other photosynthetic organisms. In one embodiment, DNA containing all or part of the coding sequence for a PTAP, PAP3, PAP7, PAP11, or RAP polypeptide, or DNA which hybridizes to DNA having the sequence SEQ ID NO:1, SEQ ID NO:2, SEQ ID NO:3, SEQ ID NO:4 or SEQ ID NO:5 is incorporated into a vector for expression of the encoded polypeptide in suitable host cells. The encoded polypeptide consisting of PTAP, PAP3, PAP7, PAP11, or RAP, or its functional equivalent is capable of phosphatase activity. The term "vector" as used herein refers to a nucleic acid molecule capable of transporting another nucleic acid to which it has been linked.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow or make probable a desired recombination event. Portions of the isolated nucleic acids which code for polypeptides having a certain function can be identified and isolated by, for example, the method of Jasin, M., et al., U.S. Pat. No. 4,952,501.

A further embodiment of the invention is antisense nucleic acids or oligonucleotides which are complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acids or oligonucleotides can inhibit the expression of the gene encoded by the sense strand or the mRNA transcribed from the sense strand. Antisense nucleic acids can be produced by standard techniques. See, for example, Shewmaker, et al., U.S. Pat. No. 5,107,065.

In a particular embodiment, an antisense nucleic acid or oligonucleotide is wholly or partially complementary to and can hybridize with a target nucleic acid (either DNA or RNA), wherein the target nucleic acid can hybridize to a nucleic acid having the sequence of the complement of the strand in SEQ ID NO:1, SEQ ID NO:2, SEQ ID NO:3, SEQ ID NO:4 or SEQ ID NO:5. For example, an antisense nucleic acid or oligonucleotide can be complementary to a target nucleic acid having the sequence shown as the strand of the open reading frame of SEQ ID NO:1, SEQ ID NO:2, SEQ ID NO:3, SEQ ID NO:4 or SEQ ID NO:5, or nucleic acid encoding a functional equivalent of PTAP, PAP3, PAP7, PAP1, or RAP, or to a portion of these nucleic acids sufficient to allow hybridization. A portion, for example, a sequence of 16 nucleotides could be sufficient to inhibit expression of the protein. Or, an antisense nucleic acid or oligonucleotide complementary to 5' or 3' untranslated regions, or overlapping the translation initiation codon (5' untranslated and translated regions), of the PTAP, PAP3, PAP7, PAP11, or RAP gene, or a gene encoding a functional equivalent can also be effective. In another embodiment, the antisense nucleic acid is wholly or partially complementary to and can hybridize with a target nucleic acid which encodes a PTAP, PAP3, PAP7, PAP11, or RAP polypeptide.

In addition to the antisense nucleic acids of the invention, oligonucleotides can be constructed which will bind to duplex nucleic acid either in the gene or the DNA:RNA complex of transcription, to form a stable triple helix-containing or triplex nucleic acid to inhibit transcription and/or expression of a gene encoding PTAP, PAP3, PAP7, PAP11, or RAP, or its functional equivalent. Frank-Kamenetskii, M. D. and Mirkin, S. M. (1995) *Ann. Rev. Biochem*. 64:65–95. Such oligonucleotides of the invention are constructed using the base-pairing rules of triple helix formation and the nucleotide sequence of the gene or mRNA for PTAP, PAP3, PAP7, PAP11, or RAP. These oligonucleotides can block PTAP, PAP3, PAP7, PAP11, or RAP-type activity in a number of ways, including prevention of transcription of the PTAP, PAP3, PAP7, PAP11, or RAP gene or by binding to mRNA as it is transcribed by the gene.

Proteins

The invention also relates to proteins or polypeptides encoded by the novel nucleic acids described herein. The proteins and polypeptides of this invention can be isolated and/or recombinant. Proteins or polypeptides referred to herein as "isolated" are proteins or polypeptides purified to a state beyond that in which they exist in cells. In a preferred embodiment, they are at least 10% pure; i.e., substantially purified. "Isolated" proteins or polypeptides include proteins or polypeptides obtained by methods described infra, similar methods or other suitable methods, and include essentially pure proteins or polypeptides, proteins or polypeptides produced by chemical synthesis or by combinations of biological and chemical methods, and recombinant proteins or polypeptides which are isolated. Proteins or polypeptides referred to herein as "recombinant" are proteins or polypeptides produced by the expression of recombinant nucleic acids.

In a preferred embodiment, the protein or portion thereof has at least one function characteristic of an phosphatase, for example, catalytic activity (e.g., catalysis of phytate degradation, catalysis of dephosphorylation of phosphoproteins such as phosphocasein or P-Tyr), binding function, and/or antigenic function (e.g., binding of antibodies that also bind to naturally occurring phosphatases). As such, these proteins are referred to as phosphatases of plant origin, and include, for example, naturally occurring PTAP, variants (e.g. mutants) of those proteins and/or portions thereof. Such variants include mutants differing by the addition, deletion or substitution of one or more amino acid residues, or modified polypeptides in which one or more residues are modified, and mutants comprising one or more modified residues.

The invention also relates to isolated and/or recombinant portions of an phosphatase as described above. Portions of the enzyme can be made which have full or partial function on their own, or which when mixed together (though fully, partially, or nonfunctional alone), spontaneously assemble with one or more other polypeptides to reconstitute a functional protein having at least one functional characteristic of an phosphatase of this invention.

Plants

The nucleic acids and encoded products of this invention can be used to modify and modulate phosphatase activity in any photosynthetic organism. Thus, the organisms encompassed by this invention include members of the Plant Kingdom, photosynthetic protists and the algae. The term "plant" includes the seed-bearing angiosperms (both dicots and monocots) and gymnosperms, and non-seed bearing multicellular organisms such as ferns, bryophytes and mosses. Of special interest for modification using the constructs and methods of this invention are the crop and horticultural plants. Examples of preferred monocotyledons include rice, corn, wheat, rye, barley, sugar cane and sorghum. Examples of preferred dicotyledons include canola, potato, pea, soybeans, sunflower, tobacco, cotton, sugar beet, petunia, tomato, broccoli, lettuce, apple, plum, orange, lemon, and rose. Other photosynthetic organisms which can be hosts for the constructs of this invention include the multicellular and single-celled eukaryotic algae and the prokaryotic blue-green algae (cyanophyta). Those of skill in the art can recognize the examples given above are not limiting. Whether through soil or through hydroponics, phosphate uptake and metabolism can be modified in all of the above-described organisms using the constructs of this invention.

Further, non-photosynthetic bacteria and fungi, such as yeasts, can be transformed with the nucleic acid constructs of this invention to produce recombinant host cells which overexpress phosphatase. The phosphatase obtained through the processes of fermentation is useful for industrial applications.

Constructs

A recombinant DNA construct, such as a vector, expresses a protein in a cell of a photosynthetic organism, the construct comprising a coding region for the protein operably linked with a control region comprising a promoter which promotes expression of the protein in the host cell. Those of skill in the art can appreciate that both constitutive and tissue-specific promoters can be used in recombinant DNA constructs to drive expression of the nucleic acids of this invention, and can be operably linked and incorporated into vectors useful for the expression of these nucleic acids. Constitutive promoters drive expression throughout the cells and tissues of an organism; whereas, tissue-specific promoters express the linked nucleic acids in specific cells or tissues. The promoter in the construct can be an inducible promoter, so that expression of the sense or antisense molecule in the construct can be controlled by exposure to the inducer. Other control elements needed for expression or activity, such as a 3' termination region, can be included as part of the construct.

Any suitable method can be used to introduce these constructs into plant cells. The methods of introduction of the nucleic acids of this invention will vary with the species of organism and the type of expression or activity to be induced. Methods of regenerating whole plants from plant cells are known in the art (See, e.g., *Plant Molecular Biology Manual*, (Eds. S. B. Gelvin, R. A. Schilperoort) Kluwer Acad. Publishers (1988), and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Overexpression of phosphatase itself can be used as a marker to detect plants with the ability to grow more efficiently under conditions of phosphate deprivation. For example, a method of detecting transformation in plants, plant tissue or a photosynthetic organism can consist of preparing a DNA construct comprising a promoter operably-linked to a nucleic acid encoding an phosphatase having at least 50% sequence similarity to SEQ ID NO:6. The construct can be inserted into a vector and used to transform a plant, tissue culture or photosynthetic organism so that the phosphatase is expressed and the ability of the plant, tissue culture or photosynthetic organism to grow in an environment low in phosphate is enhanced. The growth in an environment low in phosphate is indicative of transformation. This type of marker obviates the need for antibiotic resistance type markers and other detection mechanisms which are foreign to plant cells.

Once callus forms, shoot formation can be encouraged by employing the appropriate plant hormones in accordance with known methods and the shoots transferred to rooting medium for regeneration of plants. The plants can then be used to establish repetitive generations, either from seeds or using vegetative propagation techniques.

The constructs of this invention can be incorporated into protoplasts, single-celled organisms, cells and tissues derived from multicellular organisms and plant parts. Suitable plant parts include, for example, pollen, ovaries, seeds, embryos, hypocotyls, epicotyls, cotyledons, leaves, stems, roots, flowers, meristems, tissue, protoplasts and explants. New plants can be regenerated from these transformed cells, tissues and plant parts, explants or any other portion of the plant which is suitable for regeneration using standard regeneration techniques. Tissue culture of transgenic cells can also be maintained and used to produce plant products.

Seed of transgenic plants are provided by this invention and can be used to propagate more plants containing the constructs of this invention. Transgenic plants produced from such seed can be crossed with other plants using breeding methods known to those of skill in the art to produce transgenic plants with new characteristics in addition to the characteristics imparted by the expression of the incorporated nucleic acids of this invention. These descendants are intended to be included in the scope of this invention if they contain the constructs of this invention, whether or not these plants are selfed or crossed with different varieties of plants.

Purification and Physical Properties of Potato Tuber Phosphatase

Phosphatase activity occurs extensively in all plant species. Within a species, distinct isozymes have been shown to occur in different tissues and developmental stages or to coexist. These phosphatase isozymes have often been shown to be different in their physical, biochemical and expressional properties (Duff et al, 1994). In spite of such variability, there are some physiological and biochemical similarities among the plant phosphatases. Antibodies raised against one phosphatase, PEP phosphatase, recognized proteins of a relatively similar size in a number of plant species (Duff et al, 1991b). These same antibodies failed to cross-react with any human, yeast, algal or bacterial proteins.

As an initial step towards the isolation of plant phosphatase genes, the predominant phosphatase from potato tuber was purified to a final P-Tyr-hydrolyzing specific activity of 1917 units/mg (Gellatly et al, 1994). Only a single peak of activity was recovered following chromatography on columns of S-Sepharose, phosphocellulose and Phenyl Superose (Gellatly et al, 1994). One unit is defined as the $\mu$moles of Pi produced per min at 25° C. The enzyme was purified 2289-fold to a final PEP-hydrolyzing specific activity of 618 units/mg and an overall recovery of 31% (Gellatly et al, 1994). With P-Tyr as substrate the final specific activity was increased to approximately 1900 units/mg (Table 1). This final specific activity was higher than any reported for a purified plant phosphatase (Duff et al, 1994).

Gel electrophoresis and native molecular mass estimation

The native molecular mass of the purified enzyme was estimated by nondenaturing SDS-PAGE to be approximately 100 kD. A single protein-staining band that co-migrated with APase activity was observed following nondenaturing PAGE of the final preparation. However, when the final preparation was denatured and subjected to SDS-PAGE, two protein-staining bands with molecular masses of about 57 and 55 kD were observed. Densitometric scanning indicated that the 57- and 55-kD protein-staining bands occurred in a ratio of approximately 2:1, respectively. Both polypeptides were determined to be associated with native potato phosphatase for the following reasons: (a) these two protein-staining bands co-eluted following Superose 12 gel filtration FPLC of the final preparation; (b) the single band from nondenaturing PAGE still produced two bands after SDS-PAGE; (c) the respective patterns of peptide fragments produced after limited treatment with cyanogen bromide are quite comparable, as analyzed by SDS-PAGE, and (d) both polypeptides are immunologically related. These data suggest that the native enzyme existed as a either a homo- or heterodimer.

TABLE 1

Substrate specificity of potato phosphatase.

| Substrate | $V_{max}$ (units/mg) | $K_m$ (mM) | Specificity Constant ($V_{max}/K_m$) |
|---|---|---|---|
| P-Tyr | 1917 | 0.99 | 1936 |
| p-nitrophenyl-P | 1250 | 1.10 | 1136 |
| P-Ser | 389 | 0.62 | 627 |
| PEP | 764 | 1.52 | 503 |
| PPi | 1728 | 4.42 | 391 |
| MgATP | 368 | 2.16 | 170 |
| P-Tbr | 99 | ND[a] | ND |
| Mg-ADP | 46 | ND | ND |

All parameters were determined using phosphatase assay B using purified potato phosphatase.
[a]ND, not determined.

Heat-stability

The phosphatase was relatively heat-stable, losing 0, 52, and 90% of its original activity when incubated for 4 min at 65, 70 and 75° C., respectively.

Immunological characterization

An immunobolot of the final phosphatase preparation that had been pre-treated with sodium m-periodate was probed with affinity-purified rabbit anti-(black mustard PEP-specific phosphatase) IgG (Duff et al, 1991) and revealed 57- and 55-kD immunoreactive polypeptides that stained in a >2:1 ratio.

The same result was obtained following immunoblotting of a clarified potato extract that had been prepared in the absence of protease inhibitors and incubated at 25° C. for 0 and 16 h. Identical antigenic polypeptides were observed on immunoblots of clarified potato extracts prepared in the presence of 12 different protease inhibitors or in hot (90° C.) SDS-PAGE sample buffer. These data demonstrate that (a) the 55-kD polypeptide observed after SDS-PAGE or immunoblotting of the final phosphatase preparation was not a proteolytic degradation product of the 57-kD protein, and (b) both polypeptides are stable in the absence of added protease inhibitors and are structurally related to the PEP-specific phosphatase from black mustard suspension cells. It also demonstrates that the amounts and ratio of the 57- and 55-kD proteins remains constant in sprouting (soft) tubers that had been stored for several months at room temperature. The same antibodies have previously been demonstrated to effectively immunoprecipitate the activity of a commercially available preparation of potato tuber phosphatase (Duff et al, 1991a).

Kinetic Studies

Unless otherwise stated all kinetic studies of the potato phosphatase were performed with PEP using assay A (infra).

Effect of pH

The enzyme showed a fairly broad pH/activity profile, with a maximum occurring at about pH 5.8. Half-maximal activity was observed at pH 4.9 and 6.7. All subsequent kinetic studies were carried out at pH 5.8.

Effect of Divalent Cations

The phosphatase was activated approximately 40% in the presence of saturating (4 mM) $Mg^{2+}$ (added as $MgCl_2$). $Ca^{2+}$, $Co^{2+}$, and $Mn^{2+}$ were individually tested as $Cl^-$ salts at 4 mM, with no added $Mg^{2+}$, and found to uniformly activate the enzyme by about 30%. When the reaction mixture contained 5 mM EDTA and no added $Mg^{2+}$, the activity was reduced by about 65%. When tested in place of added $Mg^{2+}$, 5 mM $ZnCl_2$ completely inhibited phosphatase activity. All subsequent kinetic studies were conducted in the presence of 4 mM $MgCl_2$.

Substrate Specificity

Phosphatase activity was determined using assay B and a wide range of compounds, tested at a total concentration of 5 mM unless otherwise specified. The purified enzyme showed little or no activity with AMP, and Glc-1-P.

Table 1 lists $V_{max}$ and apparent $K_m$ values, along with specificity constants ($V_{max}/K_m$), for those compounds which were found to be dephosphorylated at a significant rate by the purified enzyme. The highest activity and specificity constant was obtained with P-Tyr. The specificity constant with P-Tyr was about three-fold greater than the value obtained with the next best non-artificial substrate, P-Ser. When the egg yolk storage phosphoprotein, phosvitin, was tested at a concentration of 50 $\mu$g/ml (125 ηM), a phosphoprotein phosphatase activity of 220 units/mg was obtained.

Metabolite and ion Effects

A wide variety of substances were tested for effects on the purified enzyme using subsaturating concentrations of PEP (0.25 mM) as substrate. Table 2 lists those compounds which were found to inhibit phosphatase activity. The most notable inhibitors were vanadate, molybdate, phytate, phosvitin, and NaPi. The following substances had no effect (±15% control activity) on enzyme activity: NaCl, KCl, $NH_4Cl$, Mg-citrate and tartrate (all 5 mM); cAMP (100 $\mu$M); $Ca^{2+}$/bovine calmodulin (50 $\mu$M/1 $\mu$M); and okadaic acid (1 $\mu$M). Preincubation of enzyme with 1 mM N-ethylmaleimide for up to 2 min at 25° C. also had no effect on enzyme activity. GSH (5 mM) activated phosphatase activity by 30%.

TABLE 2

Effect of various substances on the activity of potato phosphatase.

| Addition | Concentration (mM) | Relative Activity (%) |
|---|---|---|
| Vanadate | 0.05 | 7 |
| | 0.005 | 40 |
| Molybdate | 1 | 0 |
| | 0.01 | 7 |
| | 0.001 | 40 |
| EGTA | 5 | 72 |
| EDTA | 5 | 32 |
| NaPi | 0.5 | 44 |
| NaF | 5 | 56 |
| Glutaamate | 5 | 30 |
| Asparatate | 5 | 64 |
| Ascorbate | 5 | 12 |
| Phytate | 0.1 | 48 |
| GSH | 5 | 131 |
| Phosvitin | 0.001 | 19 |

The standard phosphatase assay A was used, except that the concentration of PEP was subsaturating (0.25 mM). Enzyme activity in the presence of effectors is expressed relative to the control set at 100%.

Zhao and coworkers (1992) recently reported that the dephosphorylation of P-Tyr by potato phosphatase occurs at a rate comparable to that of several human P-Tyr protein phosphatases. This finding is in accord with the relatively high activity and specificity of potato phosphatase for P-Tyr that was observed in the present study (Table 1), a property that distinguishes it from most other plant phosphatases that have been examined to date (Duff et al, 1994). The capacity of potato phosphatase to dephosphorylate a variety of phosphoproteins in this and other studies (Bingham et al, 1976; Chen and Blenis, 1990) demonstrates that such an activity may have physiological relevance. Ser is the predominant phosphorylated amino acid of the egg yolk storage protein, phosvitin (Byrne et al, 1984), and other phosphoproteins that have been reported to serve as substrates for potato phosphatase (Bingham et al, 1976; Chen and Blenis, 1990). The data herein show, however, that similar to other plant tissues (Elliot and Geytenbeek, 1985) there is an abundance of P-Tyr-containing polypeptides in potato tubers. Monospecific anti-(P-Tyr) polyclonal antibodies (Kamps and Sefton, 1988) were used to identify proteins phosphorylated on Tyr in potato tuber extracts. Numerous potato tuber polypeptides appear to be phosphotyrosylated. No antigenic polypeptides were observed when an immunoblot of a potato extract was probed with the P-Tyr antibodies in the presence of 20 mM P-Tyr. Moreover, incubation of a desalted tuber extract in the presence of the purified potato phosphatase caused a substantial reduction in the level of phosphorylation of several of the endogenous P-Tyr proteins (Table 3). Since this decrease in protein P-Tyr content was not caused by protein degradation and was negated by the presence of 1 mM o-vanadate, these observations suggest that the major potato phosphatase can dephosphorylate endogenous P-Tyr proteins in vitro. Several recent studies have demonstrated that the composition and length of the amino acid sequence adjacent to the phosphotyrosylation site markedly influences the affinity and specificity of a P-Tyr protein phosphatase for its substrate (Cho et al, 1991; Ramachandran et al, 1992; Zhang et al, 1993). For example, a P-Tyr phosphatase from *Escherichia coli* has a $K_m$ (P-Tyr) of more than 6 mM, but displays $k_m$ values ranging from 0.027 to 4.1 mM for various P-Tyr peptides (Cho et al, 1991). Thus, the $K_m$ (P-Tyr) of 0.99 mM derived for potato phosphatase may be orders of magnitude in excess of the enzyme's $K_m$ value for P-Tyr peptides and/or endogenous phosphoprotein substrates.

TABLE 3

Dephosphorylation of potato tuber phosphotyrosyl proteins by potato tuber phosphatase.

| Estimated Molecular Mass of Phosphotyrolated | Relative phosphotyrosyl content after Incubation at 25" C | | | |
|---|---|---|---|---|
| | 2h | | 19h | |
| | − | + | − | + |
| kD | % initial value | | | |
| 102 | 76° | 60 ± 5 | 51 ± 5 | 36 ± 3 |
| 85 | 85 ± 9 | 69 ± 2 | 60+4 | 34 ± 2 |
| 34 | 93 ± 6 | 40 ± 3 | 38° | 16 + 2 |
| 228.5 | 81° | 65 ± 2 | 31 ± 5 | 28 ± 3 |
| 20 | 83" | 66 ± 5 | 18 ± 1 | 12 ± 3 |

A desalted potato tuber extract was incubated at 25° C. in the absence (−) and presence (+) of 30 units/mL purified potato tuber phosphatase. Aliquots were removed at 2 and 19 h and analyzed by immunoblotting using anti-(P-Tyr) IgG (Kamps and Sefton, 1988). The relative P-Tyr content of the 7 antigenic polypeptides was estimated by laser densitometric quantification of the immunoblots as described in the examples. Unless otherwise noted, all values represent the means±SE of triplicate determinations. [a], the mean of duplicate determinations.

Several P-Tyr phosphatases from plant sources, including poppy seeds (Chung and Polya, 1992), wheat seedlings (Cheng and Tao, 1989), and maize seedlings (Jagiello et al, 1992), have been characterized. The subunit composition and substrate specificity of the potato tuber phosphatase most closely resembles that of the poppy seed enzyme (Chung and Polya, 1992). In addition, Polya and Wettenhall (1992) have described the purification and characterization of a minor 28-kD potato tuber phosphatase isoform that also effectively hydrolyzes Pi from P-Tyr. This minor potato phosphatase isoform is clearly distinguishable from the phosphatase of this invention by subunit structure, a P-Tyr-hydrolyzing specific activity of only 103 units/mg, its inability to catalyze dephosphorylation of P-Ser, and its inhibition by micromolar concentrations of cAMP (Polya and Wettenhall, 1992).

Similar to the potato phosphatase, nonplant PTPases (mammalian and yeast P-Tyr phosphatases (PTPases)) frequently display an acidic pH optimum, show potent inhibition by o-vanadate, molybdate and $Zn^{2+}$, and will catalyze the dephosphorylation of p-nitrophenyl-P as well as a variety of other phosphomonoesters (Ballou and Fischer, 1986; Chen and Blenis, 1990; Brautigan, 1992; Charbonneau and Tonks, 1992; Cho et al, 1991; Lau et al, 1989; Pot and Dixon, 1992). However, PTAP is an unlikely member of the PTPase family due to failed attempts to identify related plant genes and proteins, the tendancy of PTPases to be transmembrane proteins and the broad range substrates that serve as PTAP substrates.

The purification and extensive characterization of potato tuber phosphatase (PTAP) (Gellatly et al, 1994) represents one of the most thorough characterizations of an abundant plant phosphatase. The study showed that PTAP had the highest activity observed of any phosphatase on non-artificial substrates (Duff et al, 1994). PTAP also showed that it could readily hydrolyze free P-Tyr and phosphotyrosylated proteins (Gellatly et al, 1994). P-Tyr hydrolyzing is largely associated only with the homologous family of protein tyrosine phosphatases (PTPases) involved in the regulation of yeast and animal cell growth and differentiation (Walton and Dixon, 1993). No members of the PTPases family have been found in plants despite attempts to screen libraries with anti-PTPase antibodies and DNA sequences that recognize conserved PTPase domains (Pot and Dixon, 1992). However, the abundance of plant phosphotyrosylated proteins (Gellatly et al, 1994; and Elliot and Gettenbeek, 1985) argues that P-Tyr hydrolyzing enzymes exist in plants. The isolation of some plant P-Tyr hydrolyzing enzymes shows this is the case (Gellatly et al, 1994; Cheng and Tao, 1989). The enzymatic and structural relatedness of PTAP and other plant major phosphatases has been clearly demonstrated (Duff et al, 1994), but, until now, no genes coding for these proteins had been identified.

Generation of PTAP Fragments by Cyanogen Bromide and Trypsin Digestion

The purification to homogeneity of PTAP enabled the generation of microsequence protein data. Although PTAP was partially $NH_2$-terminally blocked, purified PTAP was subjected to digestion with cyanogen bromide, separated by SDS-PAGE and blotted to PVDF membrane. Table 4 shows the sequence of three cyanogen bromide fragments; M-1, M-2 and M-3. In addition, purified PTAP was dotted onto PVDF membrane and submitted to Harvard Microchem (Cambridge, Mass., USA) for microsequencing following trypsin digestion. The sequences of fragments K/R-46, K/R-39, K/R-28, K/R-22 and K/R-20 are given in Table 4. Initial data base searches indicated no close homology to any known protein sequences.

TABLE 4

Potato tuber phosphatase (PTAP) microsequenced protein fragments

| Peptide designation | Amino acid sequence |
|---|---|
| N-term | SQFPsMNI |
| K/R-46 | VLFVGDLSYADRYQYNDVGVR |
| K/R-39 | KF?FETPPKVDPDASYK |
| K/R-28 | NDDGN?!TtDSFtLHNqy |
| K/R-22 | FRDPQPEYSAFR |
| K/R-20 | tGFP?VSGG?AYPVPt/gk |
| M-1 | tGFP?V?!PLe |
| M-2 | RQFPIv/dDIPLEn?v |
| M-3 | MESAYEVw/dFVKYKVDVIFAG |

Amino acid residues are represented by their single letter designation. Lower case letters indicate uncertainty while N-'/' indicates an amino acid is one of the two residues. N-term refers to the PTAP $NH_2$-terminus microsequencing performed on 1 ηmole (60 μg) pure enzyme spotted onto polyvinylidene difluoride membrane as a service by Queen's University Core facility (Kingston, ON). K/R fragments were generated by digestion with trypsin of 60 μg pure PTAP applied to polyvinylidene difluoride membrane, followed by separation by HPLC and microsequencing by Harvard Microchem (Cambridge, Mass.). M fragments were prepared by digestion of 60 μg pure PTAP according to the method of Plaxton and Moorhead (1989) and transferred to polyvinylidene fluoride after separation by 14% (w/v) SDS-PAGE according to the method of Laemmli (1970). Isolated bands were microsequenced by Queen's University Core facility (Kingston, ON).

Isolation of Potato Genomic Clones PAP1 and PAP5

To screen an λEMBL3 potato genomic library for phosphatase clones, a single stranded degenerate probe was constructed based on microsequenced protein data. The fragment K/R-39 (Table 4) was chosen since it had the uninterrupted sequence 'FETPPKVDPDA' and contained five residues with only 2 possible codons (F, E, K and D).

The oligonucleotide was constructed with inosine substituted at the wobble positions of Thr, Pro and Val which each have four possible codons. Inosine binds with equal energy to the deoxynucleotides A, T and C and therefore has little effect on primer degeneracy unless mismatched with a G. Potato codon bias, as determined using the internet CUTG codon usage database, suggested there were relatively equal occurrences of all codons for Phe, Glu, Lys, Val, and Asp. ACG (Thr) and CCG (Pro) codon usage was 6.3% and 7.6% respectively; however, since both these codons end with 'G', an inosine residue at the third position would have only a small chance at contributing to primer degeneracy. The inclusion of the first two nucleotides 'GC' of the final A residue had no effect on primer degeneracy. The sequence of the 39f oligonucleotide probe, 5'TTT/C GAA/G ACI CCI CCI AAA/G GTI GAT/C CCI GAT/C GC3' had a degeneracy of 32 and a minimum melting temperature of 59.2° C. in 1× SSC (0.195 M $Na^+$) using the formula $Tm=81.5+16.6(\log_{10}[Na^+])+0.41(\%GC)-500/L$ where % GC=40.6 and 1=32. Seven consecutive fluorescein-phosphoramidite bases were added during synthesis to facilitate luminescent detection of bound mouse anti-fluorescein IgG coupled to anti-mouse IgG coupled to alkaline phosphatase in Dupont Renaissance luminol reagent.

The degenerate probe was used to screen 200,000 pfu of an λEMBL3 potato genomic library at high stringency. Two clones, PAP1 and PAP5, were selected until homogeneous through four successive screenings, amplified and purified. Genomic DNA inserts were recovered from agarose gels following digestion with XhoI. There does not appear to be any overlap between PAP1 and PAP5. A southern blot of PAP1 and PAP5 restriction fragments probed with 39f was done. The detected restriction fragments to be subcloned were the PAP1 2.1 kb (EcoRI and HindIII) fragment and the PAP5 1.9 kb (EcoRI and EglII) fragment. These fragments were subcloned into pBluescript and purified. Partial sequencing revealed no significant homology to any sequence data bank entries.

Isolation of Rice Suspension Culture cDNA Clone RAP and Potato Genomic Clones PTAP, PAP3, PAP7 and PAP11

TBLASTX Homology

Protein and nucleotide databases were routinely searched for homology to PTAP fragment microsequence data using BLASTP and TBLASTX internet-based search protocols. Random sequencing of a rice suspension culture cDNA yielded two rice partial cDNA sequences (Uchimiya et al, 1992) that showed significant homology with PTAP fragments K/R-46 and M-1 when translated into protein data by TBLASTX. C2251_1A (GenBank accession number D23223) and C0554A (GenBank accession number D15378) aligned with K/R-46 and M-1 respectively as follows:

K/R-46 DLSYADRYQYN consensus D SYADRYQ+N

C2251_1A D?SYADRYQHN

M-3 MESAYEVWFVKYKVDVIFAG consensus M+A+E WFVKYKVD++FAG

C0554A MRAAFEKWFVKYKVDLVFAG where the consensus amino acids show sequence identity and '+' indicates a conserved substitution. Alignment of C2251_1A and C0554A revealed that these sequences overlapped to produce a contiguous 531 bp sequence coding for 177 amino acid residues. K/R-46 and M-1 homology existed to the +1 reading frame of the rice cDNA sequence. Data bank searches for homology to the putative rice phosphatase (RAP) sequence revealed no significant alignments.

Rice Phosphatase Probe

To generate a probe with which to isolate phosphatase clones, the genomic RAP sequence was amplified using PCR. Genomic DNA was extracted from *Orysa sativa* cv. Japonica plantlets and used at a concentration of 1 ηg/μL during PCR amplification. Two sets of PCR oligonucleotide primers and an additional internal primer were constructed using the PrimerSelect program. Primers 1 and 2 were the outermost set expected to amplify the genomic equivalent of the 470 bp of the RAP sequence. Primers 3 and 4, internal to 1 and 2, were expected to amplify a genomic sequence corresponding to 360 bp of the RAP cDNA. Primer 5 was to be used in a PCR reaction with primers 2 or 4 and as a single stranded probe to test PCR products. FIG. 8*a*-lane 1 shows the single 1.5 kb PCR product generated from primers 3 and 4 at 50° C. annealing temperature using standard conditions. FIG. 8*a*-lane 3 shows the 780 bp product resulting from a PCR reaction utilizing 1 ηg/μL of the 1.5 kb band as template and primers 5 and 4. Primers 1 and 2 failed to produce a rice genomic PCR sequence (Figure a-lane 2). FIG. 8*b*-lane 1 demonstrates that in a Southern blot with $^{32}P$-labelled primer 5, the 1.5 kb primer 3 and 4 PCR product was detected with a similar intensity to the primer 5 and 4 PCR product (FIG. 8*b*-lane 3). 16 μg of the 1.5 kb putative rice phosphatase PCR product was generated for screening of rice and potato cDNA libraries and a potato genomic library.

The 1.5 kb rice genomic PCR product was labelled with $^{32}P$ and used as a probe to screen the rice suspension culture cDNA library from which clones C2251_1A and C0554A were derived. $1\times10^5$ pfu were initially screened at maximum stringency. Four identical cDNA clones were enriched to homogeneity and subcloned into pBluescript at the EcoRI restriction site. FIG. 2 shows the 1176 kb RAP cDNA sequence with a 850 nucleotide open reading frame coding for 283 amino acids. Comparison of RAP with the contiguous sequence of C2251_1A and C0554A revealed the sequences were virtually identical in the region of overlap. The few observed sequence discrepancies are likely due to C2251_1A and C0554A each being derived from one automated sequence.

Isolation of Potato Genomic Clones $1\times10^5$ pfu of an λEMBL3 potato genomic library was screened for phosphatase clones using the $^{32}P$-labelled 1.5 kb rice genomic PCR probe. Hybridization and low stringency washes were conducted at 50° C. to facilitate identification of clones with greater than 85% sequence homology. Potato genomic clones designated PAP3, PAP4, PAP7, and PAP11 were rescreened until homogenous, followed by amplification and purification. Restriction digestion patterns and Southern blot of the genomic clones indicated that they were distinct. To facilitate sequence analysis, restriction fragments from four clones that annealed with the probe were gel purified and subcloned into pBluescript SK. The subcloned genomic fragments were,

| potato genomic clone | subcloned fragment |
|---|---|
| PAP3 | 4.0 kb (EcoRI and SalI) |
| PAP4 | 3.8 kb (BamHI and SalI) |
| PAP7 | 1.7 kb (BamHI and EcoRI) |
| PAP11 | 2.0 kb (BamHI and EcoRI) |

The potato genomic subclones were sequenced, analyzed for open reading frames and aligned with generated sequence data and sequence data from the sequence data banks. Sequence identity between PTAP microsequenced protein fragments K/R-39 and K/R-46 and the deduced amino acid sequence of the genomic PAP4 subclone 4-3.8, K/R-39 KF?FETPPKVDPDASYK
consensus KF FETPPKVDPDASYK
4-3.8 KFWFETPPKVDPDASYK
K/R-46 VLFVGDLSYADRYQYNDVGVR
consensus VLFVGDLSYADRYQYNDVGVR
4-3.8 VLFVGDLSYADRYQYNDVGVR indicated that PAP4 contained at least part of the PTAP gene and was hereafter designated PTAP-2. The exons assembled from the genomic sequence of PTAP-2 is given in FIG. 4. Although the restriction maps of PTAP and PAP1 strongly suggest these sequences different genomic DNA regions (FIGS. 7 and 10), partial sequencing conducted on the 2.1 kb (EcoRI and HindIII) subclone of PAP1 shows a region of 283 bp that has 99.96% sequence identity to a noncoding region within the 1.4 kb (BamHI and SalI) subclone of the PTAP-2 genomic sequence. The PAP1 genomic clone was designated PTAP-1 based on this alignment although no additional sequence data has been obtained (See FIG. 9A). The other potato genomic clones have been partially sequenced and analyzed. FIGS. 3A–3C shows the complete genomic sequence of PAP3 with indicated exons and poly-A sequences. The nucleotide sequences for potato genomic subclones of PAP7 and PAP11 are given in the Appendices C and D respectively.

Sequence Homology

Figure 6:
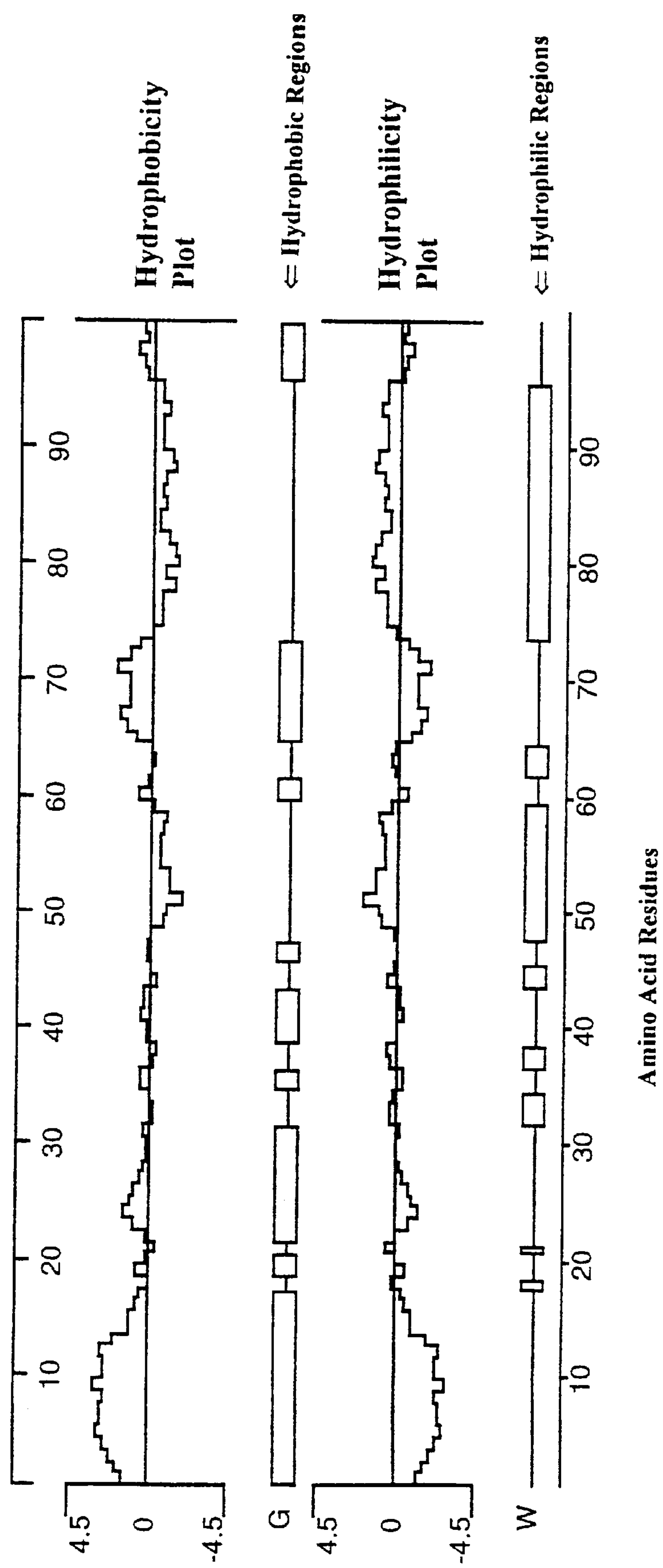
FIGS. 6A-6B are the DNA (SEQ ID NO:11) and deduced amino acid sequence (SEQ ID NO:12) of the PTAP potato tuber cDNA clone. The 1.88 kb insert sequence was subcloned into the Eco RI site of pBluescript. Dideoxy sequencing was performed with purified double-stranded plasmid DNA and analyzed as described in the examples. Nucleotides are numbered on the left. Single letter amino acid designations are given below their respective codons and are numbered on the right. The termination codon is designated with '*'. The $NH_2$-terminal amino acid residue of the mature protein is Thr30 (nucleotide 378) based on protein microsequence data. The initiating Met is predicted to occur at nucleotide 291 based on the upstream, in frame, TGA stop codon at nucleotide 237. The mature polypeptide has a predicted molecular weight of 51.7 kD and an isoelectric point of 6.5.

Protein data base homology searches with the deduced amino acid sequences of PTAP, RAP, PAP3, PAP7 and PAP11 showed some homology to kidney bean iron (III)-zinc(II) purple phosphatase (KBPAP) (SwissProt accession PPAF_PHAVU). FIG. 6 illustrates the alignment of the deduced amino acid sequences of PTAP, RAP, PAP3, PAP7, PAP11 and KBPAP with shaded residues indicating sequence identity to PTAP. Some limited homology was also observed between these plant phosphatases and *Aspergillus ficuum* APHA phosphatase (genpept accession ANU18554_1 and AFU18553_1 and PIR accession 2018153A),

```
Rice         105 VDREKTPWLIVLMHSPMYNS          124
phosphatase
RAP

consensus        VDR+KTPW++V+ H+PMY+S

A. ficuum    344 VDRSKTPWVFVMSHRPMYSS          363
APHA

rice         135 MRAAFEKWFVKYKVDLVFAGHVHAYER   161
phosphatase
RAP

consensus        +R+AFE ++KY VD  F+GH+H YER

A. ficuum    372 VREAFEGLLLKYGVDAYFSGHIHWYER   398
APHA
```

within the COOH-terminus domain of PTAP and related phosphatases. The numbers flanking the sequence indicate amino acid residue number. This region of homology coincides with a relatively conserved domain among plant phosphatases (FIG. 4). In FIG. 4, asterix symbols '*' above the aligned data show the location of the KBPAP residues implicated in binding $Fe^{3+}$ (Asp135, Tyr167 and His325), $Zn^{2+}$ (Asn201, His286 and His323), bridging the active site (Asp164) and the Asn residues with attached oligosaccharide groups (Asn81, Asn109, Asn143, Asn211 and Asn396) (Sträter et al, 1995; Stahl et al, 1994). The metal-binding residues are absolutely conserved in PTAP, RAP, PAP3, PAP7 and PAP11 where sequence data is available.

Phylogeny of Phosphatases

FIG. 5 shows a CLUSTAL phylogenetic relationship (Higgins and Sharp, 1988) constructed from a wide variety of representative phosphatase protein sequences using the MegAlign program. The sequences used are PTAP, PAP3, PAP7, PAP11, RAP, KBPAP, *Aspergillus ficuum* APHA (GenBank accession #U18553), tomato APS1 (M67474), yeast PHOL (M11857), yeast PHO3 (X01080), *Pichia pastoris* phosphatase (U28658), human lysozymal APase (X12548), human prostatic APase (M24902), *Eschericia coli* APPA (M58708), *Yarrowia lipolytica* APase (X65225), *Morganella morganii* APase (X78328) and *Salmonella typhimunum* PHON (x59036). A distinct APase family is observed with PTAP, PAP7, PAP11 and RAP in one group and PAP3 and KBPAP in another group.

Atomic Microprobe Analysis of PTAP Protein

To determine which metal cations are associated with enzymatically active PTAP, a microprobe spectral analysis was performed. The 75 μg (1.3 ηmoles) sample of PTAP contains detectable amounts of Mg, Ca, and Si and no significant amounts of Fe or Zn. Control bovine serum albumin with 0.13, 1.3 and 13 ηmoles of added $Fe^{3+}$ and $Zn^{2+}$ were able to be detected at the 1.3 ηmoles concentration. These results suggest any Fe or Zn associated with active PTAP occurs at less than 1:1 metal ion:PTAP molar ratio.

The expression of PTAP was also characterized since it is the first cloned gene of the family of the most abundant plant phosphatases.

Isolation of a PTAP Unique Probe

A fragment was generated from the PTAP cDNA sequence and used to probe a λZAP library and RNA blots. To eliminate potential heterologous probe binding to other genes in the phosphatase family, the probe needed to be made to a region of the λEMBL3 PTAP gene with low DNA sequence conservation. FIG. 4 shows the alignment of the deduced partial sequence of PTAP with other phosphatases. An area of low sequence conservation amenable to PCR amplification was delineated by nucleotides 1583 to 1810 and fell within the third exon of the p4-3.8 kb subclone. This 227 bp region had 55% overall DNA sequence homology to PAP3 with a largest contiguous sequence identity of 14 bp. Paired PCR oligonucleotide primers were designed to amplify this region from the λEMBL3 PTAP clone. A pair of internal primers were also made to facilitate verification of any PCR product. Thus the 227 bp PCR fragment was successfully isolated with internal primer verification.

Isolation of the PTAP cDNA Clones The cDNA sequence of PTAP was isolated from a λZAP potato tuber cDNA library. Many unsuccessful attempts were made to screen the cDNA expression library with antibodies raised against potato phosphatase. Based on the confirmation of the PTAP genomic clone, $2.5 \times 10^5$ pfu from the same library were screened using the 227 bp PTAP-specific probe described above. Six λZAP clones were enriched to homogeneity and subcloned into pBluescript SK. Similarity among miniprepped plasmids in restriction digest patterns and detection by Southern blotting indicated that all six cDNA clones were the same sequence. Three cDNA clones had molecular weights of 1.9 kb while three were 1.5 kb. One of the 1.9 kb clones was purified and sequenced.

FIGS. 8A-8B show the complete sequence of largest PTAP cDNA clone. The PTAP cDNA clone is 1,878 bp with the coding region extending from nucleotides 291 to 1641. This sequence agrees with that predicted from exons assembled from the genomic PTAP sequence. The deduced amino acid sequence is 451 amino acid residues. Without a transit peptide, PTAP has a deduced molecular mass of 51.7 kD and a predicted isoelectric point of 6.5. The sequence alignment of putative translated exons of PTAP with two amino acid microsequenced fragments, K/R-39 and K/R-46 has been shown. The complete cDNA sequence permitted alignment of other microsequenced fragments of protein with the deduced PTAP amino acid sequences as follows:

```
pPTAP (a.a. 30 to 44)     TQFPSVDIPLENEV
M-1                       TGFP?V?IPLE
M-2                       RQFPIVDIPLEN?V
N-terminus                SQFPSMNI
consensus                 TQFPSVDIPLENEV

pPTAP (a.a. 328 to 347)   MRSAYERWFVKYKVDVIFAG
consensus                 M SAYE WFVKYKVDVIFAG
M-3                       MESAYEVWFVKYKVDVIFAG

pPTAP (a.a. 358 to 376)   ISNIHYNVSGGDAYPVPDK
consensus                 ISNIHY VSGG AYPVP K
K/R-20                    ISNIHY?VSGG?AYPVP?K

pPTAP (a.a. 397 to 408)   FRDPQPEYSAFR
consensus                 FRDPQPEYSAFR
K/R-22                    FRDPQPEYSAFR

pPTAP (a.a. 432 to 449)   NDDGNAITTDSFTLHNQ
consensus                 NDDGN ITTDSFTLHNQ
K/R-28                    NDDGN?ITTDSFTLHNQ
```

Figure 7:
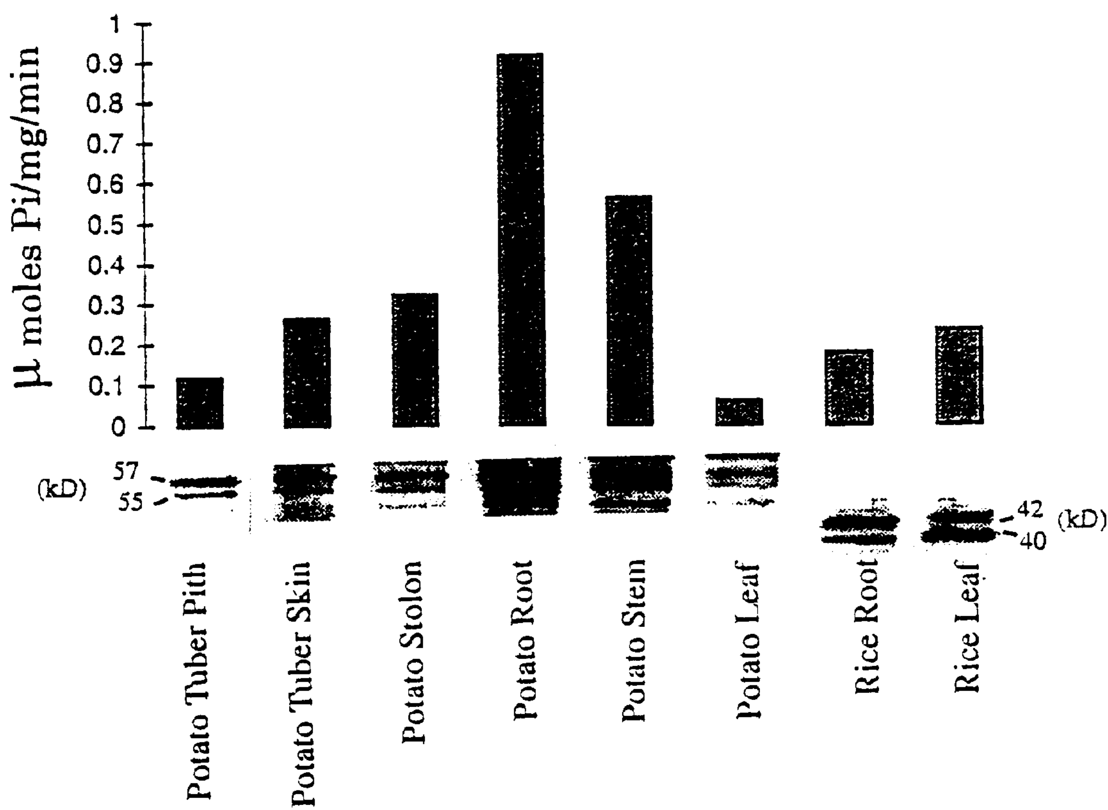
FIG. 7 illustrates the hydropathy of the first 100 amino acid residues of PTAP. The hydrophobicity plot and predicted hydrophobic regions are shown on the upper half of the figure while the lower half shows the hydrophilicity plot and hydrophilic regions. Values were determined using the Protean program (DNAStar, Madison, Wis.). The initial 29 amino acid residues, which constitute the putative targeting peptide (See FIGS. 6A-6B), are within a hydrophobic region.

Three of the microsequenced PTAP fragments, M-1, M-2 and N-term, aligned with PTAP at amino acid 30, indicating that mature PTAP starts at amino acid 30 and that the target peptide is the first 29 amino acid residues. FIG. 7 shows a hydropathy plots of PTAP amino acid residues. The hydrophobicity observed with the first 29 residues is a common feature of transit peptides. The deduced amino acid sequence of PTAP deviates from PTAP fragment consensus alignments by 6%. Most of these mispairings are to unresolved residues during microsequencing which are indicated by '?'. Amino acid conflicts, found with one residue of M-3 and with all three N-terminal fragments, are likely a result of the difficulty resolving certain residues from background contaminating residues. The background contamination is most pronounced during the initial sequencing cycles and is especially problematic with partially blocked N-termini. A Prosite computer analysis revealed no significant sites or signatures within the primary protein sequence of PTAP. Alignment of the complete PTAP sequence with related phosphatases is shown in FIG. 4.

Anti-PTAP Antibodies

An immunoremoval assay demonstrated the capacity of anti-PTAP antiserum to bind phosphatase as an antigen. Protein A Sepharose served to precipitate IgG proteins with whatever antigens they would bind. Western blotting was performed to define the detection limit of various dilutions of affinity purified anti-PTAP antibodies. SDS-PAGE separated purified PTAP samples loaded as follows: 10 ηg, 5 ηg, 2.5 ηg, 1.2 ηg, 60 ρg, 30 ρg and 15 ρg and probed with 0-, 6- and 20-fold dilutions of affinity purified anti-PTAP polyclonal antibodies. Undiluted, 6-fold diluted and 20-fold diluted anti-PTAP antibodies had detection limits of 600 ρg, 1.2 ηg and 2.5 ηg respectively. Subsequent screenings were performed on 6-fold dilutions of the affinity purified antibodies.

Phosphatase Western Blot Detection and Phosphatase Activity

FIG. 8 shows phosphatase activity and anti-PTAP polyclonal antibody detection within protein extracts of potato tuber pith, potato tuber skin, stolon, potato root, potato leaf, rice root and rice leaf. FIG. 8 (base of curve) indicates the PTAP 57 and 55 kD, and the corresponding rice 42 and 40 kD, SDS-PAGE bands detected by western blotting from 10 μg clarified cytosolic protein extracts. Ponceau S staining of the PVDF membrane immediately after transfer indicated that relatively equivalent amounts of protein were present within each lane. Polypeptides immunologically related to PTAP are present in varying amounts in all tissues. In comparison to potato tuber, root and stem (lanes 4 and 5) showed high levels of the PTAP polypeptides, stolon and tuber skin show the next most abundant PTAP polypeptides and the other tissues had relatively small amounts of PTAP-related antigens.

FIG. 8 (bar graph) also shows the phosphatase activity of the plant tissues. The results indicate phosphatases are present in all the tissues, but the highest activity was observed in potato root and then stem tissues while potato leaf tissue had the lowest activity. Rice leaf tissues had approximately double the phosphatase activity of rice root. The rice was in a state of phosphate-starvation when harvested and was likely releasing internal reserves of phosphate. phosphatase activity approximately correlated with amounts of the 57 and 55 kD isoforms detected by anti-PTAP western blotting.

Northern Blotting of Potato Tissues

A more precise measure of PTAP expression involved looking for PTAP transcripts in RNA from various tissues. A northern blot containing 10 μg of sprouting potato tuber, dormant potato tuber, stolon, root and leaf total RNA was probed with the PTAP-specific probe. A single 2.7 kb transcript was detected. PTAP transcripts were observed in dormant tuber RNA and to a lesser extent in the stolon sample. Leaf and root RNA showed trace amounts of PTAP transcript while sprouting tuber had no detectable signal. PTAP or closely related enzymes appear to have roles beyong the tuber-specific ones suggested previously. These results suggest PTAP has a role in developing and dormant tubers.

A PAP3-specific probe was used to screen the potato RNA blot described above but resulted in no detectable signals. In addition, blots of rice root and shoot total RNA were probed with the PTAP-specific probe at a stringency allowing for 85% sequence homology (assuming 1% mismatch for each 1° C. reduction) but produced no signal. Of the potato Apase genomic clones we previously isolated, PAP3 is the most divergent from PTAP. Since PAP3 is most homologous to the kidney bean purple phosphatase protein, it could be localized in seed tissues. It could also be transcribed at a very low level or not at all.

Technological Applications

A fundamental goal of plant breeding, genetics and molecular modification of plants has been the improvement in the yield of crop plants. However, few modification attempts have involved the various macronutrient uptake pathways because the associated genes were unknown and obtaining mutants was difficult. Identification of the genes encoding members of the major family of plant phosphatases has major and important potential agricultural and industrial ramifications. The nucleic acids of the plant phosphatase makes it possible to develop applications which take advantage of the following PTAP features: high non-specific phosphatase activity, which level of tuber-specific expression, and the long-term stability even after exposure to heat and proteolytic conditions. The following examples are not intended to be limiting.

Seed plants such as canola, soybean and corn, store phosphate in the form of phytate (the salt of 1,2,3,4,5,6-cyclohexanehexolphosphoric acid). The presence of phytate is a problem if the seed is made into meal and used as feed for animals. Monogastric animals cannot metabolize phytate and utilize its phosphate. In addition, phytate binds to essential minerals, such as calcium, manganese and zinc, making them relatively unavailable to the animal. Phytate contamination in animal feed necessitates expensive and time-consuming processing to remove this compound. Further, standard processing attempts, including ultrafiltration, washing and acid treatment, only partially remove this molecule from the meal. Enzymatic treatment with phytase is somewhat effective at reducing phytate amounts, but is very expensive.

The development of transgenic crop plants which specifically express phosphatase in the seed during phytate accumulation would alleviate phytate contamination in animal feed and therefore eliminate post-harvest processing steps. Phosphatase hydrolysis phytate into harmless compounds; therefore, such phosphatase transgenic plants would have reduced phytate levels.

For example, a method of decreasing levels of phytate in seeds can consist of preparing an expression construct comprising a promoter operably linked to a DNA sequence encoding an phosphatase which can degrade phytate. The construct is then incorporated into a plant or plant part. The plant part is regenerated to produce a new plant, or the transformed plant is grown under conditions so that the phosphatase is expressed in developing seeds thereby reducing levels of phytate in seeds.

Commercial compounds may exhibit different biochemical properties when in a phosphorylated state. Where phosphorylation is undesirable, large-scale dephosphorylation is required to make a compound chemically uniform. This requires the purchase of enzymes purified from native sources. The plant phosphatase genes of this invention code for enzymes with a number of desirable features including a very high activity, permissive substrate range, and enzymatic stability in the presence of protease and temperature extremes. Genetically-engineered PTAP enzymes could be used and packaged more cost effectively than other enzymes, especially for addition to animal feed, since PTAP is the most active phosphatase characterized and it is very stable. Another marketable feature of PTAP is that it is a plant product, thus its addition to animal feed may be seen as more wholesome than enzymes derived from bacterial, fungal or chemical processes.

In vitro production of phosphatase would make large quantities of the enzyme available for treatment of phytate-contaminated animal feed and for processing of economically valuable phosphorylated compounds. Pure phosphatase, produced efficiently and inexpensively through fermentation of transgenic bacteria or yeast host cells, is useful for a number of industrial applications requiring a stable and highly active source of phosphatase activity. A specific example is the dephosphorylation of phosphonate in the dairy industry which could provide improved dairy products with low production costs and greater enzymatic efficiency than presently-used processes. Other examples include soy processing, steeping of corn or sorghum kernels, and in the starch industry.

One example of a method to produce phosphatase could consist of preparing an expression construct comprising a promoter operably linked to a DNA sequence encoding an phosphatase selected from SEQ ID NO:1, SEQ ID NO:2, SEQ ID NO:3, SEQ ID NO:4 or SEQ ID NO:5. The construct is then incorporated into a host cell which is grown and maintained under conditions wherein the phosphatase is expressed. The phosphatase can be harvested through extraction from the cells, or by inducing cellular secretion and purifying the enzyme from the growth medium.

Transgenic expression of proteins is often impeded by the intracellular instability of the foreign protein. In prokaryotes, unstable transgenic proteins are produced as fusion proteins. Inactive pieces of a known stable protein are synthesized onto the ends of the transgenic product imparting stability to the whole fusion protein. Although fusion proteins are part of most procaryotic expression systems, they are not a common feature of eukaryotic expression vectors.

Phosphatases have proved extremely resistant to degradation from protease activity and changing buffer conditions. Most enzymes and proteins would be degraded under equivalent conditions. The PTAP stability against physical and proteolytic degradation can be exploited in the design of eukaryotic expression vectors. Insertional disruption of a gene sequence within a PTAP-expressing vector could produce in a stable fusion protein. To produce a PTAP expression vector, an inducible expression system for PTAP can be developed and a polylinker introduced by silent site-directed mutagenesis within a domain that disrupts phosphatase activity upon an insertional event without affecting its stability. Candidate segments of DNA for the polylinker are the non-conserved regions delineated by amino acids 86–97, 242–246 and 393–399 of PTAP. The excellent stability of phosphatase thus can be used to construct vectors which express stable fusion proteins. The stabilization would result from adding PTAP 5' and/or 3' sequences to the coding region of the other protein.

The compositions described herein can be used to enhance the uptake of phosphate in plants. Phosphate is the most limiting soil nutrient during the growth of plants. This limitation is overcome by the addition of phosphaterich fertilizer, which is expensive, detrimental to the environment, and does not specifically target crops. Induction of a transgene root phosphatase prior to fertilizer application would permit rapid and efficient uptake of P, providing advantage to the crop plant over weeds and reducing dispersion into the environment.

A further embodiment provides transgenic crop plants which have constitutively high levels of phosphatase in their roots. Overexpression of PTAP activity in roots can assist the plant to utilize relatively inaccessible phosphate sources such as rock phosphate and other unexploited phosphate sources faster and more efficiently than non-transformed and competitor plants. Even a modest increase in the efficiency of plants to utilize phosphorus can make a significant contribution to the reduction of the ever-increasing fertilizer costs in agriculture.

EXEMPLIFICATION

Example 1

Chemicals and Plant Material

Biochemicals, coupling enzymes, anti-rabbit IgG (whole molecule) alkaline phosphatase conjugate, polyethylene glycol, Tween 20, bisacrylamide, and non-prestained SDS-PAGE molecular-mass standards were purchased from Sigma. Prestained "rainbow" molecular-mass standards were purchased from Amersham (Oakville, ON). Protein assay reagent was obtained from BioRad (Mississauga, ON). CNBr was obtained from Kodak (Toronto, ON). Phosphocellulose P-11 was purchased from Whatman (Hillsboro, Oreg.). Polyvinylidene difluoride (PVDF) membranes (Immobilon transfer; 0.45 mm pore size) were supplied by Millipore (Mississauga, ON). S-Sepharose, Phenyl Superose HR 5/5 column and a FPLC system were obtained from Pharmacia (Baie D'Urfe, PQ). Monospecific affinity-purified rabbit anti-(P-Tyr) IgG (Dr. Peter Greer, Department of Biochemistry, Queen's University). All buffers were degassed and adjusted to their respective pH values at 25° C. Mature tubers of potato (*Solanum tuberosum* L. cv. Chiefton) were purchased at a local market and used the same day.

Example 2

Enzyme Assays

Phosphatase Assay A

For routine measurements of phosphatase activity, the hydrolysis of PEP to pyruvate was coupled with the lactate dehydrogenase reaction and assayed at 25° C. using a Varian DMS 200 spectrophotometer. Standard assay conditions were 50 mM Na-acetate buffer (pH 5.8) containing 5 mM PEP, 4 mM $MgCl_2$, 0.2 mM NADH, and 3 units of dialysed rabbit muscle lactate dehydrogenase in a final volume of 1 mL. Assays were initiated by the addition of enzyme preparation. One unit of phosphatase activity is defined as the quantity of enzyme that would catalyze the hydrolysis of 1 mmol of substrate/min at 25° C.

Phosphatase Assay B

For substrates other than PEP, the method of Eibl and Lands (1969) was used to detect the Pi released by the phosphatase reaction. Phosphatase (0.05 units) was incubated in 1.5 mL cuvettes with 0.9 mL of 50 mM MES-NaOH (pH 5.8) containing 4 mM $MgCl_2$ and an alternative substrate (5 mM unless otherwise indicated) for 6 min at 25° C. Reactions were terminated by the sequential addition of 0.1 mL reagent A (3 M $H_2SO_4$ containing 20 mM ammonium molybdate) and 10 ml of 1% (v/v) Triton X-100. Samples were incubated at 25° C. for 20 min and the $A_{660}$ was determined. To calculate activities, a standard curve over the range of 0.01 to 1.0 mmol Pi was constructed for each set of assays. Assays were performed in triplicate and controls were run for background amounts of Pi present at each substrate concentration by adding reagent A before the enzyme. Hydrolysis was proportional to enzyme concentrations between 0.005 to 0.1 units/mL and remained linear with time for at least 15 min.

Example 3

Kinetic Studies

Apparent $K_m$ values were determined from the Michaelis-Menten equation fitted to a non-linear least-squares regression computer kinetics program (Brooks, 1992). All kinetic parameters are the means of duplicate determinations performed on two separate preparations of the purified enzyme, and are reproducible to within ±10% SE.

Example 4

Enzyme Purification

Potato tuber phosphatase was purified by the method of Gellatly et al. (1994).

Example 5

Stability of phosphatase in Potato Tuber Extracts

Clarified extracts were prepared by homogenizing peeled and diced mature potato tuber tissue (0.5 g) with a Polytron in 1 volume of (a) buffer A lacking PMSF; (b) buffer A supplemented with the following protease inhibitors: 1 mM N-tosyl-L-lysine chloromethyl ketone, 1 mM N-tosyl-L-phenylalanine chloromethyl ketone, 1 mM diphenylcarbamylchloride, 2 mM p-hydroxymecuribenzoate, 3 mM 1,2-epoxy-3-(p-nitrophenoxy)-propane, 10 mM bipyridyl, 5 mM 1,10-phenanthroline, 0.1 mg/mL soybean trypsin inhibitor, 0.1 mg/mL pepstatin, 0.1 mg/mL antipain, and 0.1 mg/mL aprotonin; or (c) hot (90° C.) SDS-PAGE sample buffer. The homogenates were centrifuged for 10 min at 16,000 g in an Eppendorf microcentrifuge. A 0.5-mL aliquot of the crude supernatant fluid prepared in buffer A lacking protease inhibitors (a) was incubated for 16 h at 25° C. An aliquot of each crude supernatant fraction was mixed with an equal volume of SDS-PAGE sample buffer, and boiled for 3 min for immunoblot analysis using anti-(*Brassica nigra* [black mustard] PEP-specific phosphatase) IgG as described below.

Example 6

Electrophoresis and Determination of Native and Subunit Molecular Masses

Nondenaturing PAGE was performed with a BioRad (La Jolla, Calif.) mini-gel apparatus using the discontinuous system of Davis (1964). The final acrylamide monomer concentration in the 0.75-mm thick slab gels was 8% (w/v) for the separating gel and 2.5% (w/v) for the stacking gel. Prior to pouring the stacking-gel solution, the separating gel was pre-electrophoresed for 2 h at 150 V constant voltage, with 250 mM Tris-HCl (pH 8.8) as the electrode buffer. The stacking gel was polymerized with fluorescent light for 3 to 4 h. Gels were precooled to 4° C. and were maintained at this temperature during electrophoresis. Samples containing 50% (v/v) glycerol were run at a constant voltage of 120 V, applied for 2 h. Tris (25 mM)/glycine (190 mM) containing 1 mM thioglycolate was used as the electrode buffer. Gels were either stained for protein using Coomassie Blue R-250 or phosphatase activity was located in the gel. To detect phosphatase activity, the gel was equilibrated for 15 min at 24° C. in 100 mM Na acetate (pH 5.8) containing 20 mM $CaCl_2$, followed by incubation for 15 min at room temperature in 100 mM Na acetate (pH 5.8) containing 20 mM $CaCl_2$, 0.02% (w/v) Fast Garnet GBC salt, and 0.02% (w/v) $Na_2$-naphthyl phosphate. For second dimension electrophoresis, the single protein-staining band was excised from the nondenaturing gel and incubated in 62 mM Tris-HCl (pH 6.8) containing 10% (v/v) glycerol, and 2% (w/v) SDS for 40 min at 50° C. After equilibration in SDS, the gel slice was subjected to SDS-PAGE as described below.

Denaturing SDS-PAGE was performed using a BioRad mini-gel apparatus and the discontinuous system of Doucet and Trifaró (1988) or Laemmli (1970). Final acrylamide monomer concentrations in the 0.75-mm thick slab gels was 14, 12 or 10% (w/v) for the separating gel and 4% (w/v) for the stacking gel. All samples were preincubated in the presence of SDS sample buffer (70 mM Tris-HCl, pH 6.7, containing 8 M urea, 3% [w/v] SDS, 100 mM DTT and 0.005% [w/v] bromophenol blue) for 3 min at 100° C. prior to being loaded on the gels. Gels were run at a constant voltage of 155 V, applied for 1 h. For the determination subunit molecular masses by SDS-PAGE, a plot of relative mobility versus log (molecular mass) was constructed with the following standard proteins: β-galactosidase (116 kD), phosphorylase b (97.4 kD), BSA (66 kD), ovalbumin (45 kD), and carbonic anhydrase (29 kD). Glycoprotein staining of SDS gels was conducted using a periodic acid-Schiff silver-staining protocol (Dubray and Bezard, 1982).

Non-dissociating SDS-PAGE was utilized for native molecular mass determinations (Goldstein et al, 1988). SDS-PAGE was carried out as described above except that the purified phosphatase was mixed with 1% (w/v) SDS and 0.005% (w/v) Bromophenol Blue without boiling. For the determination of native molecular mass by SDS-PAGE, a plot of relative mobility versus log (molecular mass) was constructed with the following pre-stained "rainbow" standard proteins: myosin (200 kD), phosphorylase b (97.4 kD), BSA (69 kD), ovalbumin (46 kD), carbonic anhydrase (30 kD), and soybean trypsin inhibitor (21.5 kD).

Example 7

Peptide Mapping by Cyanogen Bromide Cleavage

Polypeptides were excised individually from an SDS mini-gel and cleaved in situ with cyanogen bromide, and the degradation products were analyzed on a 1-mm thick 14% (w/v) SDS mini-gel according to the method of Plaxton and Moorhead (1989).

Example 8

Immunoblotting

Electroblotting was performed by the method of Moorhead and Plaxton (1990), with the addition of 100 mM o-vanadate to the transfer buffer when maintenance of phosphotyrosyl residues was desired. All immunoblots to be probed with the anti-(black mustard PEP-specific phosphatase) IgG (Duff et al, 1991a) were first pre-treated with sodium m-periodate according to Laine (1988) so as to oxidize antigenic oligosaccharide chains of endogenous tuber glycoproteins. Immunological detection of phosphotyrosylated tuber proteins using anti-(P-Tyr) IgG (Kamps and Sefton, 1988) was performed as referenced above except that the blocking buffer contained 5% (w/v) bovine serum albumin (fraction V) and 1% (w/v) ovalbumin instead of 3% (w/v) defatted milk powder.

Antigenic polypeptides were visualized using an alkaline-phosphatase-tagged secondary antibody (Moorhead and Plaxton, 1990). Immunological specificities were confirmed by performing immunoblots in which rabbit preimmune serum was substituted for the affinity-purified IgGs. An LKB Ultroscan XL Enhanced Laser Densitometer was used to scan indicated immunoblots. Densitometric data were analysed using the LKB Gelscan XL software (version 2.1). Immunoreactive polypeptides were quantified in terms of their relative absorbance at 633 nm wavelength ($A_{633}$).

Example 9

Dephosphorylation of Potato Tuber Phosphotyrosyl Proteins by Potato phosphatase

Peeled and diced potato tuber tissue (5 g) was homogenized with a Polytron in 1 volume of 100 mM MES-NaOH (pH 5.8) containing 2 mM PMSF, 2 mM DTT, and 1 mM EDTA. The homogenate was centrifuged for 10 min at 13,000 g in an Eppendorf microfuge, and a 3-mL aliquot of the supernatant fluid was passed at 4° C. through a BioRad Econo-Pac 10DG desalting column that had been pre-equilibrated in homogenization buffer lacking PMSF. Aliquots (0.1 mL) of the desalted crude extract were incubated at 25° C. with and without 3 units of the purified potato phosphatase. Samples were removed at 0, 2 and 19 h and analyzed by immunoblotting using the anti-(P-Tyr) IgG as described supra. Laser densitometric scanning and immunoquantification of the blots was performed as described supra.

Example 10

Protein Determination

Protein concentration was determined by the method of Bradford (1976) using the BioRad prepared reagent and bovine γ-globulin as standard.

Example 11

Potato Phosphatase

Phosphatase from potato (*Solanum tuberosum* L. cv. Chiefton) tubers was purified according to the method described by Gellatly et al, 1994.

Example 12

Microsequencing of Cyanogen Bromide and Trypsin Digested Fragments

Based on the method of Plaxton and Moorhead (1989), 60 μg purified potato phosphatase was digested with cyanogen bromide. Denaturing SDS-PAGE was performed using a BioRad (Mississauga) gel apparatus and the discontinuous system of Laemmli (1970). Final acrylamide monomer concentrations in the 1.5-mm thick slab gels was 14% (w/v) for the separating gel and 4% (w/v) for the stacking gel. Both gel phases were allowed to polymerize for 40 h at room temperature prior to use. Potato phosphatase cyanogen bromide fragments were preincubated in the presence of SDS sample buffer (62.5 mM Tris, pH 6.9, containing 1 M sucrose, 3% [w/v] SDS, 2 mM EDTA, 1% [v/v] β-mercaptoethanol and 0.0005% [w/v] bromophenol blue) for 15 min at 37° C. prior to being loaded on the gels. Gels were run at a constant voltage of 200 V, applied for 4 h with 0.1 mM thioglycolate in the upper running buffer. For the determination of fragment molecular masses by SDS-PAGE, a plot of relative mobility versus log (molecular mass) was constructed with the following BioRad prestained standard proteins: phosphorylase b (106 kD), BSA (80 kD), ovalbumin (49.5 kD), and carbonic anhydrase (32.5 kD), soybean trypsin inhibitor (27.5 kD), and lysozyme (18.5 kD). The gel was blotted to BioRad Protein Sequencing Membrane using 12.5 mM Tris, 96 mM glycine and 10% [v/v] methanol. The membrane was stained for 10 minutes at room temperature with 0.025% Coomassie Blue R-250 dissolved in 40% methanol and destained in 50% methanol until bands were visible. Isolated bands were excised, rinsed in distilled water and kept moist in microfuge tubes wrapped with parafilm. Microsequencing was performed as a service by Queens University Core facility (Kingston, ON). Trypsin-digested fragment microsequencing was performed as a service by Harvard Microchem (Cambridge, Mass.). 60 μg pure PTAP was applied to polyvinylidene difluoride membrane (PVDF; BioRad, Mississauga, ON). Isolated bands were excised, rinsed in distilled water and kept moist in microfuge tubes wrapped with parafilm. Samples were sent to Harvard Microchem where they were subjected to tryspin digestion and HPLC separation. The HPLC data was analyzed and polypeptide peaks were selected for microsequencing.

Example 13

λEMBL3 Genomic Library Screening with a Fluorescein-labelled Oligonucleotide

A fluorescein-labelled degenerate oligonucleotide probe, designated 39f, was constructed with inosine residues at all wobble codon sites where 3 or more nucleotides could produce a required amino acid and with fluorescein nucleotides (BioCan, Mississauga, ON) covalently attached to the 5' end. The oligonucleotide was synthesized by Paul Young, Biology Dept, Queen's University. An λEMBL3 (SP6/T7) potato genomic library, obtained from Clontech (Palo Alto, Calif.; cat# FL1003j), was screened in the following manner. NM538 *Eschericia coli* host cells were prepared by inoculating 100 mL of LB medium supplemented with 10 mM $MgSO_4$ and 0.2% maltose with a single colony and incubated at 30° C. with vigorous shaking overnight. NM538 cells were centrifuged at 4000 g for 15 min and resuspended in ½ volume of 10 mM $MgSO_4$. Four 230 $mm^2$1.5% LB agar plates were equilibrated at 37° C. For each plate, a 1.7 mL aliquot of NM538 host cells were infected with $1.25\times10^5$ pfu and incubated with shaking at 37° C. for 15 min. Infected cells were mixed with 20 mL of 48° C. 0.7% agarose supplemented with 10 mM $MgSO_4$ and rapidly spread onto pre-warmed LB agar plates. The plates were incubated at 37° C. until the plaques were almost touching (8–16 h) and then placed at 4° C. for at least 15 min. Numbered Nytranplus membranes (Mandel, Guelph, ON) were applied to the surface of each similarly numbered plate for 5 min and marked by puncturing both membrane and agar with a needle. Membranes were successively placed inverted, for 5 min each, onto 3 layers of filter paper saturated with 0.5 M NaOH, then 0.5 M Tris-HCl, pH 8.0 for 5 min and finally 2× SSC. Treated membranes were air dried and then baked at 80° C. for 1 h. The blot was sealed in a small Tekstar (BioCan) glass hybridization bottle with 5 mL 58° C. preheated prehybridization buffer consisting of 3M filtered TMAC, 0.1 M $NaPO_4$ (pH 6.8), 1 mM EDTA (pH 8.0), 5× Denhardt's solution, 0.6% SDS and 100 μg/mL denatured sonicated herring sperm DNA and placed in a rotary hybridization oven at 65° C. for 3 hr. 10 ρmol/mL fluorescein-labelled 39f oligonucleotide was added to 5 mL fresh preheated prehybridization buffer, exchanged with the prehybridization buffer and allowed to hybridize with the blot for 2 days at 65° C. The blot was rinsed with 10 mL wash solution consisting of 3 M TMAC, 50 mM Tris-HCl (pH 8.0), and 0.2% SDS briefly at room temperature followed by a 15 min wash with 200 mL fresh wash solution at 65° C. with gentle orbital shaking. The blot was rinsed at room temperature 3 times for 5–10 min each in 200 mL 2× SSC and 0.1% SDS. Detection of the probe involved a modification of the Renaissance fluorescein kit (cat#NEL-203) procedure of Dupont NEN (Mississauga, ON). After the final hybridization wash, the blot was rinsed in buffer 1 containing 0.1 M Tris-HCl (pH 7.5) and 0.15 M NaCl and incubated in block solution consisting of 0.5% (w/v) Renaissance blocking reagent in buffer 1 for 1 h at room temperature. The blot was exposed to an appropriate dilution of anti-fluorescein-horseradish peroxidase conjugate in block solution for 1 h at room temperature. Following four 5 min washes in buffer 1, the blot was incubated with shaking to a 1:1 mixture of Enhanced Luminol Reagent and Oxidizing Reagent for 1 minute. The blot was briefly patted on filter paper to remove excess liquid and autoradiographed for 5 min to 1 h, depending on fluorescence.

Positive clones were aligned with the master plate. Cores from the plate were placed into 500 μL SM buffer comprised of 100 mM NaCl, 20 mM Tris-HCl (pH 7.5), 10 mM $MgSO_4$, and 0.01% gelatin with 25 μL added ultrapure chloroform, vortexed and stored overnight at 4° C. Dilutions of the eluted phage particles were made the following day for each core and plates containing 500–1000 pfu were absorbed to Nytran as described above for a secondary screen. The screening procedure was repeated until all plaques from a given core yielded positive signals.

Example 14

Purification of λEMBL3 Genomic Clones

λEMBL3 recombinant phage were amplified and purified according to the procedure described in Sambrook, et al. (Sambrook et al, 1989).

Example 15

Restriction Mapping and Subcloning of Genomic Clones

Purified λEMBL3 clones were digested with various restriction enzymes using 10× reaction buffers and enzymes supplied by Pharmacia (Baie D'Urfe, PQ), Promega (Fisher, Nepean, ON) or BRL (Burlington, ON). DNA fragments were separated by 0.6–2% agarose electrophoresis according to desired resolution. Gels were stained with 0.5 μg/mL ethidium bromide and photographed. For each gel, a plot of mobility through agarose gel versus log (molecular weight) was constructed from EcoRI- and HindIII-digested λ molecular weight standards with the following fragment sizes (kb): 21.2, 5.15, 4.97, 4.27, 3.53, 2.03, 1.90, 1.58, 1.38, 0.947, 0.831, and 0.564. To calculate the molecular weight of small fragments, a 100 bp molecular weight ladder (BRL) was used as a molecular weight standard. Restriction maps of the clones were determined based on single and double digests of various restriction enzymes.

Example 16

Southern blotting

Southern blotting (Sambrook, 1989) was used to determine which DNA restriction fragments contained sequences that hybridized with the probe. The blot was probed with 39f as described in the library screening procedure supra.

Example 17

Subcloning Restriction Fragments

Restriction fragments that hybridized with the 39f probe were subcloned into pBluescript SK (Stratagene, La Jolla, Calif.). 10× T4 DNA ligase buffer containing 300 mM Tris-HCl (pH 7.8), 100 mM $MgCl_2$, 100 mM DTT and 10 mM ATP and T4 DNA ligase at 10,000 units/mL were supplied by Promega. Restriction digests were performed with sufficient starting λEMBL3 DNA to yield at least 0.1 μg of the fragment to be subcloned. Following agarose gel electrophoresis and ethidium bromide staining, the band of interest and digested pbluescript SK were excised from the gel, purified by Geneclean (BioCan) and eluted in 10 μL of sterile water. A mixture with a vector:restriction fragment molar ratio of 1:1 for heterologous ends or 1:10 for homologous ends was made in 17 μL total volume. Two μL 10× T4 DNA ligase buffer and 1 μL T4 DNA ligase were added and the reaction mix was incubated at 16° C. overnight. The ligation mix was transformed in *Eschericia coli* DH5α competent cells supplied by BRL. 50 μL DH5α competent cells were thawed on ice and 10 μL ligation mix was gently mixed in by pipetting with swirling followed by gentle tapping. The cells were kept on ice for 30 min, heat shocked for 30 seconds at 37° C. and placed back on ice for 5 min. One mL SOC media was added to the transformed cells and they were incubated at 37° C. with shaking for 1 h. The cells were briefly centrifuged and 900 μL supernatant was discarded. The pellet was resuspended in the remaining 100 μL supernatant. 10 μL and 90 μL aliquots were plated onto 1.5%

LB agar plates containing 100 μg/mL ampicillin. For cloning into plasmids with homologous sticky ends, X-gal was added to 1 μg/mL into the LB agar prior to pouring the plates. The plates were incubated overnight at 37° C. Colonies were selected and plasmids were miniprepped as described below.

Example 18

Miniprep and Maxiprep plasmid DNA Purification

Routine plasmid minipreps were based on the lithium miniprep procedure of Ausubel et al (Ausubel et al, 1992, pp. 1.6). The miniprep pellet was resuspended in 30 μL TE buffer. Restriction digests with this miniprepped DNA required the addition of DNase-free RNase A to a final concentration of 100 μg/mL. Cultures used for minipreps were stored at 4° C. for up to 1 week until maxiprepped or discarded Plasmid maxipreps used the DNA-binding properties of celite. 500 mL of LB supplemented with a selective antibiotic in a 2 L flask was inoculated with 100 μL of an appropriate miniprep culture or a single colony derived from a frozen culture streaked on LB agar containing an appropriate antibiotic and incubated overnight at 37° C. with 250 rpm orbital shaking. Saturated cultures were transferred to 500 mL centrifuge bottles and centrifuged at 4,600 g for 10 min at 4° C. The drained pellet was resuspended in 40 mL buffer 1 containing 50 mM glucose, 25 mM Tris-HCl (pH 8.0) and 10 mM EDTA. Eighty mL of freshly made buffer 2 containing 0.2 N NaOH and 1% SDS was added, mixed by swirling and placed on ice for exactly 5 min. 40 mL buffer 3, made in 500 mL batches using 61.25 g potassium acetate, 35.7 mL glacial acetic acid and water, was added, mixed by shaking and kept on ice for 30 min. The mixture was centrifuged at 11,000 g for 10 min at 4° C. and the supernatant was filtered into flasks through 2 layers of kimwipe tissue. The volume of the filtrate was measured and transferred to a clean centrifuge bottle. 75 mL (0.5 volumes) of isopropanol was mixed with the filtrate and the bottle was centrifuged at 11,000 g for 20 min at 4° C. The drained pellet was marked on the outside of the tube, rinsed with 50 mL 70% ethanol and allowed to dry for 15 min. All residual droplets of ethanol were removed by aspiration. Buffer 4 is made by dissolving 7 M guanidine hydrochloride in 166.7 mL buffer 3 with gentle heating in a very clean beaker (some of the guanidine hydrochloride may not dissolve), adjusting the pH to 5.5, adjusting the volume to 500 mL with water, and filtering the solution through 1 layer of Whatmann No. 1 filter paper. Buffer 5 is 100 mL buffer 4 added to a bottle containing 15 g Fluka (Caledon Laboratories, Georgetown, ON) insoluble celite powder. The pellet was resuspended in 4 mL TE buffer and added to a 50 mL screw cap tube containing 40 mL of buffer 4 and 10 mL of buffer 5. The DNA solution and binding buffer slurry was gently mixed by inversion for 20 min. Resuspended slurry was poured into a BioRad Econo-Pac column and a resin bed was allowed to form under constant suction from a Promega vacuum manifold connected to an aspirator. When the column was dry, it was washed by adding 20 mL buffer 6 containing 200 mM NaCl, 20 mM Tris-HCl (pH 7.5), 5 mM EDTA (pH 8.0), and 50% [v/v] ethanol with continued application of vacuum. When the resin bed appeared dry the vacuum was continued for 1 min. The column was transferred to a 50 mL centrifuge tube and centrifuged for 5 min at 1,500 g at room temperature. Vacuum was reapplied for 5 additional min and then removed from the manifold. 5 mL of 80° C. TE was applied to the column and it was centrifuged at 1,500 g for 5 min at room temperature in a fresh 50 mL centrifuge tube. The eluate was transferred to a labelled 15 mL centrifuge tube and the column was recentrifuged as above. 0.1 volumes of 3 M sodium acetate (pH 5.0) and 1 volume of isopropanol were mixed with the pooled eluate and it was stored overnight at −20° C. Pellets were recovered after centrifugation at 5000 g for 20 min at 4° C. and rinsed with 10 mL 70% ethanol. Dried pellets were resuspended in 500 μL TE and transferred to a 1.5 mL microfuge tube. 20 μg/mL DNase-free RNase A was added to the solution and incubated at 37° C. for 30 min. The DNA solution was vortexed with an equal volume of a 1:1 (v/v) mixture of equilibrated phenol and chloroform. The aqueous phase was recovered and extracted with an equal volume of chloroform as above. To the final aqueous phase was added 0.1 volumes of 3 M sodium acetate (pH 5.0) and 1 volume of isopropanol. After mixing, the DNA was pelleted by centrifugation at 13,000 g for 20 min at 4° C., rinsed in 70% ethanol, dried and resuspended in 500 μL TE.

Example 19

Culturing Rice and Potato Plants

Rice seeds (*Orysa sativa* cv. Japonica) were germinated on sterile 0.5× MS medium containing 3% sucrose and 1% agar in 90 mm petri plates. For genomic DNA isolation, seedlings were transferred to soil and harvested in 14 days. Locally purchased potato tubers were segmented and planted in soil after pretreatment for 2 weeks at 4° C. After 30 days potato leaf, stolon and root tissues were harvested. Hard potato tubers and soft, sprouting potato tubers were harvested as available.

Example 20

Isolation of Genomic DNA

Plant genomic DNA was isolated according to the CTAB-based protocol of Doyle and Doyle (1990).

Example 21

PCR Amplification

Taq Plus DNA polymerase and 10× buffer were supplied by Sangon (Scarborough, ON, cat#D090). Fifty μL PCR reactions were routinely performed in 0.5 mL microfuge tubes with sequential additions of 30.75 μL distilled water, 5 μL 10× Taq polymerase buffer consisting of 200 mM Tris-HCl (pH 8.8), 100 mM KCl, 100 mM $(NH_4)_2SO_4$, 1% Triton X-100, and 1 mg/mL nuclease-free bovine serum albumin, 8 μL dNTP mix (dGTP, dTTP, dCTP, DATP each at 1.25 mM), 2.5 μL of each oligonucleotide PCR primer (20 μM; see FIG. 19), 1 μL of either 50 ηg/μL genomic DNA or 1 ηg/μL plasmid DNA as template and 0.25 μL Taq Plus DNA polymerase. After mixing and brief centrifugation, one drop of light mineral oil (Sigma, St. Louis, Mo.) was applied over the reaction mixture. The tubes were placed into a thermocycler (Fisher, cat#PTC-150) with 25 cycles of 1 min at 94° C., 2 min at a variable primer annealing temperature ranging from 48 to 60° C. and 3 min at 72° C. After 25 cycles, there was a final 10 min at 72° C. followed by maintenance at 4° C.

Example 22

Random Primer Labeling

Routine double stranded DNA probe labeling with [α-$^{32}$P]-DATP was based on the method described by Sambrook et al (1989).

Example 23

Screening Rice cDNA and Potato Genomic Libraries

A λZAP-II rice callous suspension culture cDNA library (Hirofumi Uchimiya, Institute of Molecular and Cellular Biosciences, Tokyo) and an λEMBL3 potato genomic library (Clontech) were screened according to the S&S protocol for screening libraries with DNA probes.

Example 24

Subcloning of λEMBL3 Genomic Clones

λZAP-II clones were subcloned into pBluescript SK utilizing the ExAssist automatic excision system from Stratagene.

Example 25

Sequencing Primer Construction and Synthesis

Oligonucleotide primers and probes were designed to have high melting temperature (minimum for sequencing 48° C.), anneal with a unique sequence and to not autodimerize. Paired PCR oligonucleotide primers were designed to possess compatible thermodynamic properties (including avoidance of primer dimerization and hairpin formation) and to amplify either a specific DNA segment or to yield a product ranging from 200–2,000 bp. Unless stated otherwise, PCR primers were designed with either BamHI or EcoRI restriction sites (including 3 additional 5' nucleotides that will, if possible, anneal with the template 9 to 6 bp upstream from the sequence to be amplified) for digestion and ligation into cloning vectors.

Example 26

Sequencing of Phosphatase Clones

Double stranded dideoxy sequencing was performed following the protocol and using components of the Sequenase Version 2.0 DNA sequencing kit (United States Biochemical, Cleveland, Ohio.).

Example 27

Sequence Analysis and Retrieval

Sequence data input, analysis and alignments were performed using the Lasergene software produced by DNAStar (Madison, Wis.). Microsequenced phosphatase data was aligned with sequences within the PDB, GBupdate, GenBank, EMBLupdate and EMBL databases using the TBLASTX search protocol developed by Altschul et al (1990) using world wide web internet access to servers at National Institute of Health and mirror sites. Nucleotide sequence data was either compared to nucleotide data in the PDB, GBupdate, GenBank, EMBLupdate and EMBL databases using the BLASTN search tool or was translated in all six reading frames and compared to protein sequence data in the PDB, SwissProt, SPupdate, PIR GenPept and GPupdate databases using BLASTX (Gish and States, 1993; Altschul et al,1990).

Example 28

Determination of Fe and Zn by Microprobe Analysis

Electron microprobe analysis using a 15 kEV electron beam ARL Scanning Electron Microscope Quantometer (ARLSEMQ) was performed by Dave Kempson, Geological Science, Queen's University to indicate the atomic composition of PTAP. Samples were prepared as follows. 75 μg (1.3 ηmoles) of purified PTAP, with a p-nitrophenyl phosphate-hydrolyzing specific activity of 618 units/mg, was dialyzed 3,000-fold against sterile $dH_2O$, speed vac dehydrated to 15 μL and dotted and dried onto a carbon sample mount. Four 15 μL control samples consisting of 75 μg BSA with either 0, 0.13, 1.3, or 13 ηmoles added $FeCl_3$ and $ZnCl_2$ were similarly mounted. Both samples were loaded into the ARLSEMQ and subjected to a 0–10 kEV energy spectrum analysis (100 μA emission current and 30–35 ηA sample current) using 200 s point and raster scans and a 30,000 s raster scan. The presence of elements within each sample was determined by specific absorbance spectral peaks.

Example 29

Oligo Construction and Synthesis

Oligonucleotide probes and primers were designed using the PrimerSelect program produced by DNAStar (Madison, Wis.) to have a melting temperature over 48° C., anneal with a unique sequence and to not autodimerize.

Example 30

PCR Amplification

PCR reactions were performed using paired primers derived from the PTAP sequence and the PTAP λEMBL3 genomic clone as template at 55° C. annealing temperature.

Example 31

Screening of a Potato Tuber cDNA Library

A λZAP potato tuber cDNA library was a generous gift of Norman Brisson. $3\times10^5$ pfu of the library was screened using Y1090 *Eschericia coli* host cells and positive clones were subcloned using ExAssist system produced by Stratagene (PDI Bioscience, Aurora, ON). The PTAP-specific probe was labelled according to the random primer procedure.

Example 32

Miniprep and Maxiprep plasmid DNA Purification

The lithium miniprep and celite maxiprep procedures were performed as described previously.

Example 33

Sequencing of Potato Tuber Phosphatase cDNA Clones

Double stranded dideoxy sequencing was based on the Sequenase Version 2.0 procedure as previously described. Sequence data input, analysis, alignments and protein analysis were performed using the Lasergene software produced by DNAStar (Madison, Wis.).

Example 34

Potato Phosphatase

PTAP from potato (*Solanum tuberosum* L. cv. Chiefton) tubers was purified 2289-fold to electrophoretic homogeneity and a final o-phospho-L-tyrosine (P-Tyr) hydrolyzing specific activity of 1917 μmol Pi produced $min^{-1}$ $mg^{-1}$ of protein according to the procedure described by Gellatly et al, 1994.

Example 35

Preparation of Polyclonal Antibodies

Rabbit polyclonal antibodies were raised against PTAP following the procedure of Harlow and Lane (Harlow and Lane, 1988, pp. 92–114). Preimmune serum was collected from a 2 month old rabbit prior to immunogen exposure. Prior to injection, purified PTAP was deglycosylated using N-glycosidase-F supplied by Boehringer Mannheim (Laval, PQ, cat# 1365169). 500 μg PTAP was dialyzed against three 1000-fold volumes of 20 mM $NaH_2PO_4$, pH 7.2. The protein solution was made up to 100 mL in 20 mM $NaH_2PO_4$, pH 7.2 with 1% SDS and boiled for 2 min. To the mixture was added 900 μL 20 mM $NaH_2PO_4$, pH 7.2 containing 1.1% Nonidet P-40 and 60 units of N-glycosidase-F. The reaction was incubated at 37° C. overnight and dialyzed against three 1000-fold volumes of saline (150 mM NaCl). 500 μg purified deglycosylated PTAP in 2 mL saline was suspended in a dose of lyophilized RIBI (Hamilton, Mo.) adjuvant by 10 min heating to 45° C. followed by 3 min vortexing. The rabbit was injected with 100 μL of the immunogen suspension at 10 subcutaneous sites, 500 μL at two intramuscular sites and 50 μL immunogen at 10 intradermal sites. After 4 months, the rabbit was boosted with 300 μg following the same injection procedure. A heart puncture was performed 9 days after the boost yielding approximately 45 mL serum.

Example 36

Immunoremoval of Phosphatase Activity

Antiserum immunoremoval of PTAP activity was used to show that polyclonal antibodies were generated against PTAP. 0, 0.5, 1.25. 2.5 and 5 μL preimmune and immune serum were made up to 50 μL final volumes with 20 mM Tris-HCl, pH 7.4, 0.15 M NaCl. Samples were then mixed with 25 μL 4× incubation buffer consisting of 100 mM Hepes-OH (pH 7.5), 400 μg/mL BSA, 40% (v/v) glycerol and 4 mM dithiothreitol (DTT), and 0.5 units PTAP and 24 μL of a Protein-A Sepharose CL4B (Pharmacia) suspension in 20 mM Tris-HCl (pH 7.4), 0.15 M NaCl. Mixtures were incubated at 30° C. for 1 hour with shaking, centrifuged briefly and the supernatants were assayed for phosphatase activity using the phosphatase assay described below.

Example 37

Affinity Purification of Anti-PTAP Polyclonal Antibodies

Anti-potato phosphatase IgG was affinity purified from the immune serum. 15 μg potato phosphatase was transferred to immobilon-P polyvinylidene difluoride (PVDF) membrane and treated with sodium m-periodate after separation by SDS-PAGE. The blot was stained with 0.2% Ponceau S in 1% acetic acid, destained in 0.1 N NaOH and the phosphatase bands excised and placed into a 3 mL polypropylene screwcap tube. The membrane was blocked (protein side exposed) in buffer A containing 50 mM Tris-HCl (pH 7.5), 150 mM NaCl, 0.1% NP-40 and BSA by 1 h incubation at 37° C. The blot was then incubated for 1 h with crude antibody serum followed by three 1 mL washes in buffer A. The antigen-specific IgGs were eluted three times by the addition, with vortexing, of 400 μL buffer B containing 5 mM glycine-HCl (pH 3), 500 mM NaCl, 0.1% NP-40 and 1% BSA. After each eluate was removed, 200 μL of 1 M Tris-HCl, pH 8 was quickly added to neutralize the solution. The blot was washed three times in buffer A and the process was repeated until the crude serum was cycled through once.

Example 38

Phosphatase Assay

For substrates other than PEP, the method of Eibl and Lands (1969) was used to detect the Pi released by the phosphatase reaction (described previously).

Example 39

Culturing Rice and Potato

Rice seeds (*orysa sativa* cv. Japonica) were germinated on sterile 0.5× MS media containing 3% sucrose and 1% agar in 90 mm petri plates. For RNA analysis, seedlings were transferred to 20 mL sterile 0.5× MS medium containing 1% sucrose in 100 mL flasks with orbital shaking at 120 rpm and grown under illumination. Liquid media was replaced every 3 days for 14 days. After 14 days, media changes consisted of 0.5× MS medium, with 0.0093% (w/v) KCl substituted for $KH_2PO_4$, containing 1% sucrose and for phosphate starved plantlets. Phosphate starved plant tissues were harvested after 10 days treatment.Locally purchased potato tubers were segmented and planted in soil after pretreatment for 2 weeks at 4° C. Tuber, stolon, root, stem and leaf tissues were harvested after 30 days.

Example 40

Protein Extracts

Potato and rice tissues were harvested for crude protein extracts. 0.1 to 0.5 g of potato tuber pith, tuber epidermis (skin), root, stolon, stem and leaf tissue and rice seedling root and leaf tissue was placed in a preweighed microfuge tube. 1 mg of 2× extraction buffer consisting of 50 mM MES (pH 5.8), 8 mM $MgCl_2$, 1 mM phenyl methylsulfonyl fluoride (PMSF) and 1 mM DTT was added for each mg of sample and homogenized with a microfuge tube shaped hand-held homogenizer. Samples were centrifuges at 13,000 g for 5 min at 4° C. and the clarified supernatant was transferred to a fresh microfuge tube. A sample of the supernatant was removed and the protein concentration was determined by the method of Bradford (1976) using the BioRad (Mississauga, ON) prepared reagent and bovine γ-globulin as standard. 10 μg of each protein sample was made up to 10 μL with 2× extraction buffer.

Example 41

Western Blotting with Anti-PTAP Antibodies

Western Blotting was performed according to the protocol described in the BioRad manual.

Example 42

Isolation of Total RNA and mRNA

Total plant RNA was isolated following the CTAB-based protocol of Chang et al. (1993). Messenger RNA was isolated with the protocol and components of the Promega PolyATract mRNA Isolation System III (cat# Z5300).

Example 43

Northern Blotting

Northern blotting was performed in accordance with the standard protocol described in the Schleicher & Schuell manual (Schleicher & Schuell, Inc., Keene, N.H.).

REFERENCES

Akiyama, T., Uchimiya, H., Suzuki, H. (1981) *Plant Cell Physiol*. 22:1023–8

Altschul, S. F., Gish, W., Miller, W., Myers, E. W. Lipman, D. J. (1990) *J. Mol Biol*. 215: 403–10

Alvarez, E. F. (1962) *Biochim. Biophys. Acta* 59: 663–7

Bailey, K. M., Phillips, I. D. J., Pitt, D. (1976) *J. Exp. Botany* 27:324–36

Ballou, L. M., Fischer, E. H. (1986) In PD Boyer, EG Krebs, eds, The Enzymes, Vol 17. Academic Press, New York, pp 311–61

Barford, D., Flint, A. J., Tonks, N. K. (1994) *Science* 263: 1397–404

Beck, J. L., McArthur, M. J., de Jersey, J., Zerner, B. (1988a) *Inorganica Chim. Acta* 153: 39–44

Beck, J. L., de Jersey, J., Zerner, B. (1988b) *J. Am. Chem. Soc*. 110: 3317–8

Beck, J. L., McConachie, A. M., Summors, A. C., Arnold, W. N., de Jersey, J., Zerner, B. (1986) *Biochim. Biophys. Acta* 869: 61–8

Beck, J. L., Keough, D. T., de Jersey, J., Zerner, B. (1984) *Biochim. Biophys. Acta*. 791: 357–63

Bhargava, R., Sachar, R. C. (1983) *Biochem. J*. 212:73–7

Bieleski, R. L. (1973) *Ann. Rev. Plant Physiol*. 24:225–52

Bingham, E. W., Farrell, H. M., Dahl, K. J. (1976) *Biochim. Biophys. Acta* 429: 448–60

Boller, T. (1982) *Physol. Veg*. 20:247–57

Bradford, M. (1976) *Anal. Biochem*. 72: 248–54

Brautigan, D. L. (1992) *Biochim. Biophys. Acta* 1114: 63–77

Brooks, S. P. J. (1992) *BioTechniques* 13: 906–11

Byrne, B. M., Schip, A. D. V., Klundert, J. A. M. V., Arnberg, A. C., Gruber, M., Geert, A. B. (1984) *Biochemistry* 23: 4275–9

Cashikar, A., Rao, M (1995) *Indian J. Biochem. Biophys*. 32: 130–6

Chang, et al. (1993) *Plant Mol. Biol. Rep*. 11(2):113–116

Charbonneau, H., Tonks, N. K. (1992) Annu Rev Cell Biol 8: 463–93

Chen, R-H., Blenis, J. (1990) *Mol. Cell. Biol*. 10: 3204–15

Cheng, H-F., Tao, M. (1989) *Biochim. Biophys. Acta* 998: 271–6

Cho, H., Ramer, S. E., Itoh, M., Winkler, D. G., Kitas, E., Bannwarth, W., Burn, P., Saito, H., Walsh, C. T. (1991) *Biochemistry* 30: 6210–6

Christeller, J. T., Tolbert, N. E. (1978) *J. Biol. Chem*. 253: 1780–5

Chung, R. P-T., Polya, G. M. (1992) *Plant Sci*. 84: 153–62

Davis, B. (1964) *Ann. NY Acad. Sci*. 121: 407–27

Dent, M. E. (1994) Master's thesis. Queen's University, Kingston, ON

Dewald, D. B., Manson, H. S., Mullet, J. E. (1991) *J. Biol. Chem*. 267: 15958–64

Dietze, J., Blau, A., Willmitzer, L. (1995) In I Potrykus and G Spangenberg, eds, Gene Transfer to Plants. Springer-Verlag, Berlin, pp 24–9

Doucet, J. P., Trifaró, J. M. (1988) *Anal. Biochem*. 168: 265–71

Doyle, J. J. and Doyle, J. L. (1990) *Focus* 12:13–15

Dracup, M. N. H., Barrett-Lennard, E. G., Greenway, H., Robson, A. D. (1984) *J. Exp. Botony* 35:466–80

Dubray, G., Bezard, G. (1982) *Anal. Biochem*. 119: 325–9

Duff, S. M. G., Sarath, G., Plaxton, W. C. (1994) *Physiol. Plant*. 90: 791–800

Duff, S. M. G., Lefebvre, D. D., Plaxton, W. C. (1991a) *Arch. Biochem. Biophys*. 286: 226–32

Duff, S. M. G., Plaxton, W. C., Lefebvre, D. D. (1991b) *Proc. Nat. Acad. Sci. USA* 88: 9538–42

Duff, S. M. G., Lefebvre, D. D., Plaxton, W. C. (1989) *Plant Physiol*. 90:734–41

Eibl, H., Lands, W. E. M. (1969) *Anal. Biochem*. 30: 51–7

Elliot, D. C., Geytenbeek, M. (1985) Biochim Biophys Acta 845: 317–23

Erion, J. L., Ballo, B., Fox, T. W., May, L. A. (1992) *Plant Physiol*. 98: 1535–7

Gellatly, K. S., Moorhead, G. B. G., Duff, S. M. G., Lefebvre, D. D., Plaxton, W. C. (1994) *Plant Physiol*. 106: 223–32

Gellatly, K. S., Lefebvre, D. D. (1993) *Plant Physiol*. 101:1405–6

Gish, W., States, D. J. (1993) *Nat. Genet*. 3: 266–72

Gibson, D. M., Ullah, A. H. J. (1988) *Arch. Biochem. Biophys*. 260:503–13

Goldstein, A. H., Baertlein, D. A., Danon, A. (1989) *Plant Molec. Biol. Report*. 7:7–16

Goldstein, A. H., Danon, A., Bertlein, D. A., McDaniel, R. G. (1988) *Plant Physiol*. 87:716–20

Grover, N. S., Byrne, O. R. (1975) *Biochem. Genet*. 13:527–31

Guo, Y. L., Roux, S. J. (1995) *Plant Physiol*. 107: 167–75

Harlow, E., and Lane, D. (1988) Antibodies A Laboratory Manual, CSH Laboratory, Cold Spring Harbour, N.Y. pp. 92–114

Higgins, D. G., Sharp, P. M. (1988) *Gene* 73: 237–44

Hoffland, E., Findenegg, G. R., Nelemans, J. A. (1989) *Plant Soil* 113: 161–8

Hollander, V. P. (1971) In PD Boyer, ed, The Enzymes, Vol 4. Academic Press, New York, pp 449–98

Hooley, R. (1984) *J. Exp. Botony* 35:822–8

Hsu, R. Y., Cleland, W. W., Anderson, L. (1966) *Biochemistry* 5: 799–807

Jagiello, I., Donella-Deana, A., Szczegielniak, J., Pinna, L. A., Muszynska, G. (1992) *Biochim. Biophys. Acta* 1134: 129–36

Kamenan, A., Diopoh, J (1983) *Plant Sci. Lett*. 32: 305–12

Kamenan, A., Diopoh, J. (1982) *Plant Sci. Letters* 24:173–82

Kamps, M. P., Sefton, B. M. (1988) *Oncogene* 2: 305–15

Kanellis, A. K., Solomos, T., Mattoo, A. K. (1989) *Plant Physiol*. 90: 251–8

Kawabe, H., Sugiura, Y., Terauchi, M., Tanaka, H. (1984) *Biochim. Biophys. Acta* 784: 81–9

Kim, E. E., Wyckoff, H. W. (1989) *Clin. Chim. Acta* 186:175–88

Klabunde, T., Strater, N., Krebs, B., Witzel, H. (1995) *FEBS Lett*. 367: 56–60

Klabunde, T., Stahl, B., Suerbaum, H., Hahner, S., Karas, M., Hillenkamp, F., Krebs, B., Witzel, H. (1994) *Eur. J. Biochem*. 226: 369–75

Kubicz, A., Morawiecka, B., Kruzel, M. (1974) *Acta Biochim. Polon*. 21:113–7

Kubicz, A. (1973) *Acta Biochim. Polon*. 20:223–9

Laemmli, U. K. (1970) *Nature* 227: 680–5

Laine, A-C. (1988) *Electrophoresis* 9: 841–4

Lal, M, Jaiswal, V. S. (1988) *Plant Growth Regul*. 7: 29–37

Lau, K-H. W., Farley, J. R., Baylink, D. J. (1989) *Biochem. J*. 257: 23–36

Le Bansky, B. R., McKnight, T. D., Lawrence, L. R. (1992) *Plant Physiol*. 99: 391–5

Lee, R. B. (1988) *New Phytol.* 109:141–8

Lefebvre, D. D., Duff, S. M. G., Fife, C. A., Julien-Inalsingh, C., Plaxton, W. C. (1990) *Plant Physiol.* 93:504–11

Lefebvre, D. D., Glass, A. D. M. (1982) *Physiol. Plant.* 54: 199–206

Lycett, G. W., Grierson, D. (1990) eds. Genetic Engineering of Crop Plants. Butterworths, London Malboobi, M. A., Lefebvre, D. D. (1995) *Plant Mol. Biol.* 28: 854–70

Meyerowitz, E. M. (1989) *Cell* 56: 63–9

Miernyk, J. A. (1992) *Phytochem.* 31: 2613–6

Miernyk, J. A. (1987) *J. Plant Physiol.* 129:19–32

Mildner, P. (1976) *Biochim. Biophys. Acta* 429: 274–82

Moorhead, G. B. G., Plaxton, W. C. (1990) *Biochem. J.* 269: 133–9

Mulligan, R. M., Tolbert, N. E. (1980) *Plant Physiol.* 66: 1169–73

Murashige, T., Skoog, F. (1962) *Physiol. Plant.* 15: 473–97

Neumann, H. (1968) *J. Biol. Chem.* 243: 4671–6

Newmark, M. Z., Wenger, B. S. (1960) *Arch. Biochem. Biophys.* 89: 110–7

Nishimura, M., Beevers, H. (1978) *Plant Physiol.* 62: 44–8

Pan, S-M. (1987) *Aust. J. Plant Physiol.* 14: 117–24

Panara, F., Pasqualini, S., Antonielli, M. (1990) *Biochim. Biophys. Acta* 1037: 73–80

Plaxton, W. C., Moorhead, G. B. G. (1989) *Anal. Biochem.* 178: 391–3

Polya, G. M., Wettenhall, R. E. H. (1992) *Biochim. Biophys. Acta* 1159: 179–84

Polya, G. M., Hunziker, K. (1987) *Plant Sci.* 50: 117–23

Pot, D. A., Dixon, J. E. (1992) *Biochim. Biophys. Acta* 1136: 35–43

Potrykus, I., Spangenberg, G. (1995) eds. Gene Transfer to Plants. Springer-Verlag, Berlin Ramachandran, C., Aebersold, R., Tonks, N. K., Pot, D. A. (1992) *Biochemistry* 31: 4232–8

Rebeille, F., Bligny, R., Martin, J-B., Douce, R. (1983) *Arch. Biochem. Biophys.* 225: 143–8

Sambrook, J., Fritsch, E. F., Maniatis, T. (1989) Molecular cloning: A laboratory manual. 2nd ed. Cold Spring Harbor Laboratory, Cold Spring Harbor, N.Y.

Shibuya, H., Irie, K., Ninoyima-Tsuji, J., Goebl, M., Taniguchi, T., Matsumoto, K. (1992) *Nature* 357: 700–2

Stahl, B., Klabunde, T., Witzel, H., Krebs, B., Steup, M., Karas, M., Hillenkamp, F. (1994) *Eur. J. Biochem.* 220: 321–30

Sträter, N., Klabunde, T., Tucker, P., Witzel, H., Krebs, B. (1995) *Science* 268: 1489–92

Suerbaum, H., Körner, M., Witzel, H., Althous, E., Mosel, B-D. (1993) *Eur. J. Biochem.* 214: 313–21

Sugawara, S., Inamoto, Y., Ushijima, M. (1981) *Agric. Biol. Chem.* 45: 1767–74

Szabó-Nagy, A., Oláh, Z., Erdei, L. (1987) *Physiol. Plant.* 70: 544–52

Uchimiya, H., Kidou, S-I., Tetsuo, S., Aotsuka, S., Takamatsu, S., Nishi, R., Hashimoto, H., Matsubayashi, Y., Kidou, N., Umeda, M., Kato, A. (1992) *The Plant Journal* 2: 1005–9

Uehara, K., Fujimoto, S., Taniguchi, T., Nakai, K. (1974) *J. Biochem.* 75: 639–49

Ueki, K., Sato, S. (1971) *Physiol. Plant.* 24: 506–11

Van der Wilden, W., Herman, E. M., Chrispeels, M. J. (1980) *Proc. Nat. Acad. Sci.* 77: 428–32

Verjee, Z. H. M. (1969) *Eur. J. Biochem.* 9: 439–44

Walton, K. M., Dixon, J. E. (1993) *Ann. Rev. Biochem.* 62: 101–20

Wang, Z., Ming, L-J., Que Jr., L. (1992) *Biochemistry* 31: 5263–8

Willmitzer, L., Basner, A., Frommer, W., Hofgen, R., Liu, X-J., Köster, M., Prat, S., Rocha-Sosa, M., Sonnewald, U., Vancanneyt, G. (1990) In GW Lycett and D Grierson, eds, Genetic Engineering of Crop Plants. Butterworths, London Zhang, Z-Y., Andrea, M. T., MacLean, D., McNamara, D. J., Dobrusin, E. M., Sawyer, T. K., Dixon, J. E. (1993) *Proc. Natl. Acad. Sci. USA* 90: 4446–50

Zhang, Z. Y. (1995) *J. Biol. Chem.* 270: 16052–5

Zhao, Z., Zander, N. F., Malencik, D. A., Anderson, S. R., Fischer, H. (1992) *Anal. Biochem.* 202: 361–6

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. Isolated nucleic acid comprising SEQ ID NO: 1, SEQ ID NO: 11, or comprising 20 or more sequential nucleotides of SEQ ID NO: 1 or SEQ ID NO: 11, said nucleic acid encoding a phosphatase.

2. Isolated nucleic acid according to claim 1 wherein the nucleic acid comprises 50 or more sequential nucleotides of SEQ ID NO: 1 or SEQ ID NO: 11.

3. Isolated nucleic acid according to claim 1 wherein the nucleic acid comprises 200 nucleotides.

4. A vector containing the nucleic acid of claim 1.

5. A cell containing the vector of claim 4.

6. A transgenic plant or plant part, each containing the cell of claim 5.

7. A plant part of the plant of claim 6 selected from the group consisting of pollen, ovaries, seeds, embryos, hypocotyls, epicotyls, cotyledons, leaves, stems, roots, flowers, meristems, tissues, protoplasts, cells, and explants.

8. A photosynthetic organism containing the nucleic acid of claim 1 or a vector containing said nucleic acid.

9. Seed of the transgenic plant of claim 6.

10. A plant grown from the seed of claim 9 which contains isolated nucleic acid comprising SEQ ID NO: 1, or SEQ ID NO: 11, or a nucleic acid comprising 20 or more sequential nucleotides of SEQ ID NO: 1 or SEQ ID NO: 11, said nucleic acid encoding a phosphatse.

11. An isolated polynucleotide consisting of SEQ ID NO: 1 or SEQ ID NO: 11.

12. An isolated polynucleotide which hybridizes under high stringency conditions to SEQ ID NO: 1 or SEQ ID NO: 11, said nucleic acid encoding a phosphatase.

13. An isolated polynucleotide consisting of the coding region of the isolated polynucleotide of claim 11.

14. A vector containing the nucleic acid of claim 11.

15. A cell containing the vector of claim 14.

16. A transgenic plant or plant part, each containing the cell of claim 15.

17. A plant part of the plant of claim 16 selected from the group consisting of pollen, ovaries, seeds, embryos, hypocotyls, epicotyls, cotyledons, leaves, stems, roots, flowers, meristems, tissues, protoplasts, cells, and explants.

18. A photosynthetic organism containing the nucleic acid of claim 11 or a vector containing said nucleic acid.

19. Seed of the transgenic plant of claim 16.

20. A plant grown from the seed of claim 19 which contains isolated nucleic acid comprising SEQ ID NO: 1 or SEQ ID NO: 11, or a nucleic acid comprising 20 or more sequential nucleotides of SEQ ID NO: 1 or SEQ ID NO: 11, said nucleic acid encoding a phosphatase.

* * * * *